US008039008B2

(12) United States Patent
Klose

(10) Patent No.: US 8,039,008 B2
(45) Date of Patent: Oct. 18, 2011

(54) IDENTIFICATION OF RESIDUES CRITICAL FOR THE FUNCTION OF THE VIBRIO CHOLERAE VIRULENCE REGULATOR TOXT BY SCANNING ALANINE MUTAGENESIS

(75) Inventor: Karl E. Klose, San Antonio, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 309 days.

(21) Appl. No.: 12/020,398

(22) Filed: Jan. 25, 2008

(65) Prior Publication Data
US 2009/0104233 A1 Apr. 23, 2009

Related U.S. Application Data

(60) Provisional application No. 60/886,908, filed on Jan. 26, 2007.

(51) Int. Cl.
A61K 39/42 (2006.01)
(52) U.S. Cl. ............... 424/261.1; 424/185.1; 424/190.1; 424/200.1; 530/350; 435/243; 435/252.3; 435/172.1
(58) Field of Classification Search .................. None
See application file for complete search history.

(56) References Cited

OTHER PUBLICATIONS

Bhende and Egan, "Amino-acid-DNA contacts by RhaS: an AraC transcription activator," *J. Bacteriol.*, 181:5185-5192, 1999.
Bina et al., "ToxR regulon of *Vibrio cholerae* and its expression in vibrios shed by cholera patients," *PNAS*, 100:2801-2806, 2003.
Brown and Taylor, "Organization of tcp, acf, and toxT genes within a ToxT-dependent operon," *Mol. Microbiol.*, 16:425-39, 1995.
Bustos and Schleif, "Functional domains of the AraC protein," *Proc. Natl. Acad. Sci. USA*, 90:5638-42, 1993.
Champion et al., "A branch in the ToxR regulatory cascade of *Vibrio cholerae* revealed by characterization of *toxT* mutant strains," *Mol. Microbiol.*, 23:323-331, 1997.
Crawford et al., "Membrane iocalization of the ToxR winged-helix domain is required for TcpP-mediated virulence gene activation in *Vibrio cholerae*," *Mol. Microbiol.*, 47:1459-73, 1997.
Cuff et al., "JPred: a consensus secondary structure prediction server," *Bioinformatics*, 14:892-3, 1998.
DiRita et al., "Differential expression of the ToxR regulon in Classical and El Tor biotypes of *Vibrio cholerae* is due to biotype-specific control over *toxT* expression," *Proc. Natl. Acad. Sci. USA*, 93:7991-7995, 1996.
DiRita et al., "Regulatory cascade controls virulence in *Vibrio cholerae*," *Proc. Natl. Acad. Sci. USA*, 88:5403-5407, 1991.
Elliott, "A method for constructing single *lac* fusions in *Salmonella typhimurium* and its application to the *hemA-prfA* operon," *J. Bacteriol.*, 174:245-253, 1992.
Faruque et al., "Pathogenic potential of environmental *Vibrio cholerae* strains carrying genetic variants of the toxin-coregulated pilus pathogencity island," *Infect. Immun.*, 71:1020-1025, 2003.
Gallegos et al., "AraC/XylS family of transcriptional regulators," *Microbiol. Mol. Biol. Rev.*, 61:393-410, 1997.
Geourjon and Deleage, "SOPMA: significant improvements in protein secondary structure prediction by consensus prediction from multiple alignments," *Comput. Appl. Biosci.*, 11:681-4, 1995.
Gill, "The arrangement of subunits in cholera toxin," *Biochemistry*, 15:1242-8, 1976.
Gillette et al., "Probing the *Escherichia coli* transcriptional activator MarA using alanine-scanning mutagenesis: residues important for DNA binding and activation," *J. Mol. Biol.*, 299:1245-1255, 2000.
Grainger et al., "Binding of the *Escherichia coli* MelR protein to the melAB promoter: orientation of MelR subunits and investigation of MelR-DNA contacts," *Mol. Micriobiol.*, 48:335-348, 2003.
Grainger et al., "Transcriptional activation at the *Escherichia coli* melAB promoter: interactions of MelR with its DNA target site and with domain 4 of the RNA polymerase sigma subunit," *Mol. Microbiol.*, 51:1297-1309, 2004.
Greenberg et al., "Positive control of a global antioxidant defense regulon activated by superoxide-generating agents in *Escherichia coli*," *Proc. Natl. Acad. Sci. USA*, 87:6181-6185, 1990.
Griffith and Wolf, "A comprehensive alanine scanning mutagenesis of the *Escherichia coli* Rob transcriptional activator SoxS: identifying amino acids important for DNA binding and transcription activation," *J. Mol. Biol.*, 322:237-257, 2002.
Hanahan, "Studies on transformation of *Escherichia coli* with plasmids," *J. Mol. Biol.*, 166:557-80, 1983.
Haralalka et al., "Mutation in the *relA* gene of *Vibrio cholerae* affects in vitro and in vivo expression of virulence factors," *Journal of Bacteriology*, 185:4672-4682, 2003.
Hava and Camilli, "Isolation and characterization of a temperature-sensitive generalized transducing bacteriophage for *Vibrio cholerae*," *I Microbiol. Methods*, 46:217-25, 2001.
Herrington et al., "Toxin, toxin-coregulated pili, and the *toxR* regulon are essential for *Vibrio cholerae* pathogenesis in humans," *J. Exp. Med.*, 168:1487-1492, 1988.
Hulbert and Taylor, "Mechanism of ToxT-dependent transcriptional activation at the *Vibrio cholerae* tcpA promoter," *J. Bacteriol.*, 184:5529-5532, 2002.
Hung and Mekalanos, "Bile acids induce cholera toxin expression in *Vibrio cholerae* in a ToxT-independent manner," *Proc. Natl. Acad. Sci. USA*, 102:3028-3033,2005.
Hung et al., "Small-molecule inhibitor of *Vibrio cholerae* virulence and intestinal colonization," *Science*, 310:670-4, 2005. Jair et al. "Purification and regulatory properties of MarA protein, a transcriptional activator of *Escherichia coli* multiple antibiotic and superoxide resistance promoters," *J. Bacteriol.*, 177:7100-7104, 1995.
Jair et al., "Transcriptional activation of promoters of the superoxide and multiple antibiotic resistance regulators by Rob, a binding protein of the *Escherichia coli* origin of chromosomal replication," *J. Bacteriol.*, 178:2507-2513, 1996.
Krukonis and DiRita, "From motility to virulence: sensing and responding to environmental signals in *Vibrio cholerae*," *Curr. Opin. Microbiol.*, 6:186-90, 2003.

(Continued)

Primary Examiner — Jennifer Graser
(74) Attorney, Agent, or Firm — Fulbright & Jaworski LLP

(57) ABSTRACT

Disclosed are *Vibrio cholerae* comprising a mutated transcriptional regulatory protein (ToxT) amino acid sequence, wherein the mutation results in a reduction in the expression of cholera toxin by the *Vibrio cholerae*. Also disclosed are *Vibrio cholerae* comprising a mutated transcriptional regulatory protein (ToxT) amino acid sequence, wherein the mutation results in an increase in transcription of the nucleic acid encoding the mutated ToxT. Vaccines comprising the aforementioned *Vibrio cholerae* are disclosed. Also disclosed are amino acid sequences that encode a mutated ToxT protein.

9 Claims, 5 Drawing Sheets

OTHER PUBLICATIONS

Kwon et al., "Crystal structure of the *Escherichia coli* Rob transcription factor in complex with DNA," *Nat. Struct. Biol.*, 7:424-30, 2000.

Lee et al., "Regulation and temporal expression patterns of *Vibrio cholerae* virulence genes during infection," *Cell*, 99:625-634, 1999.

Martin and Rosner, "The AraC transcriptional activators," *Curr. Opin. Microbiol.*, 4:132-137, 2001.

Martin et al., "Structural requirements for marbox function in transcriptional activation of mar/sox/rob regulon promoters in *Escherichia coli*: sequence, orientation and spatial relationship to the core promoter," *Mol. Microbiol.*, 34:431-441, 1999.

McGuffin et al., "The PSIPRED protein structure prediction server," *Bioinformatics*, 16:404-5, 2000.

Mekalanos et al., "Cholera toxin genes: nucleotide sequence, deletion analysis and vaccine development," *Nature*, 306:551-557, 1983.

Mukhopadhyay et al., "Characterization of VPI pathogenically island and CTXphi prophage in environmental strains of *Vibrio cholerae*," *J. Bacteriol.*, 183:4737-46, 2001.

Niland et al., "How AraC interacts specifically with its target DNAs," *J. Mol. Biol.*, 264:667-674, 1996.

Ouali and King, "Cascaded multiple classifiers for secondary structure prediction," *Protein Sci.*, 9:1162-76, 2000.

Pearson and Mekalanos, Molecular cloning of *Vibrio cholerae* enterotoxin genes in *Escherichia coli* K-12, Proc. Natl. Acad. Sci. USA, 79:2976-80, 1982.

Peterson and Mekalanos, "Characterization of the *Vibrio cholerae* ToxR regulon: identification of novel genes involved in intestinal colonization," *Infect. Immun.*, 56:2822-2829, 1988.

Poore et al., "Identification of the domains of UreR, an AraC-like transcriptional regulator of the urease gene cluster in *Proteus mirabilis*," *J. Bacteriol.*, 183:4526-4535, 2001.

Porter and Dorman, "In vivo DNA-binding and oligomerization properties of the *Shigella flexneri* AraC-like transcriptional regulator VirF as identified by random and site-specific mutagensis," *J. Bacteriol.*, 184:531-539, 2002.

Porter et al., "Direct and indirect transcriptional activation of virulence genes by an AraC-like protein, PerA from enteropathogenic *Escherichia coli*," *Mol. Microbiol.*, 54:1117-33, 2004.

Prouty et al., "Characterization of functional domains of the *Vibrio cholerae* virulence protein ToxT," *Mol. Microbiol.*, 58:1143-1156, 2005.

Rhee et al., "A novel DNA-binding motif in MarA: the first structure for an AraA of an AraC family transcriptional activator," *Proc. Natl. Acad. Sci. USA*, 95:10413-8, 1998.

Rosenberg et al., "Bile salts and fatty acids induce the expression of *Escherichia coli* AcrAB multidrug efflux pump through their interaction with Rob regulatory protein," *Mol. Microbiol.*, 48:1609-1619, 2003.

Ruiz et al., "Leucines 193 and 194 at the N-terminal domain of the XylS protein, the positive transcriptional regulator of the TOL meta-clevage pathway, are involved in dimerization," *J. Bacteriol.*, 185:3036-41, 2003.

Schuhmacher and Klose, "Environmental signals modulate ToxT-dependent virulence factor expression in *Vibrio cholerae*," *J. Bacteriol.*, 181:1508-1514, 1999.

Sengupta et al., "The global regulator ArcA modulates expression of virulence factors in *Vibrio cholerae*," *Infect. Immun.*, 71:5583-5589, 2003.

Shi et al., "FUGUE: sequence-structure homology recognition using environment-specific substitution tables and structure-dependent gap penalties," *J. Mol. Biol.*, 310:243-257, 2001.

Simons et al., "Improved single and multicopy *lac*-based cloning vectors for protein and operon fusions," *Gene*, 53:85-96, 1987.

Söding et al., "The HHpred interactive server for protein homology detection and structure prediction," *Nucl. Acids Res.*, 33:244-248, 2005.

Soisson et al., "Structural basis for ligand-regulated oligomerization of AraC," *Science*, 276:421-425, 1997.

Svennerholm and Holmgren, "Identification of the *Escherichia coli* heat-labile enterotoxin by means of a ganglioside immunosorbent assay (GM1-ELISA) procedure," *Current Trends in Microbiology*, 1:19-23, 1978.

Taylor et al., "Use of *phoA* gene fusions to identify a pilus colonization factor coordinately regulated with cholera toxin," *Proc. Natl. Acad. Sci. USA*, 84:2833-2837, 1987.

Tischler and Camilli, "Cyclic diguanylate regulates *Vibrio cholerae* virulence gene expression," *Infect. Immun.*, 73:5873-82, 2005.

Waldor and Mekalanos, "Lysogenic conversion by a filamentous phage encoding cholera toxin," *Science*, 272:1910-1914, 1996.

Wickstrum and Egan, "Amino acid contacts between Sigma 70 Domain 4 and the transcriptional activators RhaS and RhaR," *J. Bacteriol.*, 186:6277-6285, 2004.

Withey and DiRita, "The toxbox: specific DNA sequence requirements for activation of *Vibrio cholerae* virulence genes by ToxT," *Mol. Microbiol.*, 59:1779-1789, 2006.

Withey and DiRita, "*Vibrio cholerae* ToxT independently activates the divergently transcribed *aldA* and *tagA* genes," *J. Bacteriol.*, 187:7890-7900, 2005.

Wood et al., "Interdependence of the position and orientation of SoxS binding sites in the transcriptional activation of the Class I subset of *Escherichia coli* superoxide-inducible promoters," *Mol. Microbiol.*, 34:414-430, 1999.

Yu and DiRita, "Analysis of an autoregulatory loop controlling ToxT, cholera toxin, and toxin-coregulated pilus production in *Vibrio cholerae*," *J. Bacteriol.*, 181:2584-92, 1999.

Yu and DiRita, Regulation of gene expression in *Vibrio cholerae* by ToxT involves both antorepression and RNA polymerase stimulation, *Mol. Microbiol.*, 43:119-134, 2002.

SEQUENCE LISTING

<160> NUMBER OF SEQ ID NOS: 24

<210> SEQ ID NO 1
<211> LENGTH: 41290
<212> TYPE: DNA
<213> ORGANISM: Vibrio cholerae
<220> FEATURE:
<221> NAME/KEY: CDS
<222> LOCATION: (26895)..(27725)

<400> SEQUENCE: 1

```
taagttgatc ttgtttttta acttattgtt tatatttaaa ttgtattgat ttgattttta      60
atggtgtacc ttttagtgta cccataaatt gttgctactt acccaatggc acttctgtct     120
catttatttt ttaagttttt atccatgctt ataggccctg ataaagcagt agcgtgaatg     180
acttaaagtg tgtgattcat agacatcctt tcaactatac tgggtgtcta tggacagaga     240
aatccaacaa agactacagt gggtaaaaat gtatgaggaa tgtggtgatg caggcctcgt     300
atgtcgacgc tgtggtattt ccagaccaac attacgaaag tgggctaagc gatataagca     360
atgtggaatc gctggtctgg aaagccagag cagacgccct cattcatctc cagataccaa     420
actcactgat gagctaagag cattgatcct tacgatgcgt gacaaacgca atttaggggc     480
gcgacgttta caaacggaat taatccgact tcacaaaata cacctaagca cagcgacact     540
ccataaagtt ttatccgaag catcagtcaa acccatcgta acttaccgac gcaaaaaaga     600
tttccaaaga tatgagcgcc caattcctgg tgatagagtc cagatggaca cgtgtaaaat     660
agcgcctgga atttaccagt atacagctat tgatgattgc tctcgctatc gggttctaag     720
gtgctactct cggcgcacag cagcaaatac agtcgacttt atcgattgtg tcgtggaaga     780
gatgccattt cctatccagc gtattcagac ggacagaggg cgtgaattct ttgctgaaaa     840
agtccagaaa caactcatga tttatgggat caagtttcgc ccaaataagc ctggctcacc     900
tcacttgaat ggcaaagtgg aacgttcgca gaaacagat aaaagtgagt tctatccgac     960
catagatgtc tctgtgggc tgcaagaact ggatctgcta ctagctgaat ggcaacacta    1020
ctacaactgg gaacggcccc acagttcgtt aaatgggcta accccgatag acaggattac    1080
tgagatatct gatcaaactc ctttgtctga agaggtatct cagaactacc agatcaagaa    1140
agagcggttt caagagcaaa attacaagct cgatcttcag ctaagaaaat tgaaaccatc    1200
tctatgaatc acacacctac ttagattgat agttagccaa tagggcaagt tttaggcata    1260
ccaagccctg ttatcttatt taacgctttg atcatcgggt aagcctcacc aacctgagca    1320
ttgtagtttc tcagacttaa tcgtccacct aacaactgct tcactcgata cattgctgtt    1380
tcagatagtg agcgtttatg atagccgtac cgcttttttcc acttattgtt ggacccgtag    1440
```

```
agcttctggc aacctaccgc taaatgcaac tttctccaga ctctacgctt cccgtcagta      1500
ccatgcttct tgaccttcca ttcaccttcg ccataaacct tgagacctgt tgcatcaatg      1560
gctagatgct gtattgcacc tctagtcttt ggtttaaatg aaacctcgac ttgcttagct      1620
cttcgactga tacaactgta atgtgggcag actataggga cgttagccaa tgaaaaaaca      1680
gaatcgataa acccttacaa tgctctaaac tgcattgaga aaactcgttt caccataagc      1740
gcagtaataa tggctaagtc gctgaactgg cgaggtctac ctcgtttatc ttgtttgctc      1800
tgcttccact ggcgagtggc ttcttcatca atccagaaag tgagtgaacc acggttgatt      1860
aaggctttgt tgtactgttt ccaattcgtt gttttgtagc gaggtttcgg catgagacta      1920
ggggaattaa cttacttaac ggatcagatc gtaaccttcg gatttagttc cctcgaatta      1980
cgcaacaaag cctgcccacg gtggcattat tttaatggga atgccaaatg tattaattgg      2040
tgattaatgt gattttttgt aaagatagcc aagtttataa gaatatatta atgatagata      2100
gtataagtat tcttaaataa gataaggatc cttgagttgg tttgtggtgt aatgacttaa      2160
aatttttata tcgtaaattt caatgaaaat taaattgagt gaattttttga tatattaggg      2220
agatgttgct cacctaaagt gagcaatatt agatttaaaa tagacctaga ggatgaatct      2280
catgactaat aagaacgttt tttatatttt ggtaatgact caatgttaat ttgtgtgttt      2340
ctcgtccaat gccagatttt ttatatccac caaaagccgc atgagcagga tatgcatgat      2400
aacaatttac ccatactctt ccagctttaa tgttttttgc catacgatga gcaatattta      2460
tatcacgtgt ccacacaccg gcacctaaac cataaacagt atcattagca aggtgcagtg      2520
cttcaatttc atctttaaac ttagtgattg caattacagg tccaaatatt tcctcttgaa      2580
agatatgcat ctgattatga ccaaagaata gggttggttt aatataataa ccaccagata      2640
aataattttc ttgattgtta ggatgcccac caaaaattag ctctgcccct tcatctttac      2700
ctatttgtat ataaccaaga atcttatcgt actgttcttt agatacttga gcaccaattt      2760
gtgtttcggt atctaaagga tttccttgtt taattaatgc tactcgttca ataattttgg      2820
caatgaattt ttcataaata gattcatgaa ctaaaattct agatggacag gtacaaacct      2880
caccttggtt gaaaaatgct aaaagtgcac cctcaataca tttatcaaga tattggtctt      2940
catgagaaaa gatatcgggg aaataaatgt ttggagattt ccacctaat tcgattgtgg      3000
atggaatcaa gttatccgcc gcacatttaa gaatatggtt accaatttca gtagaacctg      3060
taaatgctag tttatcgata cgttggcttg ttgctaatgc attacctgct tcagagccga      3120
aaccattaac aacattaata acaccagctg gaattaaatc accaataatt tccattaaaa      3180
acaaaattga acgggggtt tgttctgcag gtttgagaac aacagtacaa cctgctgcaa      3240
gagcgggagc taatttccaa gcagccatga gtaacgaaaa attccatggt attatttggc      3300
ctacaacacc tattggttcc ggtaaatgat aagttaacgt tctagagtca agttcggaag      3360
cagcaccttc ttgtgatcga atacaagccg caaaatatcg aaagtgatca atagtcaacg      3420
gtaggtcagc tgctaaagtt tcacggatag gttttccatt atcccatgat tcaactattg      3480
cgagagtttc taaatttgat tcgattcgat cagcaatcct cagaagaata tttgatcttt      3540
ctactgcact tgttgtagac catgattcaa gtgcattatg ggcggcatct agagcaagtt      3600
cgacatcttg cgaagacgag cgagcaacac gacaaaacac cagtccattt actggtgacg      3660
tattgctaaa atattcgcca ctgtgtggct tcatccattg acctccaatg taattatcat      3720
atacatcttt gaaatgaaca gtcgaagttt cgctattagg aattggataa atcatataaa      3780
aaacagctac cttttttgat ggaaaaatta ttctatagaa tgaaattaac ttcttacatg      3840
```

```
agaattgatt taaaaaaaca aaatcgtatt gaaatttcaa tgtaaaattt taagttaata    3900
tttaatgcat taaaaaaaca tcaatacgtt tcccttgtct ttatttttt gttaaatgat     3960 tttttcgaaa aatgtttacg aggagttagt ggtggtaaga tattcactct taatgaaagt   4020 ttctttgca atacttattt tcttagttgg atgtaatgag aatgcaacat ccagtaacga    4080
ccagtatttg actgatcctg atataagtga acaaacaaag aagccatcaa ggcctataat   4140
tgatgaaaaa aataaaggtg taacagatac ttcggttaca atagaatggg ataagattga   4200
gtgtgaaaaa aattttagtc attataatgt aattgtctat agaaagatc gaatagaaga    4260 tgtaataact atcagaacta ggaataatag tgttttatc gatgatttaa aacctaacag    4320
ccagtattct atagatgtct caagttgttt acactctgct tgttcagaaa gcgcaaaaat   4380
agaattcatt acgttgaacg atatagatta ttatcacacc acagaaatag aaaaaaatgt   4440
gtatggaagc ttggaaggtg aagttagatt tgtgcaaacg catgtcattt ctcctgaggg   4500
tagaaagaat gagcctgaaa taatcacagg aagagatgca ttaatattgt ttaagccatc   4560
aataaaaaac tcaagttcaa ttttgatgaa aatttattca gaagatggac tcactagcaa   4620
agttgtaatg aaatcaccat ctatgttgcc aaaaactgat caaccaatag atattgatga   4680
aaataataaa gttgtaagtt actctaactc atattggagt gcagagatac catggaataa   4740
aatgaaaagt ggtatgtcat tacattttga agacgaaaac ggcaacttag gtattattga   4800
gtcagaacgt ataaaatttt cagcacctag tgaattgatt attcaaaata tagatcttgg   4860
aatgttatat aaaccaagag gaagaaatat cgtaataaaa gaattggaaa gaacagccgt   4920
tgattacttt cagaaagttc ctgtctcaaa gttgattttt tcagattata cccctattca   4980
ttttgaaaaa ataacattac caaatggttc agtatatact gagaaaagtg ctgatatagg   5040
tggatggcat caaggtgata tgagagaagc agtagggaaa gcactagtat ctaccggaat   5100
aaataatgct aatttaggta tagttgcctc gtcaggatat tctcaacaat acaacagatt   5160
aacgaatcat attaccgcac acacaaatat tggatattat aacaatggag tggttgtgca   5220
tggagggagt ggtggtggtg ggatcgttac actagaaaat acacttcata cgaatggtc    5280 tcatgaattg ggacataact atggattggg acattatgtt gcaggtggta ctagtcatgg   5340
acctgatact tcatggggtt gggatggcta ttataaaaga ttcatagcta actttgattg   5400
gaaacgttca cccacaatcaa atataaggcc agataatcaa gaagttgtta agcccttcat   5460
ggacaagtat acatatcttt gggatgcaat gtctggagga tatgaccatc aaaatggaat   5520
cattagtaga tatacacttc atcatccata tgttgcaaga attatccaag attggcttaa   5580
aaatggggct gttgtaataa ataatgatta tatggtttgg gatgaattaa aaaatatcta   5640
tgtgtataag ggaacgaact tcaaagttcc aataaaaaaa ggtgtacctg ttgtgacgat   5700
attaggggtt tatgatcctg acaaaattaa tccaagtcaa ttgtatcctc gacatacag    5760 caattatgga aatatattcg atttagaaaa acctcgttca gaatcatcct taaagggtg    5820 gcaatatgtt aaagatgtca actatctaga tagagttaat acacattggc atacgatgct   5880
cgtaaataga aagaagaaa aaatatgtcg attttcttat ctaagcccta aaggtaaaaa    5940
atttgaattt ctagggtatg aagacattga gaataaaata tgcacaggaa gtagaagtat   6000
tcactattta aagacggca agaaaaatcc aatagaatcc aagtataatg attatttttt    6060
attatcaata gatggtgatg gagaaataag ttatgttcct gattctacta ttggtgaaag   6120
taaaatatgt tcactaaaga tgtctggtac tgtatacggt gcaggtttta ttaaaggaaa   6180
ctcttgtcgg caaattgacg gtgttttat gaacggattt caatgggctt ttacattaaa    6240
```

```
tcaatcagga gtaaatagta cctatacatg gtcaaatgaa tgtgtattaa aaattaaaga    6300
taaagataat aatattgaat caatatcgat accaaattat agaatagaaa aaaatcagag    6360
taataaaatt catcttaata taagcagaga aaagcccata atagatatta acgtgtattg    6420
tggagaacat gagttaacta gcataaaggt ttctgataat cctgatataa aattactaaa    6480
aggacctatt attgttgggc aagagcatgg ttacacaagc tatgagccta agcttcctag    6540
tggttggttc aaacattatg acaattttga acccaaaaat gaaatcaacc atgaattagg    6600
aaagatgcgt gtaaatgata atgatgaata tatttgtcga tttaattttt ctgattcaga    6660
tagggaaatg aaatttgttg gttatgtgag tcaattatct gaaagtaagt acatttgtac    6720
tggtggaagt gagatctatt acaagaaaaa cgacattaat attgaactat catcaaaaga    6780
aaacgatttt gaatggttat cagtaagaga taaaaatttg ataggttcaa aaatagaatt    6840
tgataacaat aagacattgt gcgtattaga taatagatca ttttatggtg ctggttacct    6900
cgatgaaaac aatagatgta cacaagatag acaaattcat tggtctaatg gtaaacaatg    6960
gttatttagt acttataaaa cgatgaccta ccattaaaac tatagaactt tttttgatga    7020
ctgtggtttg ttcattcata gttagattga aaaataaaat actaactata tggtgtaatc    7080
atatagttag taaggattaa ggactattca tgttcaataa aaaaattaca ataacttcaa    7140
ctggtattac gttgtctatt ttttcccttta tggctaaagc tgatcctaaa attaatttcg    7200
cagtggatta tttctcttat ggtagtaatg gaagatgtat ggttgctatg gagatcgaaa    7260
aaagtaattt aaatgaaata tataataaa ttaataaaaa tcactttgat atcgattttg    7320 aagtttact gtatgagaaa gataaaaatg gaaaaattga aagcctcat ggtacagaga    7380 tggttaaatt caaatttaat gaatttgata accttgttca tgatcatgtt attgtcatgt    7440
caaaaatgga acttccatat tcatggtggc atgaatgtaa agtcttaagt gttaatttat    7500
cagataagaa atatgctaaa gttacaatat atgacgattt taatggcgac gtttcattta    7560
gaaatatagt tgaaaataat aagatttcca gttttgattt cttttctgat atagtaaaca    7620
tggcattcgc ctatagaatg aaagatgaaa aaccaacaga gaatgagatc ctccagaaca    7680
tatccaaaat gaaaagttat aataatggaa agtcagggaa tgaatcacta aatagaaaaa    7740
ttattggata tacaaacact atatcttttag gagatagtgg tataaatggt tctataggtt    7800
ttaatatatc tgaagatttc attaaattac gaacaaaaga taagatcaat aattttataa    7860
aagaaaaaat cgtaaaacct gcagtagaag ttggtatcgt tgatcgtaaa tttcaagaat    7920
caaagtatat tgatgaatta agacagagac tactaaaaag tttaaatcaa gatcattact    7980
ttgaatatgg ttcagagaaa aatttgcaat tatcattggt aatgatgttc tcagacttgt    8040
acagtcagcc tatattatcc tacggaaaaa cgatacctgc atacagcgat ccttttttta    8100
gtgatttatg ggagtcaatg ttaagtggat tcatcaatag tattgaacct gtgaaattat    8160
atgaacatga gtcatatcat gggcattcga tatcattaaa catggatagt gaattttgc    8220 atggctttaa tgatattgct tcatcaataa aaattccgaa agggtggcaa gttactttat    8280
ttgaacatgg cggattttact ggttcttcta ttgtagctaa tagtgatatt aaggcattag    8340
gagagaagaa tctgaatgat acggtaagtt ctttgatggt tgagtatgtc ggtgatgatc    8400
cttccgaact ctatgacatg ttattgttga ccatcaatta tggtaacctc tcaggtatag    8460 attttttctcg cgaaattttt aataaaaata aggatattat agttgactat aaaaagggta    8520
ccattaacca tagaggtatt actggtggat ttttggggaa gacttttgct caagttgcag    8580
ccattttgta tcaaaaatct attgaggagc tcagctatat tgagttactg agtactaaaa    8640
```

```
atgcattaga aagtattggt attgacaccg tatacccttca tggcagtatg gataatataa    8700
aagcaagtct attcttgagg atcaacaata atctatcaaa aacgttactt cctgaagagg    8760
tcggtattgg atctgagcca tttattattg atgaattatt ggcaaaaata atcaattaac    8820
aatgtttaac ttttctaatg cattagataa gcttactgaa gatatttatt ctaatgctaa    8880
tttatatcgt tcagataatg ttgtaagact ctatgctgat cataactata caggtcacta    8940
tatagatatt gaaaattcga cgaaattcct acatggattt aatgatacac tttcgtcttg    9000
gactatccca cacggctggt ctgtacgatt ttatgaacat ggtgactatc aaggacgtta    9060
ttggacaaga gatgcttctg gaaatgaatc aggatttaat gatgtaatta gctctattga    9120
gatattgaaa aaacatctg ggataaaagg tagcttaata cgtaatgagc ttgaatcatt    9180
aaaaaatagc tacagagaaa tagataaatt tcaagtaatt gtcggttatg aaaatgaaac    9240
accaatttat gcccttcctt taactgatga gcttttttgct aaagctcagc tgtacagtta    9300
tggattagat gccaactttg ttgacaaaca ctggaagtca tacctaaaaa aaggccgctt    9360
gtctcttatc cccggggttc gtgtagggaa ggatattctt aaaaaggatg ctgctgcatt    9420
aggaggacat gtaacaacaa aaggtgcaca agatttatgg agaagaaaat accaagaaat    9480
cagccaagtt atgtcaaagt atattgcaac tcttatttca tttaaagcaa agctagaggg    9540
aaaagaatca tgggatattc aatctgaaaa taaaaatcgt tcagttagat ttaattttgg    9600
attcggaatt acatattata atatgggtaa taatggtaaa gcccattcaa gatatgaaaa    9660
tattccaact caaagctggg tcatgacggg taaggatata agttattcgg ttacgacacc    9720
tggtgattta ttgagcctgt tcagtcttaa taatttttaaa gtgatagaac ctatcgattt    9780
taattcaggc tcgaataatt atccactttta tcaattgatg aactccaatt acgccgataa    9840
gtgttcatat tatcaagatg gatggtatcc tcggtggaat gtgtgtgata caaaatttat    9900
aacaagaaat aaaaaatcat ataatacaaa agacatcatg tcatatggat ggcaagagtt    9960
tctaaatttt aaaatgaacg atttgaagac tgtacaaaca gatagagata tagcatatca    10020
agtattgatg gcgattcttc ctgtatgggg aactgttgaa gatattaaat cgggtgatgc    10080
aggaatggca actcttggtg tgttaggtga cgtaatgttt tttttaccca tagcaaaaag    10140
tgtttctagt atcggaaaac tatcagctaa agctgcgtcg tctaaactac taccgagaaa    10200
tgttaagttt gttagaaatg tcattggcct aaacaaacaa ggtaagtatt cattaacatc    10260
atcgcaagct gatagagctt tctataaatt aaaaatacaa ggaaaactaa aggaactccc    10320
taaagttata ttaaatgaac ttaatcctat cgcaggtttg gatcagctcg ttgttacagg    10380
gacaagtaaa ttatataaaa aatattcatc gcgggttagt ataccctaaaa aaaatataat    10440
aggtgataac tcagttgtgt tttacgatga tttaagtttt aaatcagagg tgttttcagt    10500
atcatattta gatgatggtt atttaattat taatgatcaa tatcgagctg tttatattga    10560
tggtaactac tatagggtcg aatatgatcc aatactacgt gctaatttca tttatgaaca    10620
aaatagtggg agaaggatag aaattattaa agataaaaat ggcaattggt ctattaaaga    10680
aattaataat gggatttgtc cacttttttc gttaatgaat aatactaaag catgtcattt    10740
caccaacatt gatgatgcat aataagtat gggatttgac ccaaaaacca gaacagcatc    10800
aggattattg gagttgatta atggtcgata tggacctgat attaaagaat acttattaaa    10860
attaaattct tcgctatctc ttaattataa tatcgatata gatacctaa attgggtttt    10920
cgatactata gaaaattctg gtatgtctag atatgcattt actccatttg taaaaaatac    10980
tgatgccatc atgtatgata tgctaggtaa gtttttataat aataacatga gtattaaacc    11040
```

```
tgttttttg    aacaaatcgc   agtacaaaaa   attaaagaaa   actttagact   ctgataaaga   11100
attaattata   aatgtaattt   cagaacaaag   gaaaattaat   ctaaaggagg   cacaacagct   11160
cttcgatgaa   ttttatactt   ctgttacgaa   agatcctatt   tttggtttgg   attctataac   11220
acacgataga   ccggttattc   atgtcgtcgg   acacggtgat   gctggtgatg   aagtcatcta   11280
ccctggtgat   gcaagccatt   actattacgc   tttcgagtta   gctgatatgc   tgaaaaataa   11340
aggattaaag   ccggattcaa   tcataaaact   tgacttttgt   tggagtgctt   gctctctcaa   11400
accaagtgat   tattcaaaaa   cagaagtact   gactagtatg   aataaggggg   attacactcc   11460
tttatttggt   gacattgatg   atagctttct   ggggagtttt   gctaaagaat   taacggcaat   11520
gtaccctacg   ttccgtggac   aataatcgg    atacgtaggg   acagtattaa   acacaattca   11580
agataatgtg   ttaactttag   ctaatacaca   aggtcggttt   catgctgtag   aaatgaactt   11640
ttctgatggt   aaatttttt    tcaagaaaga   ggatgcagaa   gttatttatg   ggagttataa   11700
aaataaatga   gaaaatcgat   attgattagc   ttgtgccttt   tttctagcat   tacaaatgcc   11760
tgtccaattg   gtgatattct   agagtctatg   gaattaccat   tagaaattga   aacatcccat   11820
gagttgcgcg   cagaattggc   taagttaact   ggtggaactt   attatagaga   ttatttatat   11880
cgattaattg   atgaattaaa   cccatttttt   aaaactgacc   agatgctaac   agcagagcat   11940
acctactggg   caaacaatt    gcttgactct   ggtaagctta   aaaattttac   aagtgcactt   12000
ggttatgtga   aaataaacag   aaactctatg   ataccagagt   ttgaaggtag   atatcttgtt   12060
gcaaagaac   tctcaaaatt    agacccagcg   cttttaaaat   caggatggaa   tacggttcat   12120
gaaataaagc   ttgtggtgac   acatgataat   gtcactactt   attgggaaca   tttaaaagga   12180
cagcctgttc   gcggacatga   agctggcata   acgtgggatt   ctattccagg   agcaggatca   12240
ccagaaggtt   taacagaatt   agtgattgct   cttcaaaaaa   attcggatgg   taaatgggtt   12300
ataccaacag   gtaatcatgg   ttcgaaaaat   ctagttattc   atgagtttgg   tcatactcta   12360
gatcgtgtag   tgggtacata   ttttactggt   aagccctaca   gtcaaaatcc   gagttttat    12420
caagcttggc   ataatgatta   tcaactaggg   aagataaagg   aacactactt   cttgcaacct   12480
gagaataact   atgctgttgc   attagaggaa   tcatttgctg   aaggtctatc   gaaactttat   12540
gggatagaca   atatacaatc   aacttatgac   tggccctata   tctccgctta   tttctatgac   12600
cagtttaaga   aaacaataca   agaacaaaat   cagggttata   aataatttaa   actaaacttc   12660
taaacggatt   tttttatt    aatttggttt   gttttaata    gtttgtataa   tagcggtgac   12720
actaaagtag   tgtttatatt   tgaggaatta   aattatgact   gttacatttc   aaaataatcc   12780
tgtttctatt   tctggctctt   ttcctaaagt   aggtgatcgt   ttgcctagtt   ttactctttg   12840
tggtgctgat   ttgaacgatc   ttaacaatga   agatttaaa   ggaaaaaaga    ttgtaatgag   12900
cattttccc    agtatcgata   ctccggtttg   ttctaaaagt   gtgaaagttc   ttcaaaatgc   12960
acttatgact   cgcagtgata   cagtgcttct   ctgtgtttca   gcagatctgc   cttttgctat   13020
gtctcgcttt   tgtacagagc   atgcagtagc   taatgtcacg   aatgcatcgt   ttttcgtga    13080
gcctgctttt   actgaacgct   tcggtgtaaa   tctaaatgaa   ggtgctttac   gtgggcttgc   13140
tgctagagca   gtgattgttg   cagatgagtt   cggtgtaatt   acccacagtg   aattagtcaa   13200
tgaaatcacc   aatgaaccag   attacgatcg   tattttgatg   tcactataat   cagtaattag   13260
gccaatgcta   tctatcaata   gataaaaaag   cgttggatga   ctttataaaa   ggccctaagt   13320
tcccaaggct   tagagccttt   tatttttcaa   ttaatcatac   actcatgtcg   ccattcgtta   13380
tgcctcaaac   atggaataat   ttgtcctaaa   ccaatgatta   gaaaactttg   gtatagctaa   13440
```

```
catgtgtaaa ggttgttgtt gttgttgcat ggctacacga ttgtgcgaga aaaaaagcca    13500
gtcagctcaa ctgactggca ctagcctaat tatttcctat ttatgaagta agctcaattt    13560
taaaaaagct aagagcatca tttagattgg tggtcaaatc agagatattc tgatttgcct    13620
gtttagttcg ttccatcgcg gataaattct cttgaactag atatcgaata tcttccatct    13680
gttttgctac atcttcagtt actattttt gttcatttgc ggcagtcgaa acgatggagt    13740
ttatgtttga tatttcaaga accttatcag aaatcaggtt aaaggatgcg ataagtgccc    13800
gattggcaac ttgtgtttca tgaataagtg aaacattacg tgtcatcact tgatctgcca    13860
actgcgattg ctcttgcagt ttcaaaataa taccttgaat atctatagtc gattgctgag    13920
ttttcactgc aagagaacga acttcatccg ctactacagc aaatccgcgc ccctgttcac    13980
ctgcacgagc agcctcgata gctgcattta gggcaagtaa gttagtttga tctgatatat    14040
tattaatgac atccgtaacc gaactaatat tatcggaaaa ctcgcgtaac tgattgatta    14100
tttgttggga ttcatggatc gatagggtta ccatttcggt ttgtttgctt gatgaatcga    14160
taatatcatg actttcagca atcaattttt gggccgtctc cgcattaagc tctgcacttt    14220
gagcttgttg cattacatca aaagaagtac atgatagttg cgttgttgct gtggccactt    14280
gttcaatgag cccaagttct tgctgtgaat tattcgtatt cccttcaatt gaatacgtaa    14340
tgtcagtctg tttgatactt aaatcattca tagtccgatg agaatttctc accacatcaa    14400
gaagcctaaa ttgtaaattt tcaagacttt gggcaatagt gtcgagctcg ttatggaatt    14460
ttataggcct gcgttctttt atctgaccat cagaaaggga aagaatccat tctctgatct    14520
gtctaacacc tgagagttct tgcttagaa cccaatatag tccaattagc atcacgcatg    14580
aaaaaccact aaatccagca ataatcaact ggatatctcg cttgtatgtt tggacgattt    14640
gttgaatatc aataatagtg aacagtttat tttcaccatc tatttctgtt tgtgacactg    14700
caaaccaatg actatcagca tcactgaagg tgacatactg gcctgagacc agattttga    14760 acagaggctt ctctttcgtt aaatcttttc caattaaggt actgtgagtg agatcagatg    14820
caaatacatt aaaattccta tccgtcatca taaacatccc actgccgtta ggtgaggcaa    14880
tctgatcacc tgcaatatct aaagcgacac tgccgacaat gtcgttgcct acataaacag    14940
gggtggcaat agtgagaacg tgttgcccag ttgttttatc gatatcaaaa gctgtgtaat    15000
gtttagtacc gagttcgacc gttttaacaa accaatctct tctcaatgtc tttgcattcc    15060
aatctagagt accaatatct gtaaacatgg tgccatctaa actagcgaag gtaacaccaa    15120
taaatccatg attttcctgt atacgtaaag caatagcgtt gagttcttcg actgctttat    15180
cgcgaagtga attggctatt gcaactgaga gagagatatt aagttttta taaaaatcta    15240 aagaatcctg ataactttgc aaccgttctt gtgcctgctg agaactaagg ctagatatag    15300
attttgtttg atctgatagt ttcgagtgat agaaaaaggc agtaaaagcc gacgtaatga    15360
tgcacgcaag taataaaaaa accgaaatta ttttttttat cattagttta actctaagtt    15420
taaatggtta tcacggagta cttcgtgata attaaaaata aaattataaa ataatgatgt    15480
gaaaaatcag ctttttatcgt tttaaatagt atttttttc tttaggaaaa taaacttata    15540
aagttaaaaa aaagccccaa acggaagggg caaagtgtca caggaaagat aatgtaacca    15600
agttaataga tatggaatag gcactatagg gggagtgcta aaccgaatga actgtaacga    15660
atattgcttt ccgatagcat ggtttgctgt tttttttaat gttattttat ttttttaac    15720 aatttaaata ttatgcaatc gagttctcat tatcaactgc aaaattagat tgcaaataat    15780
tatattaaaa aaaatagaca taaaaaaatg ggtcgttatg attaagaaaa tgtaaagtaa    15840
```

```
tggggtatgt ccgcgtgatt tatcaatttc ccgataacct ttggtggaac gaatgcagta    15900
atcaagtcta ttatgcacaa gatccaatga agccggaaag gctgattggt acaccgagca    15960
taatgcaggc taagttattg aaaatactct gtgaatatca tccttccccc tgtccaaatg    16020
atcaaataat taaagcactt tggcctcatg gatttatcag ctctgaaagt ctaactcagg    16080
caatcaaaag aaccagagat tttttgaatg atgaacataa gacgttgatc gaaaatgtaa    16140
agttacaagg ttatcgtatt aatattatac aagttattgt ttctgaaaac attgttgatg    16200
aagctgactg tagtcaaaaa aaatcagtaa aagagcggat aaaaattgag tggggaaga    16260 taaacgtagt tccttatctt gttttttcgg cgctttatgt tgctttgcta cctgtgattt    16320
ggtggagtta tggccaatgg tatcaacatg aattagccgg catcactcat gatctacgag    16380
atttagcaag gttaccgggg ataacaatcc aaaaactgtc agaacaaaaa ctcatgttcg    16440
ctattgatca acatcagtgt tccgtgaatt atgaacagaa gacattagaa tgcacaaaaa    16500
attaaaagct tggggggggg ctgcaggtct attcgttgta gcactaggag taacgctcat    16560
cgcactcccg atgcgacaaa aaaactcgca cggcacaatg attattgatg gtacagtcac    16620
acaaattttt tctacttatc aaggtaatct atccaatgtt tggcttaccc agacagatcc    16680
acaaggtaac gtagtcaaaa gttggactac acgttatcaa acattgccag atcctagctc    16740
tcagaagcta aatttgattc ccgactactc agaaagtaat gtgagccgtg attacaatgt    16800
gttgagtatt tatcaactcg gcaaaggttg ttttctcgcc ttcccttaca agcagcttac    16860
ggctgaaaaa atgtggtttt cctgtcaaag cgatttttag ggtcttatca tgagccgcct    16920
agatagtgtg tgacgagtag gcgctcctcc acagtcaaag tgactgaaag tcatctcttc    16980
atctttaccc taatgttcgc agttgtattg agatcgtcaa caatataaca agtgtcaatt    17040
aattggctat acagcatgca cgagacgaac actgtcagta ccgcaccaga tccacgtagg    17100
tgggtatagt gataagagtc ttacccaatt tttatcgtca ttcataattt cgatctccac    17160
tccgaaaata ttttaacgca ttttatttgc attaaattac tttaaatcat ttgaattgaa    17220
taagttggcc ttttttttagt gtctgattta ttttgtgcgt gaatgttact cgtgtttctt    17280
tcaatgcaag tgtgttatta aaaaataaa aaaacacagc aaaaaatgac atctgtcaat    17340
tgtaggtgac tttgtgtggt taaatgtgcg tgttgcttac gttatctaaa aaagaccaag    17400
cgacgcattt cctttaaaga cagtaaaatg gtggagttac ataaatatgc aattattaaa    17460
acagcttttt aagaagaaat ttgtaaaaga agaacacgat aagaaaaccg gtcaagaggg    17520
tatgacatta ctcgaagtga tcatcgttct aggcattatg ggggtggttt cggcggggt    17580 tgttactctg gcgcagcgtg cgattgattc gcagaatatg accaaggccg cgcaaagtct    17640
caatagtatc caagttgcac tgacacagac ataccgtggt ctaggtaatt atccagcaac    17700
agctgatgcg acagctgcta gtaagctaac ttcaggcttg gttagtttag gtaaaatatc    17760
atccgatgag gcaaaaaacc cattcattgg tacaaatatg aatatttttt catttccgcg    17820
taatgcagca gctaataaag catttgcaat ttcagtggat ggtctgacac aggctcaatg    17880
caagacactt attaccagtg tcggtgatat gttcccatat attgcaatca agctggtgg    17940 cgcagtagca cttgcagatc taggtgattt tgagaattct gcagcagcgg ctgagacagg    18000
cgttggtgtg atcaaatcta tcgctcccgc tagtaagaat ttagatctaa cgaacatcac    18060
tcacgttgag aaattatgta aaggtactgc tccattcggc gttgcatttg gtaacagcta    18120
attcaaataa gtttgtttaa cttaatctta acgttgccca ttaaataatg ggcaacttat    18180
taaattcaat gtggtatcaa tatgagaaaa taccaacaag gtgtcggatt attggaggcg    18240
```

```
attctggctt ctgccgtatt agggatggca ttggtcgctg ctgggagcta ttacaagcgg    18300
gaagctgaac tcatgattaa atccagtaac gcatttgatg ttattgagtt gtcatctcaa    18360
atccagcgtt acgcctcttt aagtaaaatt aataatcgta ctaacccaat actcaaagat    18420
aataaggcaa aagaatttaa agatgcggat ttgaaatggt taaagcttga aaactgcccc    18480
acagcaggtg atgtaccgac aacgggtaat aataatgatt tacaagatca gtttattgct    18540
tgtgatgcag attataggaa aggtgatcta agctattttg ggagtcagtt tgaattctca    18600
acctatgtac atccttccaa cccggaaatt caacgacaaa taaaacaagt cgtcagctat    18660
tttcaatatc gaggcatgga aagagcgttt attggcgatg ctgcgggtta tgttatcagt    18720
gaggccaaga aaaaggatt tagcgcacaa gactatcgaa tcgttctaat agaacctgat    18780
cgtgtcgggt attttgagtc aaatgctatt agctatgaag aatttataga aaatccatcc    18840
gctcgcgaaa attttctttt aaaagcgacg aaagatagaa ctctggcgtt ggcggtcagt    18900
cttgctcaaa ccggagaaat agcaatgcaa cgtgatggtt ccgttgcatt tttagaagat    18960
agtgagttgt gttgggatac ggcggcaggt agtgcaaagt cttgtctctc ggttcggtac    19020
gataccgttg gaaataaaac agaactggat ttaaaacaga tagatgtggt cagtgcgaaa    19080
ggcctatcat ttgaaagtga tggtaaaaca aaaacaccag tggtttcgac ttatgagact    19140
tttcaagatg gtgggcgggc taaaaccatt aacgctattg aatgcccaac aggtttaaat    19200
aatcgttttg ccgcggtggt gagttcattt tcaactgctg gacagaatgc aaactttagt    19260
tcagagagtg ctaaggattc tcaaggcaca acccaaaagg atggtagcaa aggaccgcat    19320
gcgcttctat ccggtatatc actgaactgg acattaacga ataaggtatg ggatgtaacc    19380
gcctcgattg gtatcgagtc cggtatattg cctacttcag gtatcgattc tggatcgtta    19440
ttacgaaacc ctaaatcatt gtcttttata gcgtttcaat ggtgtgaaaa ttaatgaaaa    19500
aaaactatta cataggtgca tgcatcgcgc tcatattaag cgggccaacc tttgcacaag    19560
gagagatgca caaacaaat gagcagattg cagaacagtc ctcagttgat ttaatcgcag    19620
aaatttatca ttcagatcga tatgcagaaa cgtttattga atccgaagag ttcgaacaag    19680
aagaaagcac gtcaaaagaa ccaatcttgt ttgtgacacc ttatgatcaa ttaaaagata    19740
aattggaatc ttgggctgat ttacacggtt atgttgtgaa atggaataca cagaaaacgg    19800
ttcagttcga taatgctgtg gcttatgaag gagactttga acaagtttta actgagttgg    19860
ctagcgatat taaccaaatt ggcatagaca ttaactttaa aatatttcaa aaaaataaag    19920
ttattgtcgt ctattcagtg agataagtat gaaaaaaaca ataatcagta cacttgttat    19980
cggtttggtt gccggttgtt ctaatacgaa cttgctaaaa gacaatctgg ctagcgagca    20040
aaatgtcatc aacttaagta agtcttcaaa cgaagcgaaa tctagaaata ttgaatttct    20100
ctctggtgcc tatttaagtg agagaaaagt gccgaagcat gacattaagt tcagtggtaa    20160
gtatgttgag tttgaaagta aatcaccgat tgagttaatc gatgttcttg atggactttc    20220
taagcaatat aatattcagt atgtattctc agatgagtta aagatgaaa agtcggaaga    20280 gaataaaaag tcatcaggct catcatcggc gaagaaaata aaatactcag gacctctggc    20340
tggttttttt gattatttaa gtagtgcata taacatgcac tttgaatttg gtcataataa    20400
cttagttaag gcatatcatt ataaaaatca gttttttaac ctccagcaat actttgatga    20460
taataaattt agctcgtcaa tgcagattgg gggtaccagt ggcacatcaa gtggtctaaa    20520
aggtactgca gataccgcta tagaatctaa tagttggaaa aaaatcgatg agttttaag     20580 tgcatcctta ggtgaaactg gaaaatttac aattttgaa gattattcac tagttacagt     20640
```

```
aaaagcccga cctgataagt ttttattgtt acatactttc tttgacaagt tgatcaatga    20700
gagcaagatg caaatcgcgg ttgattatag agtggtttct cttagtgaag aacgcttaaa    20760
tcagttagct gccaaatttg gtattgaaaa tgcagggaaa tacagtatta ccagtgatat    20820
ggtcgatgcg atctctttaa gtcaagtagg gggggattaa ggcgcttcat atcgctctgc    20880
ctcagcaaga ttagatgcag tggttaatga gttatcacag gaagtaatgc atgaggggca    20940
ttttatcggt atccctaaca gagtaatgcc actaaatgtc actacaaact cgaagtatat    21000
atcctcaatc gaaacaacaa aagataccaa tactgatgag gaaacgagaa ctgtcaaagt    21060
ttctgactta gtaacaggtt ttagcatgat ggttatgccg aaaatcttag atgatggacg    21120
aattcaaata tcgtctggct tttcaagaaa acagttagtg tctattggta ctgcacaagg    21180
tattactcta ccaacagttg atgaaaatga atcaatgaat accgtaacga tgaatcctgg    21240
tgaagtacgc ctagcaatgc tatttaagga taattacatt cagaatagta atggtgttca    21300
attattaggt ggtggtactg aaaataagaa atcggctcgt tatattgctg tgcttgttgg    21360
tgcaagcagt tacaaaacca atgatcttgc tagtaataga gtaaatatat atgactagca    21420
tatggttaca tgagtcagat tttagatatg ttaacttaga tgtagaaaga taccaaaaaa    21480
aatatcgttt gacattgact aatggaaata agtacgtatt tattaaagat aaagaagata    21540
tatctgatgt taatccattt atcccttata ttctcatgga agaaggaatg aataatgtat    21600
tagtaaaatc agatgattac aaagatatcc tcatttatca aggcgtcaat attcaatgtc    21660 tggatttttct taatgataat gatatatccg ttgagaaatt agttgatttt gaaacagtag    21720
aacttaaagc agatgagcta aataaaataa aagcacgaag gttggatgca caactgattg    21780
aagatgaagt caaaaataat aaagtgttta ttattggatt cattgctatt gtaataatta    21840
gtatcggcgt atttttggtta atgtgattat gaagattagc agtttgaaga agggaagcaa    21900
tttcagtatt aatataaaaa atataaagct tgataaaaaa ttgttagtgg caattatttt    21960
tttagtttta tcaatactgg gaggtggagc ctatttatac tatgaaaatg agaaaacgaa    22020
aaagttagag caggcaagat tacagaaaat tcaaaaagag aactctgaca aacaaaccta    22080
tttgtcagat tttaaatcgg cttttgaagg tcttgattac caagcgctaa ctggttttta    22140
tgatgtactc agatctgata tcgatttttt cagggtaaat aattggttat tagatgtaat    22200
ggactgtaat gttaactgta atttagcctt taaacgagga agctttgaca cctttactta    22260
tttagaaatg aatcgaaatg gagctgttat aaaaccacag ttcgaccaga ataagctcca    22320
gtttgcaaat gtggattata tatctggttt tcgttctatt tatctcaaag atctcactga    22380
gcaagagaga gataagagtg aaaatatcat tgaacagtgc tcaacaaaac tttctgaact    22440
gtataatttg cagttgttaa tgaaagaaca ggtgaaattt aaaataaatc ttcctaggaa    22500
tgtaacttca atatcgggtt atgactgggt aaaaaatagt gacattaaat tcggttctat    22560
tgaaattgaa aatatgccag agaaaaactt gggtctgatg aaaaatatta tgaataatag    22620
tatgatgatt acgtctatct cttttgcaaaa ttcaagtttt aaatccaagt taaattatta    22680
ctgctattaa ggtgggatta gagaaatgaa tatcaaacta tcatttattt caattgcttt    22740
tctatcgtta agttttaatg ttgctgctaa cgaatttgaa aaatctcaag agcactacaa    22800
aagtgtaact gatttaaaaa acaaaatcga aatactagag ttagaaaaga aataacagaa    22860
gctgagtggc gagattcgca atgcaagaat gccaaaaata gataagtctg cacccgtttt    22920
atctcctcag cctgtagtaa aatcgtcaga agaattacaa aaaagtatcg aacatataga    22980
agaagagctc aaagtggaat tggcttattt ggttaacaat ggtcaacaaa aaaaatatac    23040
```

```
attcaatctt aatggcaaac ttatcacatt ggttaatggt gattttgtaa atggttggaa   23100
attcattgaa gaccaaaata aaattcaatt tttcaagggc aataaggtaa tcgatgtcaa   23160
ttgatataaa gtatttaagt cgtattgata tagatcgtga ggagttttc tttaaagact    23220 cgagattaat gtgtaagaaa ttcgatgaag agcgtgaggt attaactctt ctcgaattcg   23280
atacaaaatt tcgggtcaat cttctgaaga aagataaagt ttataagtat ttcttagttt   23340
cagatgcaaa tcataaatta ttaatagcga atcttgttac cgagcagcaa gctaaagact   23400
taagttttat agaaaagat ataatgaaaa ttgcatcatc tgctacagct tatggtgcaa    23460
gtgacatcca cttcatccga gaggatagga tttgtaaaat aaaattccgt gtgaatggca   23520
caatgatcga ctatagagaa atattaagtt cagaagccga ttcgctaatg tttgttctat   23580
acaatgtgat ggcaacaacg aaagaaacga cgtggaaccg aaaactacct caagatgcaa   23640
atattattct tgtgatcaac gaaaaggcat atcgctttcg ttacgcacat atgcctttat   23700
ttggtgaggg agggaaaaac tatcatgcgg tagttcgtat tatctatcct tcaaataatt   23760
ttgtttgtac aaactatcaa gatattgggt ataacgaggc tgataccgat gcgattgcaa   23820
gaattctaaa tacatcttat ggattgttca ttgtttccgg aacaacaggt tctggtaaat   23880
caacatcttt gaaaaagtat atagaattac ttttctttaa taaatataag ggaaaaggat   23940
gttttgtcac cgttgaagat cctgtcgagt atttaatttc tggagcacag caaagctcaa   24000
ttgttgccga taatgatgat aaaacaaaga acccatttgc tgatgcggta cgttcagcga   24060
tgcgtcgaga tccggacgtt attatgatcg gtgaaattcg tgataaacct accgttgagg   24120
ctctatcaag tgctgtagaa agtggccact attgtcttac gaccatccat gcaggttctg   24180
ttgtttctgt tttacaaaga cttttcaggat tagggatgaa ggctgacaaa atagcatcac   24240
ctggatttct ggctggtatt acaagtcaga aattaattcc cgaactttgc ccaagttgta   24300
aagtttcctt tgttgatgaa cgttatcagc gtgctgtatt tagcgcgaat gaaaatggct   24360
gtgaggcatg taatcattct gggtttaaag gaaggctgct tttattagaa acattagtcc   24420
caacagttga agatttagag ctagtggcga gtgaaaactg ggtttcct tatcgtaaat     24480 atcgggagcg acgctttata aaaactggaa aaaaggtct tggtgaaggc ttcagcatta    24540
aagataaagc ttattacaat gttttaaaag gtaaagtgtg tcacgaatat tttatgctgc   24600
atttcggtca gttagatcat gaggatgaaa atataatata tgaaaattat ctccaagaag   24660
tataggctag aactttattc aatgcttgtg gacttattga atgataatat cccactctat   24720
gatgcattaa ataaaataca aaatgaggga gtgggcatct atgataagaa ttttattaaa   24780
tccattgaat taattaagga taggatgaaa agtaattcat cactaacgga tgccttaact   24840
ggactaatac cagataaaga agttttgatg attaatgttg cagaaaactc aggtaagatt   24900
tcgagtggta ttgctgcaat acgcaaaaac attatcgatg cagatgagat caaatctaaa   24960
gctatctcat ctatgatcac gcctagcgtg atgcttatcg tgactatggt tgttattgct   25020
ggctattcag taaaagtatt tcccacattt gagtctgtac ttcctgtgag ccggtggccc   25080
ggtgttaccc aagcactta taaccttgga ttttcattgt atgaaggctt gtggatcaaa    25140
gttcttattt ttgtcgctat cttcattacg attttagttt ttatgtctaa aaacattaca   25200
gggaatttca gagatggttt tttagataag ctgccacctt ttaattttgt aaagcatatt   25260
gcagcaacag aattttttggc caatatgtcc atgttgctag atagtcgagt cccatttaaa   25320
gaaggtctgg acattgtcga tcataaaacg acacgctggc tctcctcaca tttgcaaaga   25380
atgaaagcta acatgcaaga agggctagac tacaaacagg ctctcgacac caatttacta   25440
```

```
gataaaaaaa tgctcctgac aatggctgtt tattcagaac tacctaattt ttcggatgta    25500
atgcaaaaat tagctattga agccaatata aatctacata aaaaaattgc cactttagca    25560
ggggtaatga aaatatttc actaataacg ttggcgttgt ctgtgatttg gatcttcggt    25620
gcgatctttt cgctcgttga taaactaagt tcatctttat agtgaggata tatgagatat    25680
aaaaaaacct taatgttatc aatcatgatt acatcattta actcatttgc atttaatgat    25740
aattatagtt caaccagtac ggtttatgct acgtctaatg aagctacgga ttcaaggggg    25800
agtgagcacc ttagataccc ttatttagag tgtatcaaaa tcggtatgag tagagattat    25860
cttgaaaact gtgtgaaagt atcttttcca acctctcaag atatgtttta tgacgcatac    25920
ccatcgacag aatctgacgg tgctaagaca agaacaaaag aagatttctc tgctcggctt    25980
ttagctggtg attatgatag tttacagaaa ttgtatatag atttttatct tgctcaaacg    26040
actttcgatt gggaaatacc gacaagggat caaattgaga cactagttaa ttatgctaat    26100
gaaggtaaat tgtctacggc acttaatcaa gagtatatta caggtcgatt tcttacaaaa    26160
gaaaatggtc gatatgatat tgtgaatgtt ggtggtgttc cagataatac tccagttaaa    26220
ctaccagcta ttgtttctaa acgcggacta atgggtacaa cttctgtagt taatgcaatt    26280
cccaatgaaa tttatcctca tatcaaagtt tatgaaggga ctcttagtcg tttaaaacct    26340
ggtggtgcaa tgatcgcagt attagaatat gacgtaaatg aattaagtaa gcacgggtat    26400
accaatctgt gggatgtgca gtttaaggtt cttgttggag ttccacatgc agaaacagga    26460
gttatctatg accctgttta tgaagaaact gtcaaaccat atcagcctag taacaactta    26520
acgggtaaga agttgtataa tgtatctaca aatgacatgc ataatggtta caagtggtca    26580
aatactatgt tctcaaattc taattataaa acgcaaatat tattaactaa aggagatgga    26640
agtggtgtga aactgtatag caaagcatat tcagagaact ttaaataaaa tagataagat    26700
aacagccaca ttcgtggctg ttatcttatc tcaaaaaaca taaataaca tgagttactt    26760 tatgttttc ttatgtaata cgtctgtaac ttgttcttat gtctgttatg tagttttata    26820
ttaacttcga ttttaagata actttacgtg gatggctctc tgcgtttatt tatatatctt    26880
cagagtagaa cgca atg att ggg aaa aaa tct ttt caa act aat gta tat       26930
              Met Ile Gly Lys Lys Ser Phe Gln Thr Asn Val Tyr
                1               5                  10 aga atg agt aaa ttt gat act tac ata ttc aat aac tta tat ata aac       26978
Arg Met Ser Lys Phe Asp Thr Tyr Ile Phe Asn Asn Leu Tyr Ile Asn
         15                  20                  25 gac tac aaa atg ttc tgg ata gat agt gga att gca aag ctt ata gat       27026
Asp Tyr Lys Met Phe Trp Ile Asp Ser Gly Ile Ala Lys Leu Ile Asp
     30                  35                  40 aaa aat tgc ttg gtt agt tat gag ata aat tca agt tca att atc tta       27074
Lys Asn Cys Leu Val Ser Tyr Glu Ile Asn Ser Ser Ser Ile Ile Leu
 45                  50                  55                  60 ctc aag aaa aac tct att cag cga ttt tct ttg act tca tta tca gat       27122
Leu Lys Lys Asn Ser Ile Gln Arg Phe Ser Leu Thr Ser Leu Ser Asp
                 65                  70                  75 gaa aat ata aat gtt tct gta att aca ata agt gat tca ttt ata cgt       27170
Glu Asn Ile Asn Val Ser Val Ile Thr Ile Ser Asp Ser Phe Ile Arg
             80                  85                  90 tca cta aaa tct tac att ctt ggt gat ctc atg ata agg aat tta tat       27218
Ser Leu Lys Ser Tyr Ile Leu Gly Asp Leu Met Ile Arg Asn Leu Tyr
         95                 100                 105 agt gaa aat aaa gat cta tta ctt tgg aat tgt gaa cat aat gat ata       27266
Ser Glu Asn Lys Asp Leu Leu Leu Trp Asn Cys Glu His Asn Asp Ile
    110                 115                 120
```

```
gct gtc ctt tct gaa gtg gta aat ggt ttc aga gaa att aat tat tca    27314
Ala Val Leu Ser Glu Val Val Asn Gly Phe Arg Glu Ile Asn Tyr Ser
125             130                 135                 140 gat gag ttc cta aaa gtt ttt ttt tca ggg ttc ttc tcg aaa gta gaa    27362
Asp Glu Phe Leu Lys Val Phe Phe Ser Gly Phe Phe Ser Lys Val Glu
                145                 150                 155 aaa aaa tat aac tct ata ttt att act gat gat ctt gat gct atg gag    27410
Lys Lys Tyr Asn Ser Ile Phe Ile Thr Asp Asp Leu Asp Ala Met Glu
160                 165                 170 aaa att tca tgt tta gta aaa agt gat att acg cgt aat tgg cgt tgg    27458
Lys Ile Ser Cys Leu Val Lys Ser Asp Ile Thr Arg Asn Trp Arg Trp
        175                 180                 185 gca gat att tgt ggt gaa tta aga acg aat cgg atg att ttg aaa aaa    27506
Ala Asp Ile Cys Gly Glu Leu Arg Thr Asn Arg Met Ile Leu Lys Lys
190                 195                 200 gaa cta gag tct cga gga gta aag ttt aga gaa tta att aat agc att    27554
Glu Leu Glu Ser Arg Gly Val Lys Phe Arg Glu Leu Ile Asn Ser Ile
205             210                 215                 220 cga ata tca tat tca att tca cta atg aaa acc ggt gaa ttc aaa ata    27602
Arg Ile Ser Tyr Ser Ile Ser Leu Met Lys Thr Gly Glu Phe Lys Ile
                225                 230                 235 aaa cag att gca tat cag tct ggg ttt gct agc gtt tca tat ttt tct    27650
Lys Gln Ile Ala Tyr Gln Ser Gly Phe Ala Ser Val Ser Tyr Phe Ser
                240                 245                 250 aca gta ttt aag tca acc atg aat gta gca cca agt gaa tat tta ttt    27698
Thr Val Phe Lys Ser Thr Met Asn Val Ala Pro Ser Glu Tyr Leu Phe
            255                 260                 265 atg ttg aca gga gtt gca gaa aaa taa tggaatacgt ttacttgatc          27745
Met Leu Thr Gly Val Ala Glu Lys
            270                 275 ctattttcga ttgtatcact gattttgggt agttttagta atgttgtgat ttatcgtcta    27805
ccaagaaaaa ttttactaaa gaatcatttt ttttatgaca tcgattcaaa tcgttccatg    27865
tgccctaaat gtggaaataa aatcagttgg tatgataatg ttccattgtt aagttatttg    27925
ttacttcatg gtaagtgtag acattgtgat gaaaaaattt cattaagtta ttttattgtc    27985
gagttatcat tttttataat cgcatttcca atatattggt tatcaactga ctgggttgat    28045
tcgttcgtat tgctcgggct ttactttatt ttattcaatc ttttttgtaat tgattttaaa    28105 tctatgctat tgccaaattt acttacgtat ccgatattca tgttggcatt tatttatgtg    28165
cagcaaaatc cagcattaac agttgaaagc tctattattg gtggttttgc ggctttcatc    28225
atatcctatg tgagtaattt cattgttcgg ttattcaaaa gaatcgatgt gatgggaggt    28285
ggagatataa agctctatac tgcgattggt actcttatcg gtgttgagtt tgtaccatat    28345
ttattcttgc tgtcctcgat tattgcattt attcattggt tttttgctag agtctcatgt    28405
cggtattgct tatatatccc tcttggacca agcattatta tctcttttgt aattgttttt    28465
ttttcaatcc gttaatgtg agctaaaatg aagttttcta tcaagttact aatgattttt    28525
acatcaatta taattactat ttcatctatc cttacttact ttcagatgca tggaaccaat    28585
gaatatcttg atcgtacgat aaaagatact atttctgaaa cgctagactc tttggaagat    28645
aaaataaatc tttctattga gtccaaggtc gatgtgtcaa aatctgttat cgacatttat    28705
gaaaatttac tggaggggga atcccctctc agtaaattta aggatgttga tgtcaatcat    28765
ctttcaaatg ttttttcaatt gttcggatat gctgatgaaa gaacaggaga gatcattact    28825
aatgacccaa actttaaagt gcctacagga ttcgatccaa ggactcgatc gtggtattta    28885
aatgcaaaaa aattgaatac ctttagtttg tctgagccgt atgtcgatct cattacagag    28945
```

```
aagttaatgg tgacaacaag tgcaccaata tataataaaa acgatttaac aggagttata    29005
ttttttgata taccactaga tgacgttcag gaattaatta aaagctacaa tccatttgat    29065
gccggcacga tttttatcgt tgataacagt gggaaaataa ttttcggtaa taaaaatgat    29125
atatcgggta aaaatttatt tggagacttt gatagcttcc ctctatcggt aagtgagtca    29185
aaaacgaaag ataaaaatgg ggtaaattac gatgtattca tcaaaatgtc agactttggc    29245
gattggaatc ttgtttctat tatcgaccat gataaagcac gctctgatat tatcacgttg    29305
agaaacaata gtatatttac tgccgtcatt ttagcaagtg ttttctttgc tatcttgttg    29365
tttactatgc ggttaatgct gaagccattg catcaattaa ccgatgcaat ggtaaatatt    29425
tcatcgggca gtgctgatct tacggttcgt atcccgaata gtacggatca agagttttca    29485
aaaataataa attcctttaa cattttttgtt ggtaatctgc aatctattgt gtcggaggtt    29545
aaaatgaact cagaaaaaat aaattgcata actactgaaa cacaagagct agtcgaagtt    29605
tgcaataata gcgtagctga tcagtatcgt gaacttgata tgctagctag ctcaatgaat    29665
gagatggtgg caacatctaa tcagattgca caaattacat ccgaagcatc agagatcaca    29725
tctaagatta acgtcaagt gaatgaagga gtcggtgctg tttcttctgt taccgaaagt    29785
gtaggtaatt tagttgagaa gttggataag acgaaatctg ttatccaaga tcttaatcgc    29845
caaactcaaa atatagatgt tattttgaag gctattaatg atattgctga ccaaacaaac    29905
cttcttgctc ttaatgctgc aattgaggct gcacgagctg gggaaaatgg acgaggtttt    29965
gctgtggttg ctgatgaggt acgcagccta gcaataaaga cacaagagtc tactaaaaat    30025
ataggaagta ttatccatat attacaagaa aactctttgc tatccgttca tgttatggat    30085
gaaagtttta atattgcctc tgaaactatg actatatcag ctgattcaaa acaatgttta    30145
gacaatatta gtcaatcagt aatacaaatt gttgatatca caaatcaagt agctacagct    30205
gcttacgaac aaagtcacgt atcagaggaa ataaacagca actctatttc tataaaaagat   30265 aaagcagata cctt atcaag tttgggtaat aagatttctc aacaggctta ttctcaaaaa    30325
gcactgattg gtcatcaaga tgatttaatc agtaagttta tcatttaata tggatgtatt    30385
tcatgaaaag taagaatcga ttttattaa tttctttact atcatttttct acgagtgttt    30445 ttgcggatgt taatctttat ggacctggtg gtccacatgt gccattgatt aaagttgcag    30505
aaagttttga aaaatcacaa tcaaaacgcg ttaatattac ttttggacct caagctactt    30565
ggaatgacaa agcaaaaaaa aatgctgata ttttattcgg tgcatcagaa cattctgctc    30625
tagctattgc agaaggacat agtgaaagat tttcaaaatt taatattcat cctgtattca    30685
tgcgtgaagc aattatctta gtaaaaaaag gtaatccgaa aaatattaag ggtatggctg    30745
atcttttgaa gcctggtatc ggaatcgtcg taaatgatgg agcaggtgta agtaatacat    30805
cgggcactgc tgtttgggaa gattcagttg gtagaatgaa aaatgttgag aaactccagg    30865
catttagatc taatattcac gttttttgccc caaatagtgg atcagcgcgt aaggcgtttg    30925
ttgatggtga agatattgat gcatggatta catgggtcga ttgggccata gctaatccaa    30985
caatcggcga tatggttaga atggaggatg aatatcgtat ttatcgtgac ttcaacgttg    31045
ttcttgccaa aaatccatct agtgaagcga ttgactttt tgattatcta acaaaaagca    31105
aagacgctga agcaatcttt cagcactatg gctggtttaa gtgattttag ggagagtaca    31165
tgtactctcc tatgaaattt ttcgtaggaa ctaatatgaa tcaaagagtt agtgttattt    31225
atgctacttt ctgggataga ctatgggcat cattgattga tagtttagtg ctatcggtat    31285
taattctagc tgtcattttg tttatatttta atgtctttga tgtggatgtt gcaataaaca    31345
```

```
gtagatacgt cgatatcgct aatttatctt tatcactttg cattactatt ttatttggga   31405
attttaaatc tgcaacacct ggcaagatgc tcttaaaatt aaaagttgtt gatgagcata   31465
ctcttaataa gttgacattt aagcaatcta taattcgtta tttgtcatat tatattagtc   31525
tgttaggctt tttcatcggc ttttttctgga ttttctttaa caaaaaaaat caaggatggc   31585
atgataaaat cgcaaagacc atcgtaataa aattgccatc tagtactcag taatatttaa   31645
aatgaataag acacttagga ttacattatt atctatatct ggttcaaaaa catttaacat   31705
aaaattcaga catagagtgt ttttacattt gacttttgt tttattatgt tgttttttt     31765 ggcaatagct atgttgattt ttaattttga catgaaattg agttcctctc ttctaagtca   31825
gataaaaaat gaatataaga ccttttttctt agagaacaaa atatcatcaa ttaacagttc   31885
ttcatctgaa ctaatggaag atttgttttc aaagcaagag cgttacgagt tagctatcaa   31945
tcgtttagaa agattagaat cttttgtaca tagcgctgaa tcgatcgata tggtgactgt   32005
tacagagcaa cttggtagct atatgaaaga aactgtgttg aatgagattc ctaatggctt   32065
tcctattcct gatgcaaaga tatcatctcg ctatggtgaa cgtgtgcatc cagttaccaa   32125
agttaagcag attcaccatg gaattgattt ccctgctgct attggcacac caatctattc   32185
accagcagat ggtgttgttg aagcgataag agtcagtacc cagggttcag gtaattttat   32245
gcgtcttcag catacttatg gatttagtag tagttactct catttgcata agttctcggt   32305
taaagagggg gattttgtca aaaaggtga attaattgcg tactcaggaa atactgggtt    32365
atcctctggg ccacacctac actatgaaat ccgtttcctc ggtaaatccc tagaccctca   32425 cccattttata aaatggaatt acgataattt ttctgaaatt actaataaag taccattaat   32485
caaatgggat gaattgctga ctaacattga gatccggatt gcaatgaatc cgaatctcaa   32545
tgcacaataa gactagaagt agtactttga atttaaactt atagaaagca catcattgta   32605
cttatcgaac tgatatctta actctgttcc aacgctaagc tctggaatta aattataatc   32665
caaccctaac gaaaatagtg caccaaagcg attctttta agacctgttt ctaatagagc    32725
ttttctaatc tctatatcat catttaggag taattctagc tcttcatatt ttccagaata   32785
tgcttcatat tgtgtatgtg tcacaccaac ttttatattt gttttcaatt gctgatgaat   32845
ggggtatgag taaactgaga ttaatgcaag ttgtttagct tcaatctcag agctccattc   32905
gtgctctttt ctatattgtt gattatttaa agattcaatt cctataaact tactgtattg   32965
atcttctaat ttataacttg aatagttgat ttcaaaagaa aaattatcat taaatttata   33025
accaattagt ccacctaaaa acatatcttc catattgggg tttaggctaa cagcgtcact   33085
ttgatagttc gtctcaaagc tatgatttgc tgttccaatt ccaagttcaa gaccaatata   33145
cggtgctgca tttgctgata aagtcgtaaa caaaaaaatt gctgataaag ttttttgcat   33205
tttttactcc tatttttacc tgtgtttcac attttattct aactttaatt ttttattttt   33265
tttatgctaa ctcgttaaat ttttaaaaat aaatttaaca aaatgtataa agcgattttt   33325
ttcattttta acaaggataa ttaattcttg ttttttgttt aataggctta agatgaagat   33385
tcgtattgta tcattgatag ttttgggttt tcttataggt tgtaagcatg aaagtataat   33445 taccccctact gtgcctgctg atggttcggg tggtaacgca ctaaatcctg gtttggtagg   33505
tggttatttg ccagatattg gtgttccgga tcccattatc tcgctatcca tgactttaga   33565
tggtaacttg aaatttgata gttctttact gtgtaatgat caagatgcct ctcatatttc   33625
aaatatcaca aaaagataat gtcttttgta cgatcaacgg gcgttcaatc gcaacattta   33685
ccgctccctt tgacgctaat aaaaatggcc gtaacactga ttctgaagtt ttatcttaa    33745
```

```
tctctgcgga tgagtaccgg gactcgccag ttcgacagga aaatctccaa attttaatga   33805
aaaatatggc gacaatacat ggagataaaa tatctctagt tttccgaagt actcttgatg   33865
ccttgacatt cgaaaattat ttacggcaca atttagatct tcccaaagac caattttag    33925 aagcaattac agaaaaaatc gccaatgata atcaggtcga taagcaacct tcaactcatg   33985
tgcctaatat ctctccatca ttcacgcctg ggacttcatc taatttgaat agtccattcg   34045
tttctgctaa tgctgaagag tctttgagct atataccgac agatgttatt ccttcgcttg   34105
gtcgcttact tgatagtcaa ggtcgagtta ttaatggtgt ttcatacttc agtaataata   34165
ctcgtggtat tactggtgta gataaaacag gggctatttt aaatgatggt tcatttgaat   34225
tttcgtgggg agatattatt agcttttcaa tcgatacatt tgaattaggt agtactcgag   34285
ctaataaaac tgattttat atcagtgaat taggtaagga caatgagggt aagaatgctg     34345
aagctttgat tcatcgttat gcaagtattg atgattctaa gcttatcatt ccagataaag   34405
ttacgcagat ttttcccta tacctaatg tcattaatga agtgatttca ttatcattac      34465
ctaatggcga tatcgaactt gatattggag atggtaaaac tcagattgta cctggtgaat   34525
tctttaagca gtttgattct ggattagcag cacttatcga tcaatctatt tcacctatat   34585
cgaggttcaa atttgaagac agtttgccta agaaaaagtc agcaattgat tctgaatctt   34645
cacaaatcca agatattatt aataaactct ggggtgcaac cgataccgta caagctaatg   34705
gatggaaaaa agtcgatcgt tttcatattt ttcatgacag tacaaacttc tacggtagta   34765
caggaagtgc ccgagcacaa gcagcggtga atattgctaa tagtgcattt ccagtcttaa   34825
tggctcgtaa tgacaataat tactggattg attttggtaa acctaaagca tgggattcga   34885
atagtctggc attattact gaagcacctt ctacagttgt gcctgataaa gtatctgaag     34945
atacatcaac ctttaattta cctttttatta gtttgggcga aattggtaaa ggcaagctga   35005
tggtactagg aaatgcgcga tataacagtg tcttagtctg tcctaatgga tttagttggg   35065
gcggaactgt taaaaatggt acttgtagct taagtagtga tcgtgatgat atggctaatt   35125
tttttagtaa tgtcatccgc tatcttacgg gaagtacttc caatgatgtt attgttggaa   35185
ctaatattcc agaagtttac tttaaatcat ctggccaaac tatggggtca aaagccaatt   35245
ttgaactcga ttcaagattc tctaagcaaa ctcaacagtt gactagtttc catgatttag   35305
atgttaatac tatacctctt attattatca atgcatacga ctataaagga aaaaacataa   35365
atagtccgta tgatattcca ttaagtgctg atgtaggcag tccgaaattg tctcgttctg   35425
atgtcactga tttaattgat tatataaaca acggtggtag tgtattaatg atggagacta   35485
tcattaatac aaataacagt gagatttctc gtttattgga cagtgctggt attgcttttg   35545
gcattggaaa cagtgtagtt gctgacggta atggcccgag tggaggccac ccagatcgcc   35605
cacgtagtca gcgagagcac ggtatttggg ttattgagcg atatgcagct gttgaagacg   35665
agtcttctgg tcaacagacg ctaccttatg tgattaatag tgatggttca attgagtgga   35725
agtatattgt agagaatagg cccgatgata aacctaaact tgaagtcgcg agttgggttg   35785
aatctgaagc tggagataaa ttaattactc actatgcatt tattgatgag tctcagcact   35845
ggaaaaaaga tatttcaggt aaaataatct ataacgtggc agggaagccg gaagtagata   35905
atgcatcatt atctttggct aaaaataaag tacttgatgc tttttaaaaac agtagtggcc   35965 agagagccta ctctgaatgt aaaaattctg agtttcatta tgagattaat tgcttagaat   36025
atcgtccagg taattcaatt cctattactg gtggtttgta tgtacccga tatactgata    36085 ttaagttagg agagtctgaa gccaatgcta tggtaaaggc ggctaatctt ggtacaaata   36145
```

```
ttcatgcttt atatcagcat gaacgttatt tccgaactaa aggaaagtcg ggagcccgtt   36205
taaatagtgt tgatttgaat cgaatttatc aaaatatgtc agtatggctt tggaacgacc   36265
ttgattatcg ttatgatgat aagcaatccg atgagcttgg atttaaagtt tttacacagt   36325
atttgaattg ttacactagt aacaacgctg gtggtaatac aacttgccca gaagaattga   36385 agatgaact tactcagcta ggtatgattt atgacgaaaa atcaggaagc tatgcaggtc    36445
aaatggatcc aagttaccca cttaattata tggaaaagcc actgacccgt taatgttag    36505 ggcgctcatt ctgggatctt gatatcaaag ttgatgtcag aaagtacccc ggtgaagtca   36565
caacaagatc aggtggaggg gatattactc ttgacatgcg taataatacg gcagcttggt   36625
ttgcgggtaa taggcagccg acagggcagt gggccgaagc tcatcagcct tttagtgttt   36685
cagtctcagg agaaacatcg cctgtcacca tcaccattgc attggctgat gatttaactg   36745
gccgagagaa gcatgagctt ggtttaaagc gtcctcctcg catgagcaaa tcatttgtta   36805
ttggcggcga tagtccgaaa atgcagactt ttaccgtacc ctatggtggg ttaatatatg   36865 cacaagggg aaattctcaa caggtcaaac taacattttc aggaactata gatgcaccgc    36925
tctatattga cggtaagtgg agaaaccctc ttttatctgg cgcaccaatt ggtgaagtag   36985
tgtcagacac cttcatattt actgcaccta aagcaaattt aaatgccgat ggttatttgg   37045
gggggatcga acagtttgca aaagatcttg atcaattctc agcggattta acgattttt    37105 atgcccgtga tgaaggtgcg gacggtgaca aaaatcgcaa agctactgat aagtcaatgc   37165
ctaataatcg tcaccatttc gtcaatgatg tcgcaataag tgttggtgct gcacactctg   37225
gctatccggt catgaatgat agttttatta ccagtagccg tagtttgaac actatgccgc   37285
tgaacagctg gctgcttggg catgaggtcg ggcataattc agcagaagct ccttttaatg   37345
ttgatggggc cacagaagtt gtaaacaact tacttgcctt atatatgcaa gatcgtcatc   37405
aaggaaaaat gtctcgtgta gaacaggata tccgttatgc tttcgatttt gttaatgctg   37465
agcatgggca tgcttgggga gccggtggtg ctggtgaacg tttagttatg tttgcgcaac   37525
ttaaagagtg ggcagaaact gagttttgata taaatgactg gtataatgat aagctacctg   37585
gtttttatat tgaagaaagc ggaataaaag gttggaactt gtttaaactg atgcatcggt   37645
taatgagaaa tgagaacgat gaccaaatca atatgaaggg agaaaatcaa tgtaagatat   37705
ctggtattgg taaaagtgat ctattaatgc tttgtgcatc atatgccgct cagacggatt   37765
tgtcagaatt ttttaaagca tggaatccgg gaagtaaggc atttctctat ccagatgatc   37825
ctcagccata ttacgaagga ggaataactc cttctgggat tcagagagtc aaatctttaa   37885
aattgaatct tccccaaaaa aatccccttt ctataaacag tgttacacaa cattagtaca   37945
gttattcccc ctagcttagc taggggatc tagtttgctt cctaacataa aatcctactc    38005 agatttatg ttaaatattt tttgtttcac tctcataaat taggaatgaa tagtttttat   38065
ttcatataga aaacaacatc tatatgttct ggagtattat atttgacgtc atatatatga   38125
tgaaaaacat ttagttacta ttgaatatcc taagggttaa tattgaggtt ggttacattg   38185
ctataataat attatagaga taggtttgtg tgtgtttttt taaaacaaaa aaaaggcgca   38245
ccgcagtgcg ccaaaaagtg cttaatcgtc agcttgtaac aatacatgag gtaaccgctc   38305
atgtatgttt atagtgccag tatcatagct gttatgaaag atgattttgt ttttttaag    38365 tggaaaatat ttttttaacg ctcttgtttc tatttaagct tatgaattta gtgatacgct   38425
gaacttggcc tctttaggct ttcactaagt gcaaatattt tcaccagcc atactgtaac    38485 atccatagct agattttct atgtgctcgc tttaccaacc catgagtttt cgacgtttct    38545
```

```
ctaaatagtc ggtacggttg tatgctttac ttatttgtat gagccaatgc gggttcaata   38605
acatcaggtt taaagccctg ttcattaaaa gtggtacttg ccaaagcccg aacaccgtgc   38665
gcgatcactc tatcttaaa tcctattcta ctaagtgatt tattggctgt ttctgtatta   38725
gtgggtacct ttggattgcg gctagatggg aaaatgaatg ttctatgacc aatgataggc   38785
ttaatcactt caagaataac caatgtttat gctgtcattg gcactacgtg ttcacggttc   38845
atcttcattt gctctttgga ttcatatact aagtgcaaag cttattaact ctgtcgattt   38905
attcccaacg agcgcctgag actttgctag gccgaaccat ggtgtgagtt tgccattcaa   38965
ttaaaaatcg cgtcacgtgc tggatattgt acatataaga taatgcattt catgcagttg   39025
tagcgcttta atatgtacaa ctttgtgttt tttaaacaca tcacggatcc ctgccaatgg   39085
gttggcatga atgacaccgc tattcaccac atagttaatg atttcattca taagttgggc   39145
agtgtgtttt acggtttcta gtaatccttg atactcaatt gggcgtcatg ttgcgatggc   39205
aatttgtgct gtaagtttac taacgggtat cgaactcaat ttgggaaagg aataaagttc   39265
aagttttctc caattacctt ccagtgtttc ttatatttgc ccttgtttac tagctttcca   39325
ctgttctaca acaaacttaa atgtcagtaa tggttttcgc cttttgttct tctttagcga   39385
gttgaggatc catgatatcc gctaactgtt tgcgatcctc aaggctttct ctcgagcttc   39445
tgccgaagag atatcgggat acgtaccagc agacgacagc actctaatgc ttctaaagtt   39505
ttgagtacaa atttgatgtc gtgaacgttg gctccgtcac tgacaacagc acgtggcgat   39565
ccattttcat ccgtcaacaa actgcgtttt acgtcttgtt ttactctgtc tgttgggttc   39625
ttgccttttt tgagctagct aaaggaacct tagtttggca gccatccatt aatatagaac   39685
gccaatcaat cctttgtta atcattccat tttgccaaat tagttcaaat acacttgcat   39745
ctcgacgctt ttgaaagcga cgatgtgcag agctagaggt aaaaatactc gccgcgttaa   39805
gcgtattcca ctgacaacca gttcttagaa caaaaagaat gccgttagga tcacatctgc   39865
ttccatgtgg ggggcggtgg aagtttattt ttcaattgct ttgtaccagt cacagatagg   39925
ctacctctgg ctgcctcttc tatatgctcg ctccaccagc acatcattgg ttttctgcgt   39985
tctaagtagt cagtgcggtt ataggcactg cgtacttggt tatcgtccac gtgagccaat   40045
gccgactcaa ccaagtctgg atcaaagcct tgttcgttga gtgtggtact cgctagagag   40105
cgcaaaccgt gactaaccag ccttccagca aaccccatac gtttcaatgc catatttgcc   40165
gtttggctgt tgcagggctt tttcggggct ctatccgacg gaaaaataaa atcacgatgg   40225
ccacttatcg gtttcattac ttccaatagc gccagcatct gctctgtgag cgggatgcgg   40285
tgttctcttc ttttttcat tctttcagca ggaatggtcc aaacctttc ttcccaatta   40345 atttcatccc aacgtgcacc agatgcttcc gctgggcgcg tcatggtgtg tagttgccac   40405
tcaagtaaac aacgggtagt gcgtttgata ctggcattag cgattgcgct catgagttcg   40465
ggcagttctg ctggtgtcag tgctgccatg ttttctttt ttggtttctt gaaggcggct   40525
ttgatgccag ttaatggatt ggcctggata agaccgcagt tagtggcgaa gttcatcact   40585
tcattgagtc gctgtgttaa acgtttgacg gtttctaggc tacctttggc ttcaatcggt   40645
ttgagtagtt ctatgatctc cggagcggtg atcgctttta ccggtttgtc ggaaatgtgc   40705
gggaagatat gtagctctaa tgaacgccag atatcaaggg cgtaatccgg tgtcacatca   40765
ttctgtttga tggcaaacca atcctttgtg acgttctcaa aggtgtgctc atggatctct   40825
ttatgtactt gttgttggcg ttttcgatcg tcttgtggat cgatgccttg tgcgatcagc   40885
tctttggcag aaagtaagct ttttcttgct tgtaaaaggg agatgtctgg gtacattcca   40945
```

```
aagcttaagt tagctcgttt accgtttgtg gggcgatagt agttgaagat ccactgcttt    41005
gaaccgttag gtttgattct aagtcgcaag ccatcaccat cgaaaagatt atattctttc    41065
tctctaggtt tggaggcttt gatctcttta tctgtcagct ttactgtgtt ttttgccatg    41125
atgggtacac cagattaaca cgataaaatc agtgtacctt gtagtgtacc taaaaatcaa    41185
agctgctatg gaatcttgtg gaatagctat gaatgctaag ttattgattt tttaattgtt    41245
ttatataaga aaaaagacgc ccggagacgt ctttaaacta tgatt                    41290
```

<210> SEQ ID NO 2
<211> LENGTH: 276
<212> TYPE: PRT
<213> ORGANISM: Vibrio cholerae
<400> SEQUENCE: 2

Met Ile Gly Lys Lys Ser Phe Gln Thr Asn Val Tyr Arg Met Ser Lys
1               5                   10                  15

Phe Asp Thr Tyr Ile Phe Asn Asn Leu Tyr Ile Asn Asp Tyr Lys Met
            20                  25                  30

Phe Trp Ile Asp Ser Gly Ile Ala Lys Leu Ile Asp Lys Asn Cys Leu
        35                  40                  45

Val Ser Tyr Glu Ile Asn Ser Ser Ile Ile Leu Leu Lys Lys Asn
    50                  55                  60

Ser Ile Gln Arg Phe Ser Leu Thr Ser Leu Ser Asp Glu Asn Ile Asn
65                  70                  75                  80

Val Ser Val Ile Thr Ile Ser Asp Ser Phe Ile Arg Ser Leu Lys Ser
                85                  90                  95

Tyr Ile Leu Gly Asp Leu Met Ile Arg Asn Leu Tyr Ser Glu Asn Lys
            100                 105                 110

Asp Leu Leu Leu Trp Asn Cys Glu His Asn Asp Ile Ala Val Leu Ser
        115                 120                 125

Glu Val Val Asn Gly Phe Arg Glu Ile Asn Tyr Ser Asp Glu Phe Leu
    130                 135                 140

Lys Val Phe Phe Ser Gly Phe Phe Ser Lys Val Glu Lys Lys Tyr Asn
145                 150                 155                 160

Ser Ile Phe Ile Thr Asp Asp Leu Asp Ala Met Glu Lys Ile Ser Cys
                165                 170                 175

Leu Val Lys Ser Asp Ile Thr Arg Asn Trp Arg Trp Ala Asp Ile Cys
            180                 185                 190

Gly Glu Leu Arg Thr Asn Arg Met Ile Leu Lys Glu Leu Glu Ser
        195                 200                 205

Arg Gly Val Lys Phe Arg Glu Leu Ile Asn Ser Ile Arg Ile Ser Tyr
    210                 215                 220

Ser Ile Ser Leu Met Lys Thr Gly Glu Phe Lys Ile Lys Gln Ile Ala
225                 230                 235                 240

Tyr Gln Ser Gly Phe Ala Ser Val Ser Tyr Phe Ser Thr Val Phe Lys
                245                 250                 255

Ser Thr Met Asn Val Ala Pro Ser Glu Tyr Leu Phe Met Leu Thr Gly
            260                 265                 270

Val Ala Glu Lys
        275

<210> SEQ ID NO 3
<211> LENGTH: 29
<212> TYPE: DNA
<213> ORGANISM: Artificial
<220> FEATURE:

-continued

<223> OTHER INFORMATION: Artificial primer

<400> SEQUENCE: 3
gcgaattcta tcatgagccg cctagatag                                    29

<210> SEQ ID NO 4
<211> LENGTH: 30
<212> TYPE: DNA
<213> ORGANISM: Artificial
<220> FEATURE:
<223> OTHER INFORMATION: Artificial primer

<400> SEQUENCE: 4
gcggatccgc atatttatgt aactccacca                                   30

<210> SEQ ID NO 5
<211> LENGTH: 29
<212> TYPE: DNA
<213> ORGANISM: Artificial
<220> FEATURE:
<223> OTHER INFORMATION: Artificial primer

<400> SEQUENCE: 5
gcagatcttc gtaaacaaaa aaattgctg                                    29

<210> SEQ ID NO 6
<211> LENGTH: 29
<212> TYPE: DNA
<213> ORGANISM: Artificial
<220> FEATURE:
<223> OTHER INFORMATION: Artificial primer

<400> SEQUENCE: 6
gcgaattccg tcaaagggag cggtaaatg                                    29

<210> SEQ ID NO 7
<211> LENGTH: 57
<212> TYPE: DNA
<213> ORGANISM: Artificial
<220> FEATURE:
<223> OTHER INFORMATION: Artificial primer

<400> SEQUENCE: 7
tcaacgtaag tgtgttatta aaaaataaa aaaacacagc aaaaaatgag atctgtc      57

<210> SEQ ID NO 8
<211> LENGTH: 58
<212> TYPE: DNA
<213> ORGANISM: Artificial
<220> FEATURE:
<223> OTHER INFORMATION: Artificial primer

<400> SEQUENCE: 8
tttatgctaa ctcgttaaat ttttaaaaat aaatttaaca aaatgtataa agcgattt    58

<210> SEQ ID NO 9
<211> LENGTH: 164
<212> TYPE: PRT
<213> ORGANISM: Vibrio cholerae

<400> SEQUENCE: 9

Met Ile Gly Lys Lys Ser Phe Gln Thr Asn Val Tyr Arg Met Ser Lys
1               5                   10                  15

Phe Asp Thr Tyr Ile Phe Asn Asn Leu Tyr Ile Asn Asp Tyr Lys Met
            20                  25                  30

-continued

```
Phe Trp Ile Asp Ser Gly Ile Ala Lys Leu Ile Asp Lys Asn Cys Leu
         35                  40                  45

Val Ser Tyr Glu Ile Asn Ser Ser Ile Ile Leu Lys Lys Asn
 50                  55                  60

Ser Ile Gln Arg Phe Ser Leu Thr Ser Leu Ser Asp Glu Asn Ile Asn
 65                  70                  75                  80

Val Ser Val Ile Thr Ile Ser Asp Ser Phe Ile Arg Ser Leu Lys Ser
                     85                  90                  95

Tyr Ile Leu Gly Asp Leu Met Ile Arg Asn Leu Tyr Ser Glu Asn Lys
                100                 105                 110

Asp Leu Leu Leu Trp Asn Cys Glu His Asn Asp Ile Ala Val Leu Ser
                115                 120                 125

Glu Val Val Asn Gly Phe Arg Glu Ile Asn Tyr Ser Asp Glu Phe Leu
130                 135                 140

Lys Val Phe Phe Ser Gly Phe Phe Ser Lys Val Glu Lys Lys Tyr Asn
145                 150                 155                 160

Ser Ile Phe Ile

<210> SEQ ID NO 10
<211> LENGTH: 164
<212> TYPE: PRT
<213> ORGANISM: Vibrio cholerae
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid

<400> SEQUENCE: 10

Met Ile Glu Lys Xaa Ser Phe Leu Val Asn Val Tyr Xaa Leu Xaa Lys
 1               5                  10                  15

Phe Glu Thr Tyr Ala Phe Asn Lys Val Phe Ile Asp Asp Tyr Lys Ile
                 20                  25                  30

Phe Trp Ile Asn Lys Gly Ser Ala Lys Leu Val Asp Lys Asn Cys Leu
             35                  40                  45

Val Asn Tyr Thr Ile Thr Xaa Asn Ser Val Val Leu Lys Lys Asn
 50                  55                  60

Ser Ile Gln Arg Phe Ser Leu Met Ser Leu Ser Asp Glu Ser Ile Ser
 65                  70                  75                  80

Val Cys Val Leu Thr Ile Lys Asn Lys Phe Val Asn Ser Leu Arg His
                     85                  90                  95

Tyr Leu Gln Gly Asp Leu Met Ile Arg Asn Leu Tyr Asn Glu Lys Lys
                100                 105                 110

Asp Leu Leu Leu Trp Asn Cys Glu Leu Asn Asp Ile Ser Val Leu Gly
                115                 120                 125

Glu Ile Val Ser Thr Tyr Asp Gln Thr Gln Tyr Ser Glu Asp Phe Leu
130                 135                 140

Lys Ile Phe Phe Ser Gly Phe Phe Ser Lys Val Glu Lys Lys Tyr Asn
145                 150                 155                 160
```

Ser Ile Phe Ile

<210> SEQ ID NO 11
<211> LENGTH: 54
<212> TYPE: PRT
<213> ORGANISM: Vibrio cholerae

<400> SEQUENCE: 11

Thr Asp Asp Leu Asp Ala Met Glu Lys Ile Ser Cys Leu Val Lys Ser
1               5                   10                  15

Asp Ile Thr Arg Asn Trp Arg Trp Ala Asp Ile Cys Gly Glu Leu Arg
            20                  25                  30

Thr Asn Arg Met Ile Leu Lys Lys Glu Leu Glu Ser Arg Gly Val Lys
        35                  40                  45

Phe Arg Glu Leu Ile Asn
    50

<210> SEQ ID NO 12
<211> LENGTH: 55
<212> TYPE: PRT
<213> ORGANISM: Vibrio cholerae

<400> SEQUENCE: 12

Glu Asn Ser Ala Ser Arg Leu Asn Leu Leu Ala Trp Leu Glu Asp
1               5                   10                  15

His Phe Ala Asp Glu Val Asn Trp Asp Ala Val Ala Asp Gln Phe Ser
            20                  25                  30

Leu Ser Leu Arg Thr Leu His Arg Gln Leu Lys Gln Gln Thr Gly Leu
        35                  40                  45

Thr Pro Gln Arg Tyr Leu Asn
    50                  55

<210> SEQ ID NO 13
<211> LENGTH: 55
<212> TYPE: PRT
<213> ORGANISM: Vibrio cholerae

<400> SEQUENCE: 13

Thr Ser Ser Glu Thr Leu Leu Asp Lys Leu Ile Thr Arg Leu Ala Ala
1               5                   10                  15

Ser Leu Lys Ser Pro Phe Ala Leu Asp Lys Phe Cys Asp Glu Ala Ser
            20                  25                  30

Cys Ser Glu Arg Val Leu Arg Gln Gln Phe Arg Gln Gln Thr Gly Met
        35                  40                  45

Thr Ile Asn Gln Tyr Leu Arg
    50                  55

<210> SEQ ID NO 14
<211> LENGTH: 55
<212> TYPE: PRT
<213> ORGANISM: Vibrio cholerae

<400> SEQUENCE: 14

Met Ser His Gln Lys Ile Ile Gln Asp Leu Ile Ala Trp Ile Asp Glu
1               5                   10                  15

His Ile Asp Gln Pro Leu Asn Ile Asp Val Val Ala Lys Lys Ser Gly
            20                  25                  30

Tyr Ser Lys Trp Tyr Leu Gln Arg Met Phe Arg Thr Val Thr His Gln
        35                  40                  45

Thr Leu Gly Asp Tyr Ile Arg

```
<210> SEQ ID NO 15
<211> LENGTH: 55
<212> TYPE: PRT
<213> ORGANISM: Vibrio cholerae

<400> SEQUENCE: 15

Met Asp Gln Ala Gly Ile Ile Arg Asp Leu Leu Ile Trp Leu Glu Gly
1               5                   10                  15

His Leu Asp Gln Pro Leu Ser Leu Asp Asn Val Ala Ala Lys Ala Gly
            20                  25                  30

Tyr Ser Lys Trp His Leu Gln Arg Met Phe Lys Asp Val Thr Gly His
        35                  40                  45

Ala Ile Gly Ala Tyr Ile Arg
    50                  55

<210> SEQ ID NO 16
<211> LENGTH: 55
<212> TYPE: PRT
<213> ORGANISM: Vibrio cholerae

<400> SEQUENCE: 16

Asn Thr Asp Ala Ile Thr Ile His Ser Ile Leu Asp Trp Ile Glu Asp
1               5                   10                  15

Asn Leu Glu Ser Pro Leu Ser Leu Glu Lys Val Ser Glu Arg Ser Gly
            20                  25                  30

Tyr Ser Lys Trp His Leu Gln Arg Met Phe Lys Lys Glu Thr Gly His
        35                  40                  45

Ser Leu Gly Gln Tyr Ile Arg
    50                  55

<210> SEQ ID NO 17
<211> LENGTH: 56
<212> TYPE: PRT
<213> ORGANISM: Vibrio cholerae

<400> SEQUENCE: 17

Pro Pro Met Asp Asn Arg Val Arg Glu Ala Cys Gln Tyr Ile Ser Asp
1               5                   10                  15

His Leu Ala Asp Ser Asn Phe Asp Ile Ala Ser Val Ala Gln His Phe
            20                  25                  30

Cys Leu Ser Pro Ser Arg Leu Ser His Leu Phe Arg Gln Gln Leu Gly
        35                  40                  45

Ile Ser Val Leu Ser Trp Arg Glu
    50                  55

<210> SEQ ID NO 18
<211> LENGTH: 58
<212> TYPE: PRT
<213> ORGANISM: Vibrio cholerae

<400> SEQUENCE: 18

Ser Ile Arg Ile Ser Tyr Ser Ile Ser Leu Met Lys Thr Gly Glu Phe
1               5                   10                  15

Lys Ile Lys Gln Ile Ala Tyr Gln Ser Gly Phe Ala Ser Val Ser Tyr
            20                  25                  30

Phe Ser Thr Val Phe Lys Ser Thr Met Asn Val Ala Pro Ser Glu Tyr
        35                  40                  45

Leu Phe Met Leu Thr Gly Val Ala Glu Lys
```

```
            50                  55

<210> SEQ ID NO 19
<211> LENGTH: 57
<212> TYPE: PRT
<213> ORGANISM: Vibrio cholerae

<400> SEQUENCE: 19

Arg Leu Arg Leu Met Lys Ala Arg His Leu Leu Arg His Ser Glu Ala
1               5                   10                  15

Ser Val Thr Asp Ile Ala Tyr Arg Cys Gly Phe Ser Asp Ser Asn His
            20                  25                  30

Phe Ser Thr Leu Phe Arg Arg Glu Phe Asn Trp Ser Pro Arg Asp Ile
        35                  40                  45

Arg Gln Gly Arg Asp Gly Phe Leu Gln
    50                  55

<210> SEQ ID NO 20
<211> LENGTH: 56
<212> TYPE: PRT
<213> ORGANISM: Vibrio cholerae

<400> SEQUENCE: 20

Gln Val Arg Val Cys His Ala Gln Tyr Leu Leu Gln His Ser Arg Leu
1               5                   10                  15

Leu Ile Ser Asp Ile Ser Thr Glu Cys Gly Phe Glu Asp Ser Asn Tyr
            20                  25                  30

Phe Ser Val Val Phe Thr Arg Glu Thr Gly Met Thr Pro Ser Gln Trp
        35                  40                  45

Arg His Leu Asn Ser Gln Lys Asp
    50                  55

<210> SEQ ID NO 21
<211> LENGTH: 52
<212> TYPE: PRT
<213> ORGANISM: Vibrio cholerae

<400> SEQUENCE: 21

Gln Arg Arg Leu Leu Leu Ala Ala Val Glu Leu Arg Thr Thr Glu Arg
1               5                   10                  15

Pro Ile Phe Asp Ile Ala Met Asp Leu Gly Tyr Val Ser Gln Gln Thr
            20                  25                  30

Phe Ser Arg Val Phe Arg Arg Gln Phe Asp Arg Thr Pro Ser Asp Tyr
        35                  40                  45

Arg His Arg Leu
    50

<210> SEQ ID NO 22
<211> LENGTH: 58
<212> TYPE: PRT
<213> ORGANISM: Vibrio cholerae

<400> SEQUENCE: 22

Ala Arg Arg Leu Ser Lys Ser Ala Val Ala Leu Arg Leu Thr Ala Arg
1               5                   10                  15

Pro Ile Leu Asp Ile Ala Leu Gln Tyr Arg Phe Asp Ser Gln Gln Thr
            20                  25                  30

Phe Thr Arg Ala Phe Lys Lys Gln Phe Ala Gln Thr Pro Ala Leu Tyr
        35                  40                  45

Arg Arg Ser Pro Glu Trp Ser Ala Phe Gly
```

```
<210> SEQ ID NO 23
<211> LENGTH: 58
<212> TYPE: PRT
<213> ORGANISM: Vibrio cholerae

<400> SEQUENCE: 23

Ser Arg Lys Met Thr Glu Ile Ala Gln Lys Leu Lys Glu Ser Asn Glu
1               5                   10                  15

Pro Ile Leu Tyr Leu Ala Glu Arg Tyr Gly Phe Glu Ser Gln Gln Thr
            20                  25                  30

Leu Thr Arg Thr Phe Lys Asn Tyr Phe Asp Val Pro Pro Lys His Tyr
        35                  40                  45

Arg Met Thr Asn Met Gln Gly Glu Ser Arg
        50                  55

<210> SEQ ID NO 24
<211> LENGTH: 58
<212> TYPE: PRT
<213> ORGANISM: Vibrio cholerae

<400> SEQUENCE: 24

Asp Gln Arg Ile Ser Gln Ala Lys Leu Leu Leu Ser Thr Thr Arg Met
1               5                   10                  15

Pro Ile Ala Thr Val Gly Arg Asn Val Gly Phe Asp Asp Gln Leu Tyr
            20                  25                  30

Phe Ser Arg Val Phe Lys Lys Cys Thr Gly Ala Ser Pro Ser Glu Phe
        35                  40                  45

Arg Ala Gly Cys Glu Glu Lys Val Asn Asp
        50                  55
```

IDENTIFICATION OF RESIDUES CRITICAL FOR THE FUNCTION OF THE VIBRIO CHOLERAE VIRULENCE REGULATOR TOXT BY SCANNING ALANINE MUTAGENESIS

This application claims the benefit of priority to U.S. Provisional Patent Application Ser. No. 60/886,908 filed on Jan. 26, 2007, the entire contents of which is hereby incorporated by reference in its entirety.

This invention was made with government support under grant no. AI051333 awarded by the National Institutes of Health. The government has certain rights in the invention.

BACKGROUND OF THE INVENTION

1. Field of the Invention

The present invention relates to the fields of infectious disease, vaccines, molecular biology, and the treatment and prevention of cholera.

2. Description of Related Art

*Vibrio cholerae* is a Gram-negative bacterium that is responsible for the deadly diarrheal disease cholera. The bacterium expresses virulence factors within the human intestine that lead to intestinal colonization and disease symptoms. Two of the most important virulence factors are cholera toxin (CT), an ADP-ribosylating toxin that is largely responsible for the symptoms of disease, and the toxin coregulated pilus (TCP), a type IV pilus essential for intestinal colonization (Gill, 1976; Mekalanos et al., 1983; Pearson and Mekalanos, 1982; Herrington et al., 1988).

ToxT, an AraC family protein, activates the transcription of the genes encoding CT (ctx) and TCP (tcp), as well as the genes encoding other poorly understood "accessory colonization factors" (acf) (DiRita et al., 1991). Since toxT lies within the tcp gene cluster, ToxT is also able to regulate its own expression, allowing for continuous expression of ToxT under favorable conditions (Brown and Taylor, 1995; Yu and DiRita, 1999). *V. cholerae* strains lacking toxT express no CT or TCP, and fail to colonize the intestine (DiRita et al., 1996; Champion et al., 1997). ToxT binds to specific sites upstream of the ctxA, tcpA, acfa, tagA and aldA promoters (Eithey and DiRita, 2005; Withey and DiRita, 2005; Hulbert and Taylor, 2002) to stimulate transcription. The location of all of these binding sites is at least 45 bp upstream of the transcription startsite, with the exception of the ctxA promoter, where ToxT protects a region up to −13. This suggests that the tcpA, acfA, tagA, and aldA promoters are "Class I" AraC-like promoters (i.e., activated from sites that do not overlap with the −35 element), and consistent with this mode of activation, it has been demonstrated that ToxT-dependent tcpA transcription requires the C-terminal domain of the α subunit of RNAP (Hulbert and Taylor, 2002). However, the overlap of ToxT binding with the −35 element (albeit at lower affinity) at the ctxA promoter may indicate that this represents activation of a "Class II" AraC-like promoter, which has been shown in some AraC-like activators [e.g., RhaS, RhaR, MelR] (Wickstrum and Egan, 2004; Grainger et al., 2004) to involve contacts between the activator and $\sigma^{70}$.

Recently, a "toxbox" motif (yrTTTTwwTwAww) has been identified within the ToxT-bound region at ToxT-activated promoters (Withey and DiRita, 2006). At all ToxT-activated promoters with the exception of aldA, two toxbox sequences are found in either a direct or inverted orientation. It has been shown that the insertion of 5 bp and 10 bp between the two toxboxes found at the acfa and tcpA promoters prevents transcriptional activation, but still allows ToxT binding in vitro (Withey and DiRita, 2005; Withey and DiRita, 2006). These results suggest that single ToxT monomers bind each toxbox, and that interactions between monomers are likely important for transcriptional activation.

AraC family members are classified based on homology to a 99 amino acid stretch within the AraC carboxy-terminus (Gallegos et al., 1997). The crystal structures of two AraC family proteins, MarA and Rob, complexed with DNA, have been resolved and the structures demonstrated that this region encodes two distinct helix-turn-helix (HTH) motifs that function in DNA-binding (Gallegos et al., 1997; Rhee et al., 1998; Kwon et al., 2000). MarA, Rob, and another protein, SoxS, are all able to bind to the same promoter elements (alternatively referred to as marbox/robbox/soxbox) and activate an overlapping set of genes, albeit with different affinities (Jair et al., 1996; Jair et al., 1995; Greenberg et al., 1990). The crystal structure of MarA bound to the mar promoter identified base- and phosphate backbone-specific contacts made between the first HTH (HTH1) and the 4 bp recognition element (RE)1 motif of the marbox, and specific contacts made between HTH2 and the 4 bp RE2 motif; RE1 and RE2 are centered on the same face of the DNA helix and separated by a 7 bp A/T-rich spacer. However, alanine substitution mutagenesis of MarA has suggested that while both HTH motifs contribute to DNA binding, the individual contributions of contacts made between HTH1 and RE1 are more important to DNA binding than HTH2-RE2 contacts (Gillette et al., 2000), and similar conclusions were drawn from alanine substitution mutagenesis of SoxS (Griffith and Wolf, 2002). Moreover, the crystal structure of Rob bound to the micF promoter indicated base- and phosphate backbone-specific contacts between HTH1 and RE1, similar to those found in the MarA-mar structure, but no base-specific contacts between HTH2 and RE2 and only one specific contact to the phosphate backbone (Kwon et al., 2000). It has been shown that bile acids interact with Rob to induce transcription (Rosenberg et al., 2003), so perhaps the apparent lack of specific contacts between HTH2 and RE2 may be due to a lack of inducer during crystallization. Studies of DNA binding by several AraC family members including AraC, MelR, RhaS, SoxS, and MarA have indicated that the orientation of the promoter-proximally bound activator depends on the distance to the −35 element, with the HTH2 oriented closest to the −35 element at Class II-like promoters (where the activator binding site extends downstream to at least −40) and with HTH1 oriented closest to the −35 element when the binding site is further upstream of the −35 element (Grainger et al., 2004; Porter and Dorman, 2002; Grainger et al., 2003; Behnde and Egan, 1999; Niland et al., 1996; Martin and Rosner, 2001; Martin et al., 1999; Wood et al., 1999).

The amino-terminus of AraC is responsible for dimerization and binding of the effector arabinose (Bustos and Schleif, 1993). The crystal structure of the amino terminus of AraC has also been resolved and revealed arabinose bound within an eight-stranded anti-parallel beta barrel "jelly roll" structure at the N-terminal end, and an antiparallel coiled-coil that mediates dimerization at the C-terminal end of this domain (Soisson et al., 1997). In general the N-termini of AraC family proteins (if present) do not share significant sequence homology, but they often share similar functions with the AraC N-terminus, such as oligomerization and/or effector binding (Gallegos et al., 1997; Martin and Rosner, 2001).

ToxT, like AraC, appears to contain two distinct domains: an N-terminal domain involved in dimerization and possibly environmental sensing, and a C-terminal domain necessary for DNA binding (Prouty et al., 2005). The ToxT N-terminus fused to the DNA binding domain of LexA is able to repress sulA transcription, consistent with dimerization determinants being located within the N-terminal domain. The ToxT N-terminus shares little sequence homology with the AraC N-terminus, but it is predicted to share secondary and tertiary structural similarities, as determined by Threading programs (Soding et al., 2005) (discussed below). Two different mutant forms of the N-terminus were identified that exhibited altered responses to the repressive effects of bile, suggesting that there are environmentally responsive elements within the N-terminus. The ToxT C-terminus is able to bind DNA, but only when fused to a heterologous dimerization domain, demonstrating that the C-terminus is sufficient for DNA binding, and that the C-terminus requires dimerization for DNA binding. Interestingly, the dimerized C-terminus is unable to activate transcription, suggesting that, unlike AraC and several other family members (Bustos and Schleif, 1993; Poore et al., 2001 there may be additional determinants in the ToxT N-terminus required for transcriptional activation.

This invention concerns the identification of amino acids critical for ToxT function. Specific amino acids involved in dimerization, DNA binding, and environmental modulation of ToxT have been identified. This information can be applied in the prevention and treatment of cholera.

SUMMARY OF THE INVENTION

The present invention concerns the identification of detailed information pertaining to mutations in the ToxT protein of *Vibrio cholerae* that affect virulance of *Vibrio cholerae*. This information can be applied, for example, in the design of vaccines to prevent cholera and in the treatment of cholera.

Particular aspects of the present invention generally concern a *Vibrio cholerae* comprising a mutated transcriptional regulatory protein (ToxT) amino acid sequence, wherein the mutation results in a reduction in the expression of cholera toxin by the *Vibrio cholerae*. An example of wild-type ToxT amino acid sequence is as set forth in SEQ ID NO:2. SEQ ID NO:1 sets forth the polynucleotide sequence of a *Vibrio cholera* pathogenicity island, which contains a cluster of virulence genes including the ToxT gene that encodes SEQ ID NO:2. Examples of mutations of ToxT contemplated by the present invention are discussed in greater detail below. Reduction in the expression of cholera toxin by the *Vibrio cholerae* is reduced expression relative to expression of cholera toxin by a *Vibrio cholerae* that does not include the mutated ToxT amino acid sequence.

The present invention also pertains to a *Vibrio cholerae* comprising a mutated transcriptional regulatory protein (ToxT) amino acid sequence, wherein the mutation results in an increase in transcription of a nucleic acid of the *Vibrio cholerae* encoding a Toxin Coregulated Pilus (TCP). An increase in transcription of a nucleic acid of the *Vibrio cholerae* encoding a TCP is an increase relative to the transcription of a nucleic acid encoding a TCP of a *Vibrio cholerae* that does not comprise a mutated ToxT amino acid sequence.

Additional embodiments of the present invention pertain to a vaccine comprising a *Vibrio cholerae* that expresses a mutated ToxT, wherein the mutation results in reduced expression of cholera toxin by the *Vibrio cholerae*. In other embodiments, the invention pertains to a vaccine comprising a *Vibrio cholerae* that expresses a mutated ToxT, wherein the mutation results in an increase in transcription of a nucleic acid of the *Vibrio cholerae* that encodes a TCP.

The present invention also generally pertains to methods of preventing or treating cholera, comprising administering to a subject a composition comprising a *Vibrio cholerae* comprising a mutated transcriptional regulatory protein (ToxT) amino acid sequence, wherein the mutation results in a reduction in the expression of cholera toxin by the *Vibrio cholerae*. In particular embodiments, the method is a method of preventing cholera. The invention also addresses methods of treating or preventing cholera, comprising administering to a subject a composition comprising a *Vibrio cholerae* comprising a mutated transcriptional regulatory protein (ToxT) amino acid sequence, wherein the mutation results in an increase in transcription of a nucleic acid of the *Vibrio cholerae* that encodes a TCP.

Also disclosed are recombinant ToxT amino acid sequences, wherein the sequence comprises a mutated ToxT amino acid sequence that, when expressed in a *Vibrio cholerae*, results in a reduction in the expression of cholera toxin by the *vibrio cholerae* or an increase in transcription of the nucleic acid encoding a TCP. For example, the recombinant ToxT may be any of the ToxT mutants set forth in the specification below. Particular examples of such mutants are set forth in Table 1-Table 3 below. Also disclosed are polynucleotide sequences that comprise a nucleic acid sequence that encodes a mutated ToxT protein as set forth herein.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
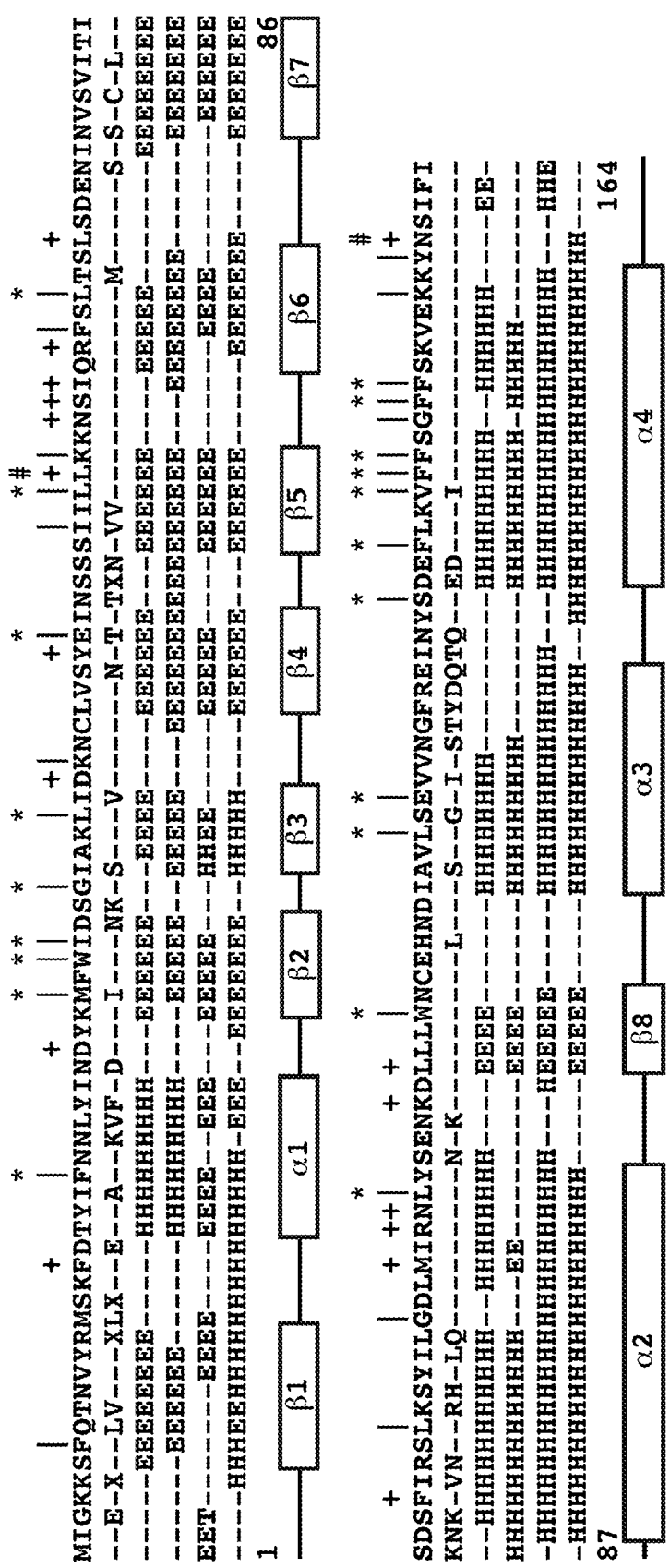
FIG. 1: Summary of effect of Alanine substitutions in the N-terminus of ToxT: The amino acid sequence of the N-terminus of ToxT from epidemic *V. cholerae* strains is shown on the top line (aa 1-164) (SEQ ID NO:9), as well as alterations from this sequence found in the N-termini of ToxT from environmental *V. cholerae* strains (second line; X denotes more than one substitution found at this residue (SEQ ID NO:10)) (Mukhopadhyay et al., 2001). The effects of Ala substitutions on ToxT transcriptional activity are summarized above the amino acid sequence. Ala substitutions that resulted in <10% WT activity in either the ctxA-lacZ reporter strain or the acfA-phoA reporter strain are denoted by a line "l". Ala substitutions that resulted in <10% WT activity in both the ctxA-lacZ reporter strain and the acfA-phoA reporter strain are denoted by an asterisk "*" above the line; these are the "critical" amino acids. Ala substitutions that resulted in >300% WT activity in either the ctxA-lacZ reporter strain or the acfA-phoA reporter strain are denoted by a plus sign "+". Ala substitutions that resulted in >300% WT activity in both the ctxA-lacZ reporter strain and the acfA-phoA reporter strain are denoted by a pound sign "#" above the plus sign. Secondary structure predictions from jpred, PROF, SOPMA, and PSIPRED (Cuff et al., 1998; Geourjon and Deleage, 1995; McGuffin et al., 2000; Ouali and King, 2000) are shown in lines 3-6, respectively, and the consensus prediction is depicted below. Numbering refers to primary sequence of ToxT from epidemic *V. cholerae*.

ToxT is a key regulatory protein in the virulence of *V. cholerae*. This AraC-like protein is the direct transcriptional activator of genes encoding the critical virulence factors cholera toxin (ctx) and the toxin-coregulated pilus (tcp), as well as accessory colonization factors (acf). Despite the important role ToxT plays in cholera pathogenesis, very little is known about the structure and function of this protein. We have previously shown that the N-terminus contains dimerization determinants and environmentally responsive elements, while the C-terminus contains DNA binding determinants. Interestingly, unlike some other AraC family proteins, the dimerized C-terminus of ToxT is unable to activate transcription despite being able to bind DNA, suggesting that elements in the N-terminus are also required for transcriptional activation.

The present invention concerns the identification of detailed information pertaining to mutations in the ToxT protein of *Vibrio cholerae* that affect virulance of *Vibrio cholerae*. This information can be applied, for example, in the design of vaccines to prevent cholera.

A. DEFINITIONS

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence.

The term "variant" may also be used to indicate a modified or altered gene, DNA sequence, RNA, enzyme, cell, etc.; i.e., any kind of mutant.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

A "coding sequence" or a sequence "encoding" an expression product, such as a RNA, polypeptide, protein or enzyme, is a nucleotide sequence that, when expressed, results in the production of that RNA, polypeptide, protein or enzyme; i.e., the nucleotide sequence "encodes" that RNA or it encodes the amino acid sequence for that polypeptide, protein or enzyme.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently found, for example, by mapping with nuclease S1), as well as protein binding domains (consensus sequences) responsible for the binding of RNA polymerase.

A coding sequence is "under the control of" or is "operatively associated with" transcriptional and translational control sequences in a cell when RNA polymerase transcribes the coding sequence into RNA, which is then trans-RNA spliced (if it contains introns) and, if the sequence encodes a protein, is translated into that protein.

The term "express" and "expression" means allowing or causing the information in a gene or DNA sequence to become manifest, for example producing RNA (such as rRNA or mRNA) or a protein by activating the cellular functions involved in transcription and translation of a corresponding gene or DNA sequence. A DNA sequence is expressed by a cell to form an "expression product" such as an RNA (e.g., a mRNA or a rRNA) or a protein. The expression product itself, e.g., the resulting RNA or protein, may also said to be "expressed" by the cell.

The term "transfection" means the introduction of a foreign nucleic acid into a cell. The term "transformation" means the introduction of a "foreign" (i.e., extrinsic or extracellular) gene, DNA or RNA sequence into a host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell or cells of a different genus or species.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc. and are discussed in greater detail below.

The terms "substantial homology" or "substantial similarity," when referring to a nucleic acid or fragment thereof, indicate that, when optimally aligned with appropriate nucleotide insertions or deletions with another nucleic acid (or its complementary strand), there is nucleotide sequence identity in at least about 70% of the nucleotide bases, as measured by any well-known algorithm of sequence identity.

The term "homologous" as used herein, refers to the sequence similarity between two polymeric molecules, e.g., between two nucleic acid molecules, e.g., two DNA molecules or two RNA molecules, or between two polypeptide molecules. When a nucleotide or amino acid position in both of the two molecules is occupied by the same monomeric nucleotide or amino acid, e.g., if a position in each of two DNA molecules is occupied by adenine, then they are homologous at that position. The homology between two sequences is a direct function of the number of matching or homologous positions of the positions in two compound sequences are homologous, then the two sequences are 50% homologous. If 90% of the positions, such as if 9 of 10, are matched or homologous, the two sequences share 90% homology. By way of example, the DNA sequences 3'ATTGCC5' and 3'TATGCG5' share 50% homology. By the term "substantially homologous" as used herein, is meant DNA or RNA which is about 70% homologous, more preferably about 80% homologous, and most preferably about 90% homologous to the desired nucleic acid.

By describing two DNAs as being "operably linked" as used herein, is meant that a single-stranded or double-stranded DNA comprises each of the two DNAs and that the two DNAs are arranged within the DNA in such a manner that at least one of the DNA sequences is able to exert a physiological effect by which it is characterized upon the other.

B. MUTATED ToxT AMINO ACID SEQUENCES

Mutations of a protein as set forth herein refer to deletions, substitutions, or insertions. Any amino acid that may replace a residue from the wild-type protein.

An example of wild-type ToxT amino acid sequence is as set forth in SEQ ID NO:2. SEQ ID NO:1 sets forth the polynucleotide sequence of a *Vibrio cholera* pathogenicity island, which contains a cluster of virulence genes including the ToxT gene that encodes SEQ ID NO:2. Examples of mutations of ToxT contemplated by the present invention are discussed in greater detail below.

The putative location of the removed or added amino acid residues could be determined by comparison of the mutated sequence to that of the unmutated protein, polypeptide or peptide's secondary and tertiary structure, as determined by such methods known to those of ordinary skill in the art including, but not limited to, X-ray crystallography, NMR or computer modeling. Computer models of various polypeptide and peptide structures are also available in the literature or computer databases. In a non-limiting example, the Entrez database (http://www.ncbi.nlm.nih.gov/Entrez/) may be used by one of ordinary skill in the art to identify target sequences and regions for mutagenesis. The Entrez database is crosslinked to a database of 3-D structures for the identified amino acid sequence, if known. The mutated or wild-type protein, polypeptide or peptide's structure could be determined by X-ray crystallography or NMR directly before use in in vitro or in vivo assays, as would be known to one of ordinary skill in the art.

Once an amino acid is altered in a ToxT peptide, polypeptide or protein, or removed from to a peptide, polypeptide or protein, changes in its ability to promote at least effect may be assayed by any of the techniques described herein or as would be known to one of ordinary skill in the art.

As used herein, "alter", "altered", "altering", "alteration" of an amino acid ToxT sequence may include chemical modification of an amino acid sequence comprising a sequence in a protein, polypeptide or peptide as would be known to those of ordinary skill in the art, as well as any mutation of such an amino acid sequence including but not limited to insertions, deletions, truncations, or substitutions.

For example, mutations including but not limited to at least one insertion or substitution of at least one amino acid selected from the group phenylalanine (F); cysteine (C); methionine (M); alanine (A); threonine (T); serine (S); tryptophan (W); tyrosine (Y); proline (P); histidine (H); glutamic acid (E); glutamine (Q); aspartic acid (D); asparagine (N); lysine (K); and arginine (R), and modified or unusual amino acids. It is also contemplated that mutations including but not limited to at least one insertion or substitution of at least one amino acid selected from the group isoleucine (I); valine (V); leucine (L); phenylalanine (F); cysteine (C); methionine (M); alanine (A); glycine (G); threonine (T); serine (S); tryptophan (W); tyrosine (Y); proline (P); histidine (H); glutamic acid (E); glutamine (Q); asparagine (N); lysine (K); and arginine (R).

C. VACCINES

Certain embodiments of the present invention concern vaccines. For an antigenic composition to be useful as a vaccine, an antigenic composition must induce an immune response to the antigen in a cell, tissue or animal (e.g., a human). As used herein, an "antigenic composition" may comprise an antigen (e.g., a peptide or polypeptide), a nucleic acid encoding an antigen (e.g., an antigen expression vector), or a cell expressing or presenting an antigen. In some embodiments, the vaccines include a mutated ToxT. In particular embodiments, the vaccine includes a *Vibrio cholerae* that express a mutated ToxT as set forth herein. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In certain embodiments, an antigenic composition or immunologically functional equivalent, may be used as an effective vaccine in inducing a humoral and/or cell-mediated immune response in an animal directed against *Vibrio cholerae*. The present invention contemplates one or more antigenic compositions or vaccines for use in both active and passive immunization embodiments.

A vaccine of the present invention may vary in its composition of proteinaceous, nucleic acid and/or cellular components. In a non-limiting example, a nucleic encoding an antigen might also be formulated with a proteinaceous adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

A cell expressing the antigen may comprise the vaccine, such as a *Vibrio cholerae*. The cell may be isolated from a culture, tissue, organ or organism and administered to an animal as a cellular vaccine. Thus, the present invention contemplates a "cellular vaccine." The cell may be transfected with a nucleic acid encoding an antigen to enhance its expression of the antigen. Of course, the cell may also express one or more additional vaccine components, such as immunomodulators or adjuvants. A vaccine may comprise all or part of the cell.

As modifications and changes may be made in the structure of an antigenic composition of the present invention, and still obtain molecules having like or otherwise desirable characteristics, such immunologically functional equivalents are also encompassed within the present invention.

For example, certain amino acids may be substituted for other amino acids in a peptide, polypeptide or protein structure without appreciable loss of interactive binding capacity with structures such as, for example, antigen-binding regions of antibodies, binding sites on substrate molecules or receptors, DNA binding sites, or such like. Since it is the interactive capacity and nature of a peptide, polypeptide or protein that defines its biological (e.g., immunological) functional activity, certain amino acid sequence substitutions can be made in a amino acid sequence (or, of course, its underlying DNA coding sequence) and nevertheless obtain a peptide or polypeptide with like (agonistic) properties. It is thus contemplated by the inventors that various changes may be made in the sequence of an antigenic composition such as, for example a mutated ToxT peptide or polypeptide, or underlying DNA, without appreciable loss of biological utility or activity.

D. TREATMENT OF DISEASE

Cholera is an infectious gastroenteritis caused by *Vibrio cholerae*. It is transmitted to humans through the ingestion of contaminated water or food. *V. cholerae* produces cholera toxin, an enterotoxin which acts on the mucosal epithelium of the small intestine to cause severe diarrhea. Death may occur quickly, within a day, if left untreated.

"Treatment" and "treating" as used herein refer to administration or application of a therapeutic agent to a subject or performance of a procedure or modality on a subject for the purpose of obtaining a therapeutic benefit of a disease or health-related condition. For example, treatment of cholera may include administration of a composition as set forth herein to reduce the fluid and electrolyte loss associated with cholera.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, a therapeutic benefit may include reduced risk of mortality associated with cholera.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition. Preventing cholera includes administration of an agent as set forth herein for the purpose of blocking the onset of cholera.

E. PHARMACEUTICAL VEHICLES AND ROUTES OF ADMINISTRATION

Aqueous compositions of the present invention will have an effective amounts of agent that prevents or treats cholera. Administration of therapeutic compositions according to the present invention will be via any route so long as the target tissue is available via that route. This includes gastrointestinal mucosa. Examples include direct orthopedic, intradermal, subcutaneous, intramuscular, intrapertioneal or intravenous injection. Such compositions generally will be dissolved or dispersed in a pharmaceutically acceptable carrier or aqueous medium.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients, such as other anti-cholera agents, can also be incorporated into the compositions.

In addition to the compounds formulated for parental administration, such as those for intravenous or intramuscular injection, other pharmaceutically acceptable forms include tablets or other solids for oral administration; time release capsules; and any other form currently used.

The active compounds of the present invention often will be formulated for parental administration, for example, formulated for injection via the subcutaneous, intradermal, oral, or intravenous routes. The preparation of an aqueous composition that contains an effective amount of therapeutic agents to treat or prevent cholera will be known to those of skill in the art in light of the present disclosure. Typically, such compositions can be prepared as injectables, either as liquid solutions or suspensions; and the preparations can be emulsified.

Solutions of the active ingredient can be prepared in water suitably mixed with a surfactant, such as hydroxypropylcellulose. Under ordinary conditions of storage and use, these preparations contain a preservative to prevent the growth of unwanted microorganisms. Under ordinary conditions of storage and use, preparations that include a *Vibrio cholerae* may contain agents to promote viability and/or growth of such organisms.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of unwanted microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the composition of agents delaying absorption, for example, aluminum monostearate and gelatin.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

F. COMBINATION THERAPIES

The methods and compositions including combination therapies enhance the therapeutic or protective effect, and/or increase the therapeutic effect of another anti-cholera therapy. Therapeutic and prophylactic methods and compositions can be provided in a combined amount effective to achieve the desired effect, such as the treatment of cholera.

The methods of treating or preventing cholera set forth herein can be administered before, during, after or in various combinations relative to other anti-cholera therapy. The administrations may be in intervals ranging from concurrently to minutes to days to weeks. Where separately provided to a patient, one would generally ensure that a significant period of time did not expire between the time of each delivery, such that the two agents would still be able to exert an advantageously combined effect on the patient. In such instances, it is contemplated that one may provide a patient with the therapies within about 12 to 24 or 72 h of each other and, more preferably, within about 6-12 h of each other.

Various combinations may be employed. For the example below the therapy of the present invention is "A" and the other anti-cholera therapy is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Administration of any composition of the present invention to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary.

A major goal of cholera therapy is to replace fluids and electrolytes lost through diarrhea using a simple rehydration solution that contains specific proportions of water, salts and sugar. The solution, called Oral Rehydration Salts (ORS), is available as a powder that can be reconstituted in boiled or bottled water. Administration of the therapeutic compositions of the present invention can be administered prior to, during, or following rehydration.

During a cholera epidemic, most people can be helped by oral rehydration alone, but severely dehydrated people may also need intravenous fluids In addition to rehydration, people who are severely ill with cholera may benefit from antibiotics, which can cut the length of the illness in half. Recent studies show that a single dose of azithromycin in adults or children with severe cholera helps shorten diarrhea duration and decreases vomiting.

G. EXAMPLES

Example 1

Alanine Scanning Site-Directed Mutagenesis of ToxT

Figure 2:
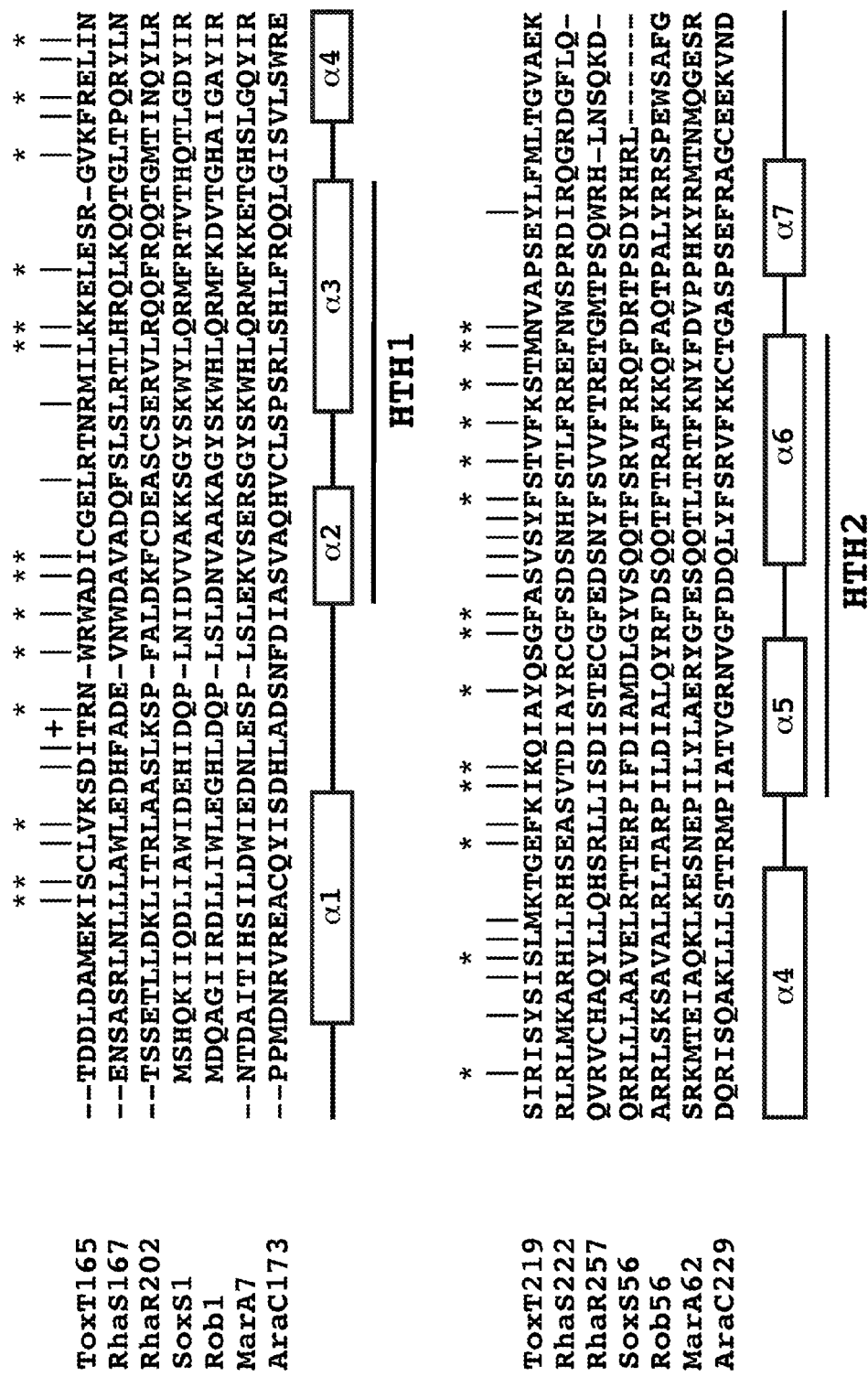
FIG. 2: Summary of effect of Alanine substitutions in the C-terminus of ToxT: The amino acid sequence of the C-terminus of ToxT from *V. cholerae* (aa 165-276) was aligned with the sequences of MarA (aa 7-119), SoxS (aa 1-107), Rob (aa 1-113), RhaS (aa 167-278), RhaR (aa 202-312) and AraC (aa 173-286) from *E. coli*, utilizing CLUSTALW alignment (SEQ ID NOS: 11-24). The secondary structural elements determined from the crystal structures of MarA and Rob ((Kwon et al., 2000; Rhee et al., 1998) are shown below the alignment. The effects of Ala substitutions on ToxT transcriptional activity are summarized above the amino acid sequence. Ala substitutions that resulted in <10% WT activity in either the ctxA-lacZ reporter strain or the acfA-phoA reporter strain are denoted by a line "|". Ala substitutions that resulted in <10% WT activity in both the ctxA-lacZ reporter strain and the acfA-phoA reporter strain are denoted by an asterisk "*" above the line; these are the "critical" amino acids. The Ala substitution that resulted in >300% WT activity in the ctxA-lacZ reporter strain is denoted by a plus sign "+". Numbering refers to primary sequence of ToxT from epidemic *V. cholerae*.
Figure 3:
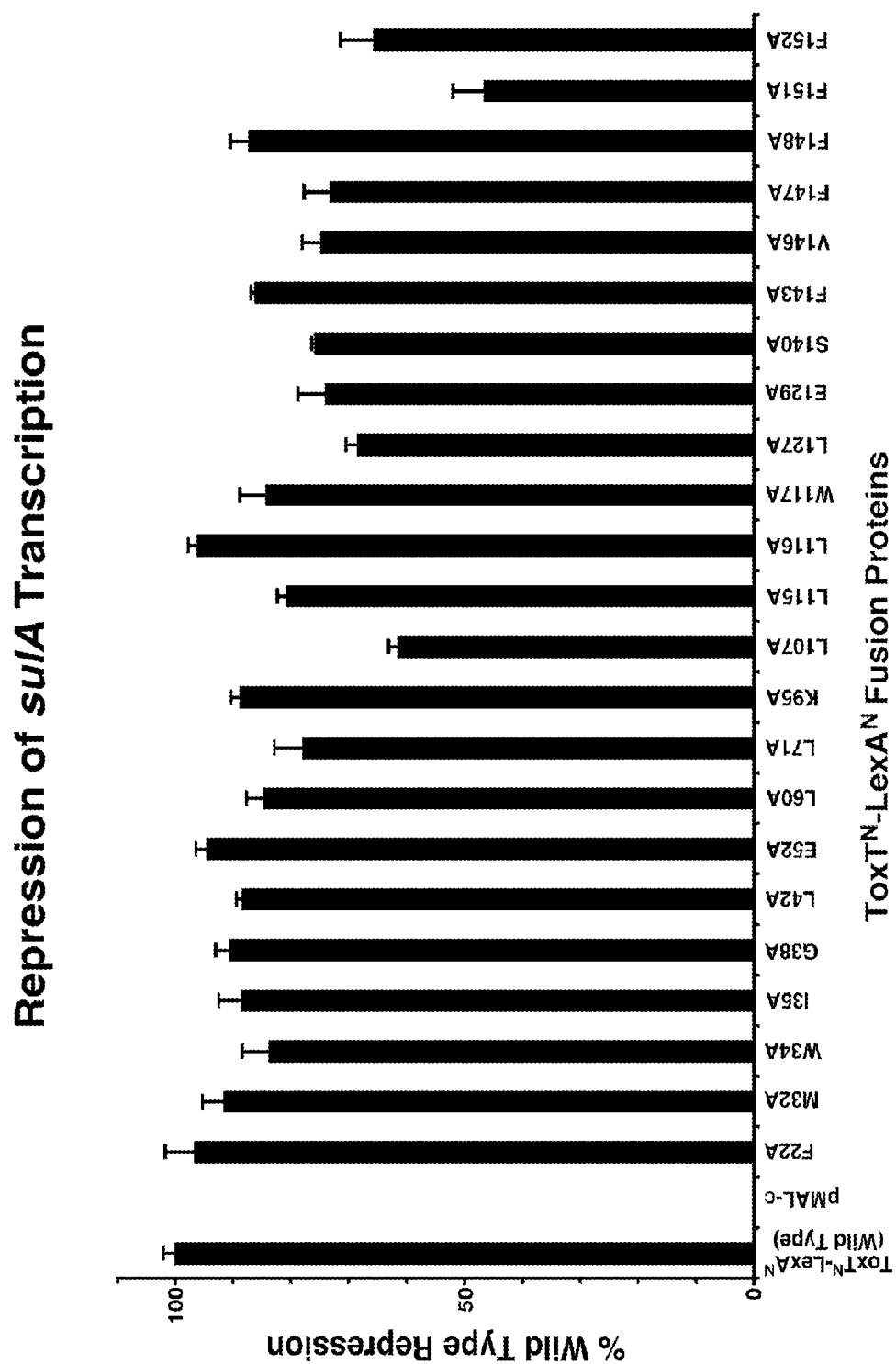
FIG. 3: Identification of Ala Substitutions that Decrease ToxT Dimerization. The *E. coli* strain JL1436 containing a chromosomal sulAp-lacZ transcriptional fusion and expressing the N-terminus of ToxT fused to the monomeric DNA binding domain of LexA was assayed for β-galactosidase activity; MBP-ToxT$^N$-LexA contained the Ala substitutions noted. Results are the averages and standard deviation of three samples, and are depicted as % WT repression, normalizing the MBP-ToxT$^N$-LexA ("wildtype") activity to 100%, and the activity seen in the absence of expressed protein ("pmalc") to 0%.

Previous experiments have identified two functional domains of ToxT, an N-terminal domain involved in dimerization and environmental sensing, and a C-terminal domain responsible for DNA binding (Prouty et al., 2005). The C-terminal domain corresponds to the portion of the protein with sequence homology to other AraC-like proteins (aa 165-276), and for convenience here the N-terminal domain is defined as the rest of the protein (aa 1-164; FIG. 1); this likely also contains a flexible linker region that connects the two domains. The 3 dimensional crystal structures of two AraC-like proteins, MarA and Rob, bound to DNA, have been resolved (Kwon et al., 2000; Rhee et al., 1998). These two structures are very similar to each other and likely very similar to the structure of the ToxT C-terminus (99.9% probabilities, HHpred scores 183.52, 182.17 (Soding et al., 2005); 99% confidence Fugue scores 19.60, 8.82 (Shi et al., 2001)). An alignment of the ToxT C-terminus to these two proteins, as well as to other well-characterized AraC family members (SoxS, RhaS, RhaR, and AraC) is shown in FIG. 2, along with the secondary structural features of this domain as determined by the crystal structures.

The 3-dimensional structure of the ToxT N-terminus is not known, but four different secondary structure prediction programs predict a satisfying consensus of features within the ToxT N-terminus, depicted in FIG. 1. The N-terminus appears to consist of a region of primarily beta structure (aa 1-86) followed by a primarily alpha helical region (aa 87-157). Approximately seven beta strands are predicted in the first portion, with a single alpha helical region predicted to lie between the first and second beta strand (approx. aa 19-27). In the second portion of the N-terminus, alpha helical regions are predicted from approx. aa 88-108, aa 124-136, and aa 141-158, with a single beta strand between the first and second helical regions (aa 114-118). Moreover, threading programs predict 3-dimensional structural similarity of the ToxT N-terminus to the N-terminus of AraC (92% probability, HHpred score 32.2 (Soding et al., 2005); 95% confidence Fugue z score 4.31 (Shi et al., 2001)). The AraC N-terminus consists of an eight stranded antiparallel beta-barrel "jelly roll" structure followed by a short alpha helix and a ninth beta strand that completes the "jelly roll" structure (Soisson et al., 1997). This is then followed by two long antiparallel alpha helices that form a "coiled coil" dimerization interface. A single molecule of arabinose binds and is completely buried within the beta barrel structure of each monomer. Several variant alleles of ToxT have been identified with amino acid alterations found almost exclusively within the N-terminus (Mukhopadhyay et al., 2001), and these altered amino acid residues are noted within FIG. 1. It has previously shown that at least one of these variant alleles retains ToxT transcriptional activity (Prouty et al., 2005), thus these naturally altered residues can be assumed to represent substitutions that do not significantly reduce ToxT function.

To identify residues critical for the function of ToxT, comprehensive site-directed mutagenesis was performed as described in Example 12 to change all amino acids of ToxT to alanine, with the exception of the starting methionine codon and the 8 alanines present in the ToxT protein sequence (at positions 40, 125, 170, 189, 240, 246, 262, and 274). Specific oligonucleotides incorporating the mutation were used to generate each mutant toxT allele, and each allele was verified to be correct by sequencing prior to any analyses. The plasmid template utilized, pKEK160, expresses MBP-ToxT from the pBAD promoter (Prouty et al., 2005), MBP facilitates detection and purification of ToxT without interfering with ToxT function (Schuhmacher and Klose, 1999). This resulted in the creation of a total of 267 mutant ToxT proteins with Alanine substitutions.

Example 2

ToxT Amino Acids Necessary for ctxAp-lacZ Transcriptional Activation

ToxT directly binds to and activates the ctxA promoter (Yu and DiRita, 2002). ToxT binds with high affinity to the ctxA promoter region from −111 to −41, and with lower affinity to the region −40 to −13. The high affinity binding region contains two toxbox motifs (−115 to −80) in a direct orientation (Withey and DiRita, 2006). The overlap of ToxT binding with the −35 element may indicate that this is a Class II AraC-like promoter.

To identify amino acids necessary for ToxT-dependent ctx transcription, each of the 267 Ala substitution mutants was assayed for β-galactosidase activity in a *S. typhimurium* reporter strain that contains a chromosomal ctxAp-lacZ transcriptional fusion (Schuhmacher and Klose, 1999). The ctxA promoter can also be activated to some degree by ToxR (Hung and Mekalanos, 2005), which is only found in *Vibrio* spp., so the heterologous reporter strain was utilized here to eliminate any possible cross-activation by ToxR. The components of the *S. typhimurium* $\sigma^{70}$-holoenzyme form of RNA polymerase share 78-88% identity and 86-94% similarity with those of *V. cholerae*. Each Ala substitution mutant was tested independently at least twice, with triplicate samples. The native MBP-ToxT protein was also assayed each time with every experiment, to allow a direct comparison of the levels of activity of the mutant and native proteins and eliminate any experiment-to-experiment variations in absolute β-galactosidase activity. The results are detailed in Table 1 and summarized in FIG. 1 for Ala substitution mutants within the N-terminus (aa 1-164), and detailed in Table 2 and summarized in FIG. 2 for Ala substitution mutants within the C-terminus (aa 165-276). Transcriptional activity of each mutant is reported as % activity of the native ToxT protein. Many mutations caused modest increases or decreases in ToxT-dependent transcription, but alterations were only considered "significant" if the activity was either <10% or >300% that of the native protein; all of these differences were deemed significant (p<0.001) utilizing Students 2-tailed t test.

TABLE 1

Effect of Alanine Substitutions in the ToxT N-terminus on transcriptional activity

| mutation | ctxAp-lacZ | acfA-phoA | class[a] | mutation | ctxAp-lacZ | acfA-phoA | class[a] | mutation | ctxAp-lacZ | acfA-phoA | class[a] |
|---|---|---|---|---|---|---|---|---|---|---|---|
| I2A | 86% | 102% |  | S57A | 279% | 134% |  | N111A | 132% | 70% |  |
| G3A | 72% | 103% |  | I58A | 33% | <1% |  | K112A | 326% | 44% | + |
| K4A | 47% | 60% |  | I59A | 22% | 115% |  | D113A | 158% | 55% |  |
| K5A | 94% | 67% |  | L60A | 6% | <1% | * | L114A | 317% | 84% | + |
| S6A | 166% | 73% |  | L61A | 336% | 526% | + | L115A | 13% | 20% |  |
| F7A | 26% | 1% |  | K62A | 117% | <1% |  | L116A | 118% | 76% |  |
| Q8A | 120% | 52% |  | K63A | 148% | 46% |  | W117A | <1% | 4% | * |
| T9A | 54% | 71% |  | N64A | 64% | 760% | + | N118A | 158% | 66% |  |
| N10A | 82% | 26% |  | S65A | 140% | 989% | + | N119A | 81% | 37% |  |
| V11A | 230% | 66% |  | I66A | 84% | 509% | + | E120A | 49% | 37% |  |
| Y12A | 264% | 100% |  | Q67A | 237% | 17% |  | M121A | 53% | 76% |  |
| R13A | 121% | 52% |  | R68A | 425% | 114% | + | N122A | 88% | 80% |  |
| M14A | 67% | 36% |  | F69A | 40% | <1% |  | D123A | 43% | 20% |  |
| S15A | 91% | 95% |  | S70A | 52% | 61% |  | I124A | 243% | 23% |  |
| K16A | 124% | 150% |  | L71A | 1% | <1% | * | V126A | 159% | 64% |  |
| F17A | 136% | 392% | + | T72A | 280% | 159% |  | L127A | <1% | 2% | * |
| D18A | 67% | 100% |  | S73A | 97% | 95% |  | S128A | 63% | 125% |  |
| T19A | 116% | 22% |  | L74A | 300% | 88% | + | E129A | 3% | 2% | * |
| Y20A | 163% | 65% |  | S75A | 267% | 65% |  | V130A | 57% | 42% |  |
| I21A | 20% | 157% |  | D76A | 163% | 33% |  | V131A | 148% | 118% |  |
| F22A | 2% | 1% | * | E77A | 155% | 61% |  | N132A | 113% | 83% |  |
| N23A | 180% | 84% |  | N78A | 80% | 39% |  | G133A | 113% | 78% |  |
| N24A | 74% | 85% |  | I79A | 93% | 42% |  | F134A | 93% | 67% |  |
| L25A | 86% | 116% |  | N80A | 125% | 82% |  | R135A | 118% | 46% |  |
| Y26A | 56% | 125% |  | V81A | 126% | 27% |  | E136A | 109% | 74% |  |
| I27A | 82% | 87% |  | S82A | 167% | 64% |  | I137A | 110% | 102% |  |
| N28A | 177% | 65% |  | V83A | 116% | 10% |  | N138A | 130% | 50% |  |
| D29A | 357% | 152% | + | I84A | 140% | 15% |  | Y139A | 84% | 18% |  |
| Y30A | 103% | 31% |  | T85A | 93% | 78% |  | S140A | 9% | 3% | * |
| K31A | 85% | 84% |  | I86A | 151% | 23% |  | D141A | 85% | 59% |  |
| M32A | 9% | 2% | * | S87A | 143% | 48% |  | E142A | 67% | 63% |  |
| F33A | 129% | 93% |  | D88A | 146% | 112% |  | F143A | 9% | 3% | * |
| W34A | <1% | 2% | * | S89A | 93% | 102% |  | L144A | 30% | 10% |  |
| I35A | <1% | 3% | * | F90A | 389% | 108% | + | K145A | 35% | 54% |  |
| D36A | 73% | 11% |  | I91A | 66% | 42% |  | V146A | <1% | 5% | * |
| S37A | 98% | 39% |  | R92A | 63% | 46% |  | F147A | <1% | 2% | * |
| G38A | <1% | 3% | * | S93A | 179% | 77% |  | F148A | <1% | 2% | * |
| I39A | 143% | 64% |  | L94A | 22% | 5% |  | S149A | 171% | 76% |  |
| K41 | 145% | 172% |  | K95A | 80% | 84% |  | G150A | 36% | 3% |  |
| L42A | 1% | 4% | * | S96A | 200% | 110% |  | F151A | <1% | 3% | * |
| I43A | 84% | 68% |  | Y97A | 46% | 13% |  | F152A | <1% | 2% | * |
| D44A | 442% | 53% | + | I98A | 54% | 39% |  | S153A | 44% | 55% |  |
| K45A | 166% | <1% |  | L99A | 90% | 50% |  | K154A | 113% | 108% |  |
| N46A | 87% | 166% |  | G100A | 80% | 6% |  | V155A | 122% | 82% |  |
| C47A | 123% | 10% |  | D101A | 46% | 22% |  | E156A | 49% | 16% |  |
| L48A | 55% | 35% |  | L102A | 146% | 46% |  | K157A | 109% | 1% |  |
| V49A | 15% | 45% |  | M103A | 303% | 44% | + | K158A | 112% | 87% |  |
| S50A | 149% | 25% |  | I104A | 44% | 14% |  | Y159A | 179% | 1% |  |
| Y51A | 467% | 201% | + | R105A | 320% | 54% | + | N160A | 278% | 352% | + |
| E52A | <1% | 2% | * | N106A | 396% | 93% | + | S161A | 196% | 110% |  |
| I53A | 86% | 75% |  | L107A | <1% | 9% | * | I162A | 115% | 79% |  |
| N54A | 77% | 67% |  | Y108A | 88% | 30% |  | F163A | 78% | 27% |  |

TABLE 1-continued

Effect of Alanine Substitutions in the ToxT N-terminus on transcriptional activity

| mutation | ctxAp-lacZ | acfA-phoA | class[a] | mutation | ctxAp-lacZ | acfA-phoA | class[a] | mutation | ctxAp-lacZ | acfA-phoA | class[a] |
|---|---|---|---|---|---|---|---|---|---|---|---|
| S55A | 93% | 42% | | S109A | 89% | 117% | | I164A | 52% | 60% | |
| S56A | 166% | 42% | | E110A | 99% | 79% | | | | | |

[a]class: * <10% WT activity in both ctxAp-lacZ and acfA-phoA assays; + >300% WT activity in either ctxAp-lacZ or acfA-phoA assays

TABLE 2

Effect of Alanine Substitutions in the ToxT C-terminus on transcriptional activity

| mutation | ctxAp-lacZ | acfA-phoA | class[a] | mutation | ctxAp-lacZ | acfA-phoA | class[a] | mutation | ctxAp-lacZ | acfA-phoA | class[a] |
|---|---|---|---|---|---|---|---|---|---|---|---|
| T165A | 34% | 19% | | L202A | 2% | 1% | * | K237A | <1% | <1% | * |
| D166A | 73% | 42% | | K203A | <1% | 6% | * | Q238A | 118% | 93% | |
| D167A | 28% | 36% | | K204A | 99% | 84% | | I239A | 111% | 13% | |
| L168A | 25% | 25% | | E205A | 31% | 56% | | Y241A | <1% | 1% | * |
| D169A | 23% | 26% | | L206A | <1% | 1% | * | Q242A | 76% | 56% | |
| M171A | 190% | 146% | | E207A | 282% | 64% | | S243A | 107% | 68% | |
| E172A | 73% | 41% | | S208A | 17% | 61% | | G244A | <1% | <1% | * |
| K173A | 144% | 95% | | R209A | 211% | 81% | | F245A | <1% | <1% | * |
| I174A | <1% | 1% | * | G210A | 81% | 33% | | S247A | 33% | 4% | |
| S175A | 4% | 3% | * | V211A | <1% | 1% | * | V248A | 7% | 25% | |
| C176A | 42% | 96% | | K212A | 157% | 49% | | S249A | 199% | 4% | |
| L177A | 17% | 7% | | F213A | 26% | 2% | | Y250A | 23% | <1% | |
| V178A | 3% | <1% | * | R214A | <1% | 2% | * | F251A | <1% | <1% | * |
| K179A | 108% | 127% | | E215A | 40% | 67% | | S252A | 114% | 168% | |
| S180A | 100% | 102% | | L216A | 32% | 3% | | T253A | 3% | 1% | * |
| D181A | 109% | 4% | | I217A | <1% | <1% | * | V254A | 102% | 44% | |
| I182A | <1% | 34% | | N218A | 188% | 119% | | F255A | <1% | <1% | * |
| T183A | 415% | 117% | + | S219A | 186% | 118% | | K256A | 20% | 10% | |
| R184A | <1% | <1% | * | I220A | 21% | 17% | | S257A | <1% | <1% | * |
| N185A | 152% | 112% | | R221A | <1% | 1% | * | T258A | 100% | 93% | |
| W186A | <1% | <1% | * | I222A | 112% | 27% | | M259A | 6% | 6% | * |
| R187A | 107% | 14% | | S223A | 63% | 103% | | N260A | <1% | <1% | * |
| W188A | <1% | <1% | * | Y224A | 36% | 2% | | V261A | 103% | 121% | |
| D190A | 1% | 3% | * | S225A | 45% | 116% | | P263A | 63% | 14% | |
| I191A | 2% | <1% | * | I226A | 41% | 3% | | S264A | 170% | 24% | |
| C192A | 54% | 55% | | S227A | 8% | 1% | * | E265A | 91% | 67% | |
| G193A | 99% | 72% | | L228A | 34% | 5% | | Y266A | 81% | 7% | |
| E194A | 266% | 46% | | M229A | 22% | 3% | | L267A | 96% | 65% | |
| L195A | 50% | 2% | | K230A | 195% | 93% | | F268A | 58% | 58% | |
| R196A | 90% | 35% | | T231A | 63% | 17% | | M269A | 130% | 32% | |
| T197A | 167% | 69% | | G232A | 132% | 41% | | L270A | 149% | 24% | |
| N198A | 143% | 64% | | E233A | <1% | 2% | * | T271A | 105% | 80% | |
| R199A | 26% | 2% | | F234A | 52% | 9% | | G272A | 106% | 73% | |
| M200A | 72% | 95% | | K235A | 122% | 64% | | V273A | 61% | 81% | |
| I201A | 77% | 78% | | I236A | 1% | <1% | * | E275A | 101% | 59% | |
| | | | | | | | | K276A | 146% | 49% | |

[a]class: * <10% WT activity in both ctxAp-lacZ and acfA-phoA assays; + >300% WT activity in either ctxAp-lacZ or acfA-phoA assays A total of 20 Ala substitutions in the N-terminus led to <10% wildtype transcriptional activity at the ctxA promoter (Table 1). Six phenylalanine residues (F22, F143, F147, F148, F151, and F152), five leucine residues (L42, L60, L107, and L127), both tryptophan residues (W34 and W117), two glutamate residues (E52 and E129), and one valine (V146), methionine (M32), glycine (G38), isoleucine (I35), and serine (S140) residue within the N-terminus were found to be important for ctxA transcription. All of these mutations also significantly decreased AcfA-PhoA expression in *V. cholerae* (see below). These results point out the importance of hydrophobic residues within the N-terminus for ctxA transcriptional activation, as 16 of the 20 mutations lie in L, F, I, W, V, or M residues.

Interestingly, 12 Ala substitutions in the N-terminus led to >300% wildtype transcriptional activity at the ctxA promoter (Table 1). Three of these were replacements of leucine residues (L61, L74, and L114), two replaced aspartate residues (D29 and D44), and two replaced arginine residues (R68 and R105), while the rest replaced tyrosine (Y51), phenylalanine (F90), asparagine (N106), methionine (M103), and lysine (K112). An additional Ala substitution at N160 caused almost 300% wildtype transcriptional activity at the ctxA promoter; this mutation is also included here because of a similar effect on acfA-phoA expression. These mutants demonstrate that "wildtype" transcriptional activity of ToxT is not maximal, and support the hypothesis that ToxT activity is normally modulated within the cell (Schuhmacher and Klose, 1999).

A total of 30 Ala substitutions in the C-terminus led to <10% wildtype transcriptional activity at the ctxA promoter (Table 2). Five isoleucine residues (I174, I182, I191, I217, and I236), three phenylalanine residues (F245, F251, and F255), three valine residues (V178, V211, and V248), three arginine residues (R184, R214, and R221), three serine residues (S175, S227 and S257), both tryptophan residues (W186 and W188), two leucine residues (L202 and L206), two lysine residues (K203 and K237), and one aspartate (D190), threonine (T253), glutamate (E233), glycine (G244), tyrosine (Y241), methionine (M259), and asparagine (N260) residue within the C-terminus were found to be important for ctxA transcription. Only two of these mutations (I182A, V248A) did not also significantly decrease AcfA-PhoA expression in *V. cholerae* (see below). Also, one Ala substitution, at threonine 183, in the C-terminus led to >300% wildtype transcriptional activity at the ctxA promoter. This "hyperactive" mutant again supports that ToxT activity is normally modulated within the cell (Schuhmacher and Klose, 1999).

Example 3

ToxT Amino Acids Necessary for AcfA-PhoA Expression

ToxT binds to the acfA promoter at a region −77 to −49 relative to the acfA transcription startsite (Withey and DiRita, 2005). ToxT activates acfA transcription, as well as the divergently transcribed gene, acfD, from this binding region. Two toxbox sequences can be found in this protected region in an inverted orientation (Withey and DiRita, 2006), and it has been shown that ToxT binding to both toxbox motifs is necessary for acfA activation.

A ΔtoxT *V. cholerae* strain (Champion et al., 1997) was that contains a chromosomal acfA-phoA translational fusion was utilized. All 267 Ala substitution ToxT mutants were expressed in this reporter strain and assayed for alkaline phosphatase activity. Each Ala substitution mutant was tested independently at least twice, with triplicate samples. The native MBP-ToxT protein was also assayed each time with every experiment, to allow a direct comparison of the levels of activity of the mutant and native proteins and eliminate any experiment-to-experiment variations in absolute alkaline phosphatase activity. The results are summarized in FIG. 1 and shown in Table 1 for Ala substitution mutants within the N-terminus (aa 1-164), and summarized in FIG. 2 and shown in Table 2 for Ala substitution mutants within the C-terminus (aa 165-276). Activation of AcfA-PhoA activity for each mutant is reported as % activity of the native ToxT protein. Many mutations caused modest increases or decreases in ToxT-dependent activation, but these alterations were only considered significant if the activity was either <10% or >300% that of the native protein; all of these differences were deemed significant (p<0.001) utilizing Students 2-tailed t test.

A total of 30 Ala substitutions in the N-terminus led to <10% wildtype activation of AcfA-PhoA activity (Table 1). Notably, more N-terminal aa were required for AcfA-PhoA activation than for ctxA transcription. Twenty of the N-terminal Ala substitution mutations that led to reductions in AcfA-PhoA activity were also shown to cause reductions in ctxA transcription (designated with an asterix in Table 1 and FIG. 1: F22A, M32A, W34A, I35A, G38A, L42A, E52A, L60A, L71A, L107A, W117A, L127A, E129A, S140A, F143A, V146A, F147A, F148A, F151A, and F152A). These residues were considered to be critical for the "core" functions of ToxT and these mutations were studied further. In addition, three lysine residues (K45, K62, K157), two phenylalanine residues (F7, F69), two glycine residues (G100, G150), and one isoleucine (I58), one leucine (L94), and one tyrosine (Y159) residue within the N-terminus were found to be important for AcfA-PhoA activation but not ctxA transcription.

Six Ala substitutions in the N-terminus led to >300% wildtype activation of AcfA-PhoA (Table 1). Only one of these Ala substitutions (L61A) also led to >300% wildtype transcription of ctxA, although a second (N160A) led to close to 300% wildtype levels of ctxA transcription (denoted with # in FIG. 1). The other four mutations were replacements of phenylalanine (F17), asparagine (N64), serine (S65), and isoleucine (I66). It is of interest that the aa residues 64-66 have a dramatic influence on AcfA expression but essentially no effect on ctxA transcription.

A total of 43 Ala substitutions in the C-terminus led to <10% wildtype activation of AcfA-PhoA activity (Table 2). Notably, more C-terminal aa were required for AcfA-PhoA activation than for ctxA transcription. Twenty-eight of the C-terminal Ala substitution mutations that led to reductions in AcfA-PhoA activity were also shown to cause reductions in ctxA transcription (designated with an asterisk in Table 2 and FIG. 2: I174A, S175A, V178A, R184A, W186A, W188A, D190A, I191A, L202A, K203A, L206A, V211A, R214A, I217A, R221A, S227A, E233A, I236A, K237A, Y241A, G244A, F245A, F251A, T253, F255A, S257A, M259A, and N260A). These residues were considered to be critical for the "core" functions of ToxT and these mutations were studied further. In addition, four leucine residues (L177, L195, L216, L228), three tyrosine residues (Y224, Y250, Y266), two serine residues (S247, S249), two phenylalanine residues (F213, F234), and one arginine (R199), methionine (M229), isoleucine (I226), and aspartate (D181) residue within the C-terminus were found to be important for AcfA-PhoA activation but not ctxA transcription.

No Ala substitutions were found in the C-terminus that led to >300% wildtype activation of AcfA-PhoA; interestingly the Ala substitution within this region that led to >300% wildtype ctxA transcription had little effect on AcfA-PhoA activation (T183A).

Example 4

ToxT Amino Acids Necessary for Virulence Factor Expression in *V. cholerae*

ToxT activates transcription of the genes encoding the two major virulence factors, CT and TCP, in *V. cholerae* by activating the ctxA and tcpA promoters. To confirm the importance of the ToxT amino acids identified above utilizing ctxA-lacZ transcriptional fusion and AcfA-PhoA translational fusion reporters, the mutant ToxT alleles were measured for their ability to activate virulence factor expression in *V. cholerae*. The plasmids expressing the 48 Ala substitution mutants that showed <10% WT activity in both ctxA transcription and AcfA-PhoA expression (denoted with asterisks in FIGS. 1-2 and Tables 1-2) were transformed into the ΔtoxT *V. cholerae* strain VJ740 (Champion et al., 1997) and the strains were assayed for CT and TCP expression under growth conditions known to stimulate maximal virulence factor expression in this *V. cholerae* strain (30° C. in LB). CT expression was assayed via $GM_1$-ELISA, while TCP expression was measured by CTXφKan transduction (Example 12; Table 3). CTXφ utilizes the TCP as its receptor (Waldor and Mekalanos, 1996), thus CTXφKan transduction is a convenient means to measure TCP expression. The activity of all mutants was compared to that of the native ToxT assayed under identical conditions (Table 3).

TABLE 3

Virulence Factor Induction by Alanine Substitution ToxT Mutants

| ToxT Mutant | 30° C. | | | 37° C. | | | Mutant Class[a] |
|---|---|---|---|---|---|---|---|
| | CT (% WT) | TCP (% WT) | Full-length protein present | CT (% WT) | TCP (% WT) | Full-length protein present | |
| F22A | 63 | 6 | + | 220 | 0.7 | + | D1 |
| M32A | <1 | 0.4 | + | N.D.[b] | N.D. | N.D. | A |
| W34A | <1 | 2 | + | N.D. | N.D. | N.D. | B |
| I. I35A | <1 | 0 | + | N.D. | N.D. | N.D. | A |
| G38A | 52 | 6 | + | <1 | 0 | + | D1 |
| L42A | <1 | 0.2 | + | N.D. | N.D. | N.D. | A |
| E52A | 5 | 0 | + | N.D. | N.D. | N.D. | C |
| L60A | 5 | 9 | + | N.D. | N.D. | N.D. | D1 |
| II. L71A | <1 | 0 | + | N.D. | N.D. | N.D. | A |
| L107A | 71 | 0.3 | + | 1 | 0 | + | D1 |
| III. W117A | <1 | 0 | + | N.D. | N.D. | N.D. | A |
| IV. L127A | <1 | 0 | + | N.D. | N.D. | N.D. | A |
| E129A | 3 | 1 | + | N.D. | N.D. | N.D. | C |
| S140A | 21 | 0.1 | + | 2 | 0.001 | + | D1 |
| F143A | 11 | 77 | + | 2 | 0 | + | D2 |
| V146A | 96 | 234 | + | 9 | 0 | + | D2 |
| V. F147A | <1 | 0.03 | + | N.D. | N.D. | N.D. | A |
| VI. F148A | <1 | 0.003 | + | N.D. | N.D. | N.D. | A |
| F151A | <1 | 0 | + | N.D. | N.D. | N.D. | A |
| VII. F152A | <1 | 0.1 | + | N.D. | N.D. | N.D. | A |
| VIII. I174A | <1 | 0 | + | N.D. | N.D. | N.D. | A |
| S175A | 2 | 0.3 | + | N.D. | N.D. | N.D. | C |
| V178A | 5 | 2 | + | N.D. | N.D. | N.D. | D1 |
| IX. R184A | 29 | 9 | + | <1 | 0 | + | D1 |
| W186A | <1 | 0 | + | N.D. | N.D. | N.D. | A |
| W188A | <1 | 0 | + | N.D. | N.D. | N.D. | A |
| D190A | 97 | 214 | + | 18 | 0 | + | D2 |
| I191A | 74 | 60 | + | <1 | 0 | + | D2 |
| L202A | 105 | 22 | + | <1 | 0 | + | D2 |
| K203A | <1 | 182 | + | N.D. | N.D. | N.D. | B |
| L206A | <1 | 0.2 | + | N.D. | N.D. | N.D. | A |
| X. V211A | <1 | 0 | + | N.D. | N.D. | N.D. | A |
| R214A | 24 | 27 | + | 6 | 0 | + | D2 |
| I217A | <1 | 0 | + | N.D. | N.D. | N.D. | A |
| R221A | <1 | 0.002 | + | N.D. | N.D. | N.D. | A |
| S227A | 36 | 41 | + | <1 | 0 | + | D2 |
| E233A | 3 | 0.5 | + | N.D. | N.D. | N.D. | C |
| I236A | 25 | 130 | + | 2 | 0 | + | D2 |
| K237A | <1 | 26 | + | N.D. | N.D. | N.D. | B |
| Y241A | 59 | 335 | + | 17 | 0 | + | D2 |
| G244A | <1 | 0 | + | N.D. | N.D. | N.D. | A |
| XI. F245A | <1 | 0 | + | N.D. | N.D. | N.D. | A |
| F251A | <1 | 0 | + | N.D. | N.D. | N.D. | A |
| T253A | 2 | 0 | + | N.D. | N.D. | N.D. | C |
| F255A | <1 | 0 | + | N.D. | N.D. | N.D. | A |
| S257A | <1 | 3 | + | N.D. | N.D. | N.D. | B |
| M259A | 110 | 203 | + | 2 | 0.01 | + | D2 |
| XII. N260A | <1 | 0.1 | + | N.D. | N.D. | N.D. | A |
| "hyperactive" mutants | | | | | | | |
| L61A | 398 | 94 | + | N.D. | N.D. | N.D. | E |
| N160A | 395 | 151 | + | N.D. | N.D. | N.D. | E |

[a]Mutant Class: Class A ≦1% WT CT, ≦1% WT TCP; Class B ≦1% WT CT, >1% WT TCP; Class C >1% WT CT, ≦1% WT TCP; Class D >1% WT CT, >1% WT TCP (Class D2 >10% WT CT AND >10% WT TCP); Class E >300% WT CT
[b]N.D. Not Determined The 48 Ala substitution ToxT mutants that showed significant decreases in both ctxA transcription and AcfA-PhoA expression in reporter assays fell into four general classes of CT and TCP expression, when expressed in ΔtoxT *V. cholerae* under in vitro virulence inducing conditions for this strain. In the first class (Class A, Table 3), the mutants stimulated little to no detectable CT expression (≦1% WT CT expression) and little to no detectable TCP expression (≦1% WT TCP expression); the majority of the mutants (22 total) fell into this class (M32A, I35A, L42A, L71A, W117A, L127A, F147A, F148A, F151A, F152A, I174A, W186A, W188A, L206A, V211A, I217A, R221A, G244A, F245A, F251A, F255A, N260A). These 22 residues were considered to be essential to the function of ToxT.

In the second class (Class B, Table 3), the mutants stimulated low to no levels of CT expression (≦1% WT CT expression) but detectable to high levels of TCP expression (>1% WT TCP expression); 4 of the mutants fell into this class (W34A, K203A, K237A, S257A). Only two of these mutants (K203A and K237A) expressed high levels (>10% WT expression) of TCP; the other two residues within this class (W34 and S257) were considered to be critical for the function of ToxT. In the third class (Class C, Table 3), the mutants stimulated low to no levels of TCP expression (≦1% WT TCP expression) but detectable levels of CT expression (>1% WT CT expression); five mutants fell into this class (E52A, E129A, S175A, E233A, and T253A). CT expression was still relatively low in this class of mutants (≦5% WT CT expression), so these residues were considered to be critical for the function of ToxT.

The fourth class of mutants (Class D, Table 3) stimulated high to wildtype levels of CT expression (>1% WT CT expression) and high to wildtype levels of TCP expression (>1% WT TCP expression); 17 mutants fell into this class. This class could be further subdivided (Class D1) into the 7 mutants that had lower levels (<10% WT activity) of CT and/or TCP (F22A, G38A, L60A, L107A, S140A, V178A, and R184A), and the 10 mutants (Class D2) that had close to wildtype levels (>10% WT activity) of both CT and TCP (F143A, V146A, D190A, I191A, L202A, R214A, S227A, I236A, Y241A, and M259A). Notably, five mutations in Class D1 (F22A, G38A, L107A, S140A, and R184A) stimulated >10% WT CT activity, but <10% WT TCP activity. The other 2 residues in Class D1 that, when mutated, led to the stimulation of >1% but <10% WT CT and TCP expression (L60A and V178A) were considered to be critical for ToxT function.

For the 15 mutants that showed >10% WT CT expression (five in Class D1 and ten in Class D2), the assay conditions may have been responsible for the apparent discrepancy between low ctx transcription (assayed at 37° C. in Tables 1-2) and high CT expression (assayed at 30° C.). These mutants may represent temperature sensitive alleles that exhibit lower activity at 37° C. than at 30° C. (Schuhmacher and Klose, 1999). These 15 mutants were also assayed for CT and TCP expression in the ΔtoxT $V.$ cholerae strain at 37° C., and compared to the levels induced by the native ToxT at this temperature (Table 3). Twelve of the fifteen mutant ToxT proteins (G38A, L107A, S140A, F143A, V146A, R184A, I191A, L202A, R214A, S227A, I236A, and M259A) that stimulated >10% CT expression at 30° C. stimulate <10% WT CT expression at 37° C. These mutants also stimulated low to no detectable TCP expression at this temperature (<1% WT TCP expression). Two additional mutants (D190A, Y241A) expressed lower levels of CT at 37° C. than at 30° C., although the levels were still >10% WT activity; most notably these mutants stimulated no detectable TCP expression at 37° C. Another mutant (F22A) stimulated high levels of CT expression at both 30° C. and 37° C., but exhibited temperature sensitive stimulation of TCP expression (<1% WT activity at 37° C., >1% WT activity at 30° C.). Given the high level CT expression at both temperatures, it is not clear why this mutant was identified in the initial screen. These 15 mutations were considered to represent temperature sensitive mutations.

The two Ala substitution mutants (L61A and N160A) that showed close to or greater than 300% WT activity in both ctx transcription and AcfA-PhoA expression ("hyperactive" mutants designated with # in FIG. 1) were also assayed for CT and TCP expression in the ΔtoxT $V.$ cholerae strain under in vitro virulence inducing conditions (Table 3, Class E). These mutant proteins stimulated >300% WT CT expression, but no apparent increase in TCP expression above WT levels. Whole cell lysates from these strains were also assayed by Western immunoblot with antisera to TcpA, the pilus subunit, which revealed similar amounts of TcpA produced by the wildtype and both mutant strains (data not shown). These results indicate that the Ala substitutions at L61 and N160 increase transcriptional activity of ToxT at some, but not all, ToxT-dependent promoters.

To verify that the reduced activities of the Ala substitution ToxT mutants that exhibit low ctxA and acfA activation is not due to reduced protein stability, whole cell lysates were prepared from each ΔtoxT $V.$ cholerae strain carrying the 48 Ala substitution mutant proteins under the conditions assayed (either 30° C. or 37° C.). ToxT protein was visualized by Western immunoblot with antisera against MBP, since MBP is fused to the N-terminus. All of the 48 Ala substitution mutant ToxT proteins were detected as full-length proteins at levels similar to that of the native protein in the ΔtoxT $V.$ cholerae strain at 30° C., and the 15 assayed at 37° C. were also detected as full-length proteins at levels similar to that of the native protein (Table 3), demonstrating that these mutations alter ToxT activity rather than ToxT expression/stability.

Example 5

ToxT Amino Acids Involved in Dimerization

The capacity of the ToxT N-terminus to dimerize the monomeric DNA-binding domain of LexA, which facilitates the repression of sulA transcription, has been previously characterized (Prouty et al., 2005). These results are consistent with the presence of dimerization determinants located within the ToxT N-terminus, as has been demonstrated by the same technique for the AraC N-terminus (Bustos and Schleif, 1993). It is likely that some of the Ala substitutions within the N-terminus that cause decreases in ToxT activity might disrupt dimerization. The 20 Ala substitutions in the N-terminus that caused decreases in both ctxA transcription and AcfA-PhoA expression (denoted by asterisks in Table 1 and FIG. 1) were introduced into the MBP-ToxT$^N$-LexA expression plasmid pKEK522 (Prouty et al., 2005) by site-directed mutagenesis. The resultant fusion proteins were assayed for their ability to dimerize using an $E.$ coli sulA-lacZ transcriptional fusion reporter strain (Lin and Little, 1989).

In the absence of LexA-mediated repression, the $E.$ coli sulA-lacZ transcriptional fusion reporter strain expresses high levels of β-galactosidase activity (0% repression), whereas when the MBP-ToxT$^N$-LexA fusion protein is expressed, β-galactosidase activity is repressed (normalized to 100% WT repression). For clarity, the results are presented as % "WT" repression (native ToxT$^N$-LexA fusion), to emphasize any mutations that may cause defects in this activity. Most of the 20 Ala substitutions introduced into the MBP-ToxT$^N$-LexA fusion protein caused repression of the sulA-lacZ reporter relatively similar to the native fusion protein, indicating little deleterious effect on ToxT dimerization. However, one Ala substitution mutant fusion protein (F151A) was defective for repression of sulA transcription (>50% decrease in repression compared to the WT ToxT$^N$-LexA protein; p<0.001). Mutations at L107 and F152 caused decreases in repression as well, but the effect was <50% decrease (62% and 66% WT repression); these residues likely contribute to dimerization to a lesser degree than F151. The F151A mutant fusion protein was expressed at levels equivalent to that of the native fusion protein, as determined by Western immunoblot with MBP antisera (data not shown). F151 is located in a region of predicted alpha helical structure that roughly corresponds with the dimerization helix of the structurally similar AraC, and thus this result is consistent with this region contributing to ToxT dimerization.

Example 6

ToxT Amino Acids Involved in DNA Binding

The two helix-turn-helix (HTH) motifs of AraC family proteins, such as those in the C-terminus of ToxT, are predicted to allow the protein to bind DNA at specific sites (Gallegos et al., 1997). The recognition helices of both HTH motifs (corresponding to helices 3 and 6 of MarA; FIG. 2) make specific contacts with basepairs and the phosphate backbone in the cocrystal structure of MarA bound to DNA. Studies of other AraC-like proteins have also demonstrated the importance of one or both HTH motifs in making specific contacts with DNA (Gallegos et al., 1997; Rhee et al., 1998; Kwon et al., 2000).

Figure 4:
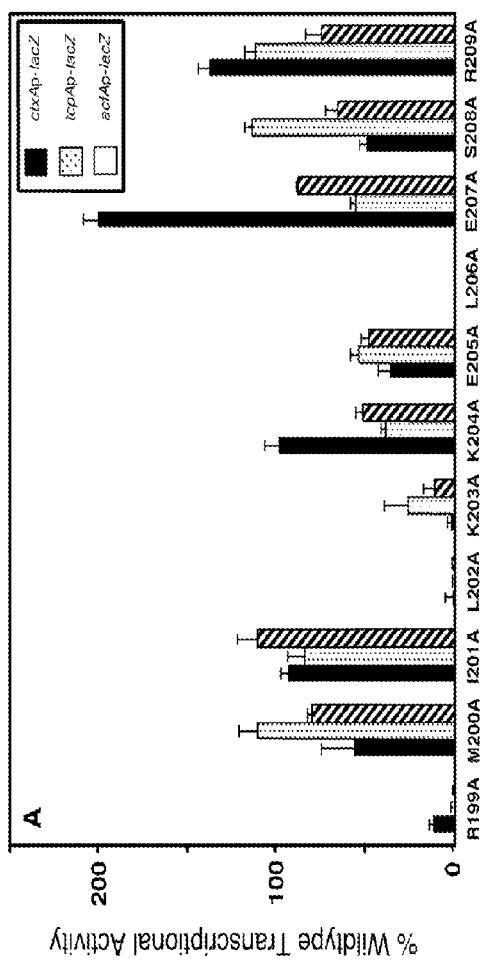
FIG. 4: Effect of Ala substitutions in the two putative DNA recognition helices on ToxT-dependent transcription. Strains of *S. typhimurium* containing chromosomal ctxAp-lacZ (KK201), tcpAp-lacZ (KK226), and acfAp-lacZ (KK734) transcriptional fusions and expressing the MBP-ToxT proteins with Ala substitutions in (A). "helix 3" (aa 199-209) and (B). "helix 6" (aa 248-259) were assayed for β-galactosidase activity. Results are the averages and standard deviation of three samples.
Figure 4:
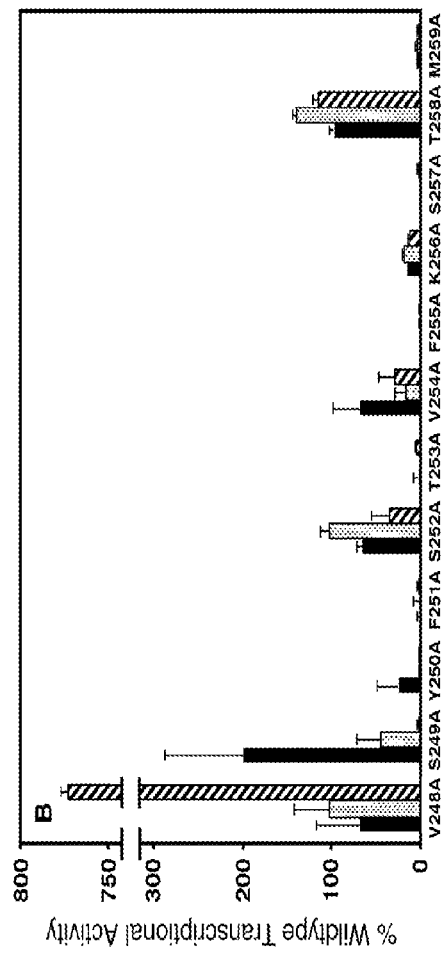

Ala substitutions of amino acids within one or both HTH motifs responsible for specific basepair contacts would likely result in differential activation of the ctxA, tcpA, or acfA promoters, due to differences in the ToxT binding sites at these promoters. S. typhimurium reporter strains containing lacZ transcriptional fusions to the acfA and tcpA promoters were created and transformed, along with the S. typhimurium ctxA-lacZ reporter strain, with the ToxT mutants containing Ala substitutions in the predicted recognition helices of the two HTH domains (aa 199-209 and aa 248-259). The Ala substitution mutants were then assayed for their ability to activate these three promoters (FIG. 4). Since all three promoters were assayed in the same heterologous reporter strain, this should eliminate any strain- or reporter-specific differences.

Ala substitution mutants within the putative recognition helices HTH1 and HTH2 showed several patterns of transcriptional activity at the three different promoters, using 10% WT activity as a cutoff for "significant" activity. The first pattern of generally decreased activity at all three promoters (<10% WT activity) was seen in HTH1 with L202A and L206A, and in HTH2 with F251A, T253A, F255A, S257A, and M259A. Using this criteria to determine the relative importance of the two HTH domains, it appears that residues within HTH2 are more important than HTH1 for transcriptional activation. The second pattern of generally "wildtype" activity at all three promoters (>10% WT activity) was seen in HTH1 with M200A, I201A, K204A, E205A, E207A, S208A, and R209A, and in HTH2 with V248A, S252A, V254A, K256A, and T258A. The third pattern of differential activity at the promoters, with <10% WT activity at one or two promoters and >10% WT activity at the other promoters, was seen in HTH1 with R199A (>10% ctxA activity, <10% tcpA and acfA activity) and K203A (<10% ctxA and acfA activity, >10% tcpA activity), and in HTH2 with S249A (<10% acfA activity, >10% ctxA and tcpA activity) and Y250A (>10% ctxA activity, <10% tcpA and acfA activity). The pattern exhibited by K203A in these transcriptional assays is consistent with low CT and high TCP expression stimulated by this mutant protein in ΔtoxT V. cholerae (Table 3).

To determine whether the differential transcriptional activation observed above for mutants in HTH1 (K203A) and HTH2 (S249A) was due to differential binding to the ToxT binding sites in these promoters, DNA binding assays were utilized. Because these two Ala substitutions caused >10% WT activation of the tcpA promoter but <10% WT activation of the acfA promoter, it was hypothesized that these mutations may decrease binding to the acfA but not the tcpA promoter. The capacity of the ToxT C-terminus fused to a heterologous dimerization domain (the C/EBP leucine zipper) to bind the tcpA promoter and cause a shifted species in a gel mobility shift assay has been previously characterized (Prouty et al., 2005). The K203A and S249A mutations were introduced into the MBP-C/EBP-ToxT$^C$ expression plasmid pKEK544 (Prouty et al., 2005) by site-directed mutagenesis, and the resultant proteins were purified and utilized in gel mobility shift assays. The $^{32}$P-labelled DNA probes were generated by annealing complimentary oligonucleotides containing the toxbox binding motifs previously identified within the tcpA and acfA promoters (Withey and DiRita, 2005; Withey and DiRita, 2006).

Figure 5:
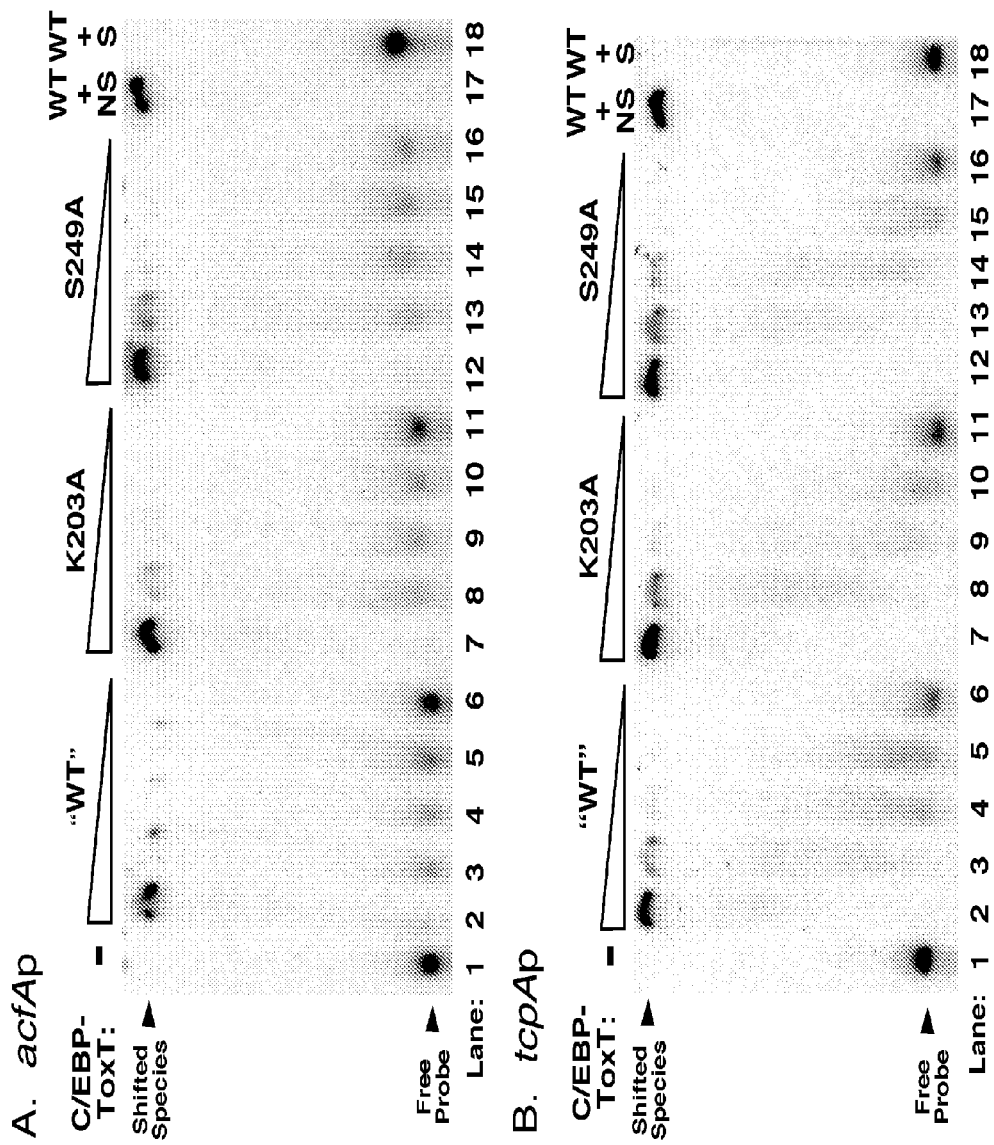
FIG. 5: DNA binding of K203A and S249A mutant proteins. Electrophoretic mobility shift assay for binding to $^{32}$P-labeled (A). acfAp and (B). tcpAp promoter fragments by purified MBP-C/EBP-ToxT$^C$ ("WT"), and MBP-C/EBP-ToxT$^C$ containing K203A ("K203A") and S249A ("S249A") mutations. Mobility shift assays were performed as described in the Examples with either no protein added (lanes 1), or identical three-fold decreasing concentrations (6.75, 2.25, 0.75, 0.25, and 0.083 nM) of MBP-C/EBP-ToxT$^C$ (lanes 2-6), MBP-C/EBP-ToxT$^C$K203A (lanes 7-11) and MBP-C/EBP-ToxT$^C$S249A (lanes 12-16). An excess of specific competitor (lane 17, 3 ng) or an excess of non-specific competitor (lane 18, 3 ng) was added to reactions that also contained 27 nM MBP-C/EBP-ToxT$^C$.

The "wildtype" MBP-C/EBP-ToxT$^C$ fusion protein and the MBP-C/EBP-ToxT$^C$ carrying the K203A and S249A mutations were matched by concentration, and dilutions subjected to gel mobility shift assay with the acfA and tcpA binding sites. The results shown in FIG. 5A demonstrate that the MBP-C/EBP-ToxT$^C$ fusion protein is able to specifically bind to the acfA promoter, as we have previously shown for the tcpA promoter (Prouty et al., 2005). Moreover, the K203A and S249A mutations did not significantly alter DNA binding to the acfA binding site, as the binding pattern was similar for all three proteins. The K203A and S249A mutations did not significantly alter DNA binding of the MBP-C/EBP-ToxT$^C$ protein to the tcpA binding site either (FIG. 5B). Addition of excess cold non-specific competitor ("WT+NS"; lane 17) was unable to affect the gel mobility shift of either fragment, whereas the addition of excess cold specific competitor ("WT+S"; lane 18) resulted in unshifted probe, demonstrating that the assay is measuring specific DNA binding. These results suggest that the differential transcriptional activation seen by the K203A and S249A mutants is not due to differential binding, but rather due to some other aspect of transcriptional activation.

Example 7

Amino Terminal Residues Required for Transcriptional Activation: Tertiary Structure and Dimerization The 3-dimensional structure of the ToxT N-terminus has not yet been solved, however secondary structure predictions (FIG. 1) suggest an initial region of predominantly beta sheet structure (aa 1-86) followed by a region of predominantly alpha helix (aa 87-164); the consensus secondary structure prediction was utilized to localize the important residues. 20 residues within the N-terminus were shown by our analysis to be important for transcriptional activation of the ctxA and acfA promoters. These residues were predominantly hydrophobic (16 were in L, F, I, W, V, or M residues), and were clustered in several regions of the N-terminus.

Nine of the mutations in the N-terminus were located in the predicted beta sheet region (aa 1-86). The critical residues F22, M32, W34, I35, L42, L60, and L71 are predicted to lie in the middle of α1, β2, β3, β5, and β6, and may represent buried hydrophobic residues that, when mutated, disrupt the local structure. The alanine substitution mutation in the putative turn region located between β2 and β3, G38A, caused a temperature sensitive phenotype, in that the mutant protein is able to activate significant CT expression at 30° C. but not 37° C. The last critical residue in the beta sheet region of the N-terminus, E52, lies within the putative β4, and due to its acidic nature would be predicted to be surface exposed; this residue is of interest for future studies of ToxT interactions with RNA polymerase and/or effector molecules.

Eleven of the mutations in the N-terminus were located in the alpha helical region (aa 87-164). Using the secondary structure prediction consensus as a guide, the majority of critical residues in this region (6 of 11) are clustered in α4, and 5 of these are phenylalanine residues.

The Ala substitution demonstrated to most adversely affect dimerization in the LexA-based assay system was F151A, located in α4, demonstrating this region's involvement in ToxT dimerization, while F152 and L107 also appeared to contribute to dimerization to a lesser extent. ClustalW primary sequence alignment between the AraC-like activators AraC, XylS, UreR, and ToxT, while admittedly weak in this region, aligns the ToxT α4 with known dimerization determinants of these other proteins. Specifically, F151 and F152 of ToxT align with L193 and L194 of XylS, F148 aligns with L147 of UreR, and F143 aligns with L151 of AraC, which have been shown to be important for XylS, UreR, and AraC dimerization, respectively (Soisson et al., 1997; Poore et al., 2001; Ruiz et al., 2003). It was speculated that hydrophobic interactions between the F residues on the antiparallel α4 helices of two ToxT monomers facilitate dimer formation.

Several additional residues in the alpha helical region of the N-terminus were also critical for ToxT-dependent transcription. Of these, L107A, located toward the end of the putative α2, deserves special consideration. We previously identified a mutation at this location, L107F, that allowed higher levels of transcription of tcpA in the presence of bile, which normally represses ToxT activity (Prouty et al., 2005). The L107F protein behaved similar to the "hyperactive" mutants identified in this study and discussed below (i.e., activity increased relative to the native protein); notably changing this residue to be more hydrophobic (L107F) increased ToxT activity while changing it to be less hydrophobic (L107A) decreased activity, illustrating the importance of hydrophobic interactions at this particular residue.

Example 8

Amino Terminal Residues that Negatively Regulate Transcription Activation: Environmental Modulation One of the findings resulting from comprehensive Ala scanning mutagenesis of ToxT was the identification of residues that apparently repress the activity of ToxT. Replacement of these residues with Ala stimulated ToxT transcription activation above that normally found in the native protein, suggesting that the "wildtype" level of ToxT activity is not the maximal level of activity, and consistent with the hypothesis that ToxT activity is normally modulated (Schuhmacher and Klose, 1999). Eighteen Ala substitution mutations that stimulated >300% WT transcriptional activity at ctxA and/or acfa were identified. Interestingly, 17 of the 18 residues are located within the N-terminus, illustrating the importance of the N-terminus in modulation of ToxT activity. Most of these mutations stimulated high levels of transcription at only one of the two promoters tested, but two mutations, L61A and N160A, stimulated high levels of transcription at both ctxA and acfA. Expression of these alleles within a ΔtoxT strain induced levels of CT higher than that stimulated by the wild-type ToxT, confirming that these proteins are "hyperactive" with regard to transcription activation of ctxA. It is not clear why substituting Ala for these two residues should stimulate ToxT activity. L61 is within the putative β5 and immediately adjacent to a residue that was shown to be critical for ToxT function, L60, while N160 is located within the putative linker region between the N- and C-termini and immediately downstream of α4.

The fifteen other N-terminal residues that when mutated, enhance ToxT activity, are not randomly distributed, but rather found mostly in two clusters within the N-terminus. These Ala substitutions also primarily stimulate transcription at the ctxA promoter (11 of 15), rather than at the acfA promoter (4 of 15). Since the majority of these mutations stimulate transcription in a promoter-specific manner, we suspect these regions represent an area of the protein that is involved in altering the conformation of ToxT into a more active state (e.g., enhancing dimerization, DNA binding, facilitating contact with RNAP, etc.). The region from residue 61-74 contains six of the "hyperactive" mutations (including L61A), and corresponds to the putative β5-β6 region. The three mutations in the middle of this region, N64A, S65A, and I66A, dramatically stimulated acfA transcription but had little effect on ctxA transcription, and thus represent a specific region of the protein that contributes to promoter-specific activation.

The region from residue 103-114 contains five of the "hyperactive" mutations, which corresponds to the end of α2 to β8. One of the residues in this region, L114, likely corresponds to the site of the mutation that provided resistance to virstatin as previously reported (Hung et al., 2005), based on the fact that an Ala substitution at this residue stimulated high levels of ctx transcription, and it was hypothesized that the Pro substitution at this site may have the same effect. These substitutions may allow for ToxT activity even in the presence of the inhibitor virstatin.

Example 9

Carboxy-Terminal Residues Required for Transcriptional Activation: Conserved Residues Involved in Tertiary Structure The 3-dimensional structures of two AraC family proteins, MarA and Rob, have been solved, and these structures are nearly superimposable (Rhee et al., 1998). Since these proteins share primary sequence homology with the ToxT C-terminus, along with all other AraC family proteins (FIG. 2), there is a reasonably good prediction of the structure of the ToxT C-terminus. The C-terminus is predicted to consist of seven alpha helices, with two subdomains that each contain a HTH motif (helices α2-α3 and α5-α6); these two subdomains are superimposable and joined by a relatively long helix (α4). The HTH motifs are predicted to protrude from the same face of the protein to allow binding to one face of the DNA.

28 residues within the C-terminus were shown by our analysis to be important for transcriptional activation of the ctxA and acfa promoters. The higher concentration of critical residues in the C-terminus compared to the N-terminus demonstrates the relative importance of this domain, which contains the DNA binding portion and likely also transcription activation determinants. Ten of these critical residues within the C-terminus are predicted to be buried within the hydrophobic core and thus important for maintaining structure; these are I174 and V178 within α1, I191A within α2, L202 and L206 in α3, I217 within α4, I236A in α5, and F251, F255, and M259 in α6. Two critical residues, W186, W188, along with two critical residues in α4, R214, and R21, are predicted to interact within a putative "hydrophobic pocket" located between the two HTH motifs. Most of the analogous residues in SoxS and MarA have been shown to be required for transcriptional activation at several promoters (Gillette et al., 2000; Griffith and Wolf, 2002).

Example 10

Carboxy-Terminal Residues Required for Transcriptional Activation: Residues Involved in Protein-Protein Interactions Of greatest interest to us are the residues of ToxT that are critical for its function but that are not well-conserved among other AraC family members, as these may illuminate ToxT-specific attributes. Those residues that fall into this category but that lie outside the DNA recognition helices will be addressed first. These include R184 in the α1-α2 linker, D190 in α2, V211 in the α3-α4 linker, S227 in α4, E233 in the α4-α5 linker, K237 and Y241 in α5, and N260 in the α6-α7 linker. All of these residues are predicted to be surface-exposed, and thus might be involved in protein-protein interactions (either within ToxT or with RNA polymerase) or protein-DNA interactions. Based on the crystal structure of DNA-bound MarA, it is possible that D190 is involved in DNA binding, but the other residues are not predicted to be involved in DNA binding or core hydrophobic interactions, suggesting they may be involved in protein-protein interactions.

For several AraC-like proteins that activate Class II promoters, residues that interact with sigma70 have been identified. In RhaR, RhaS, and MelR, an acidic residue (D or E) located at the position analogous to Q238 in ToxT makes direct contact with an arginine residue (R599) in sigma 70 (Wickstrum and Egan, 2004; Grainger et al., 2004). Protection of the ctxA promoter by ToxT extends all the way into the −35 element, at least at high concentrations (Yu and DiRita, 2002), indicating this may represent a Class II promoter. However, the lack of an acidic residue at position 238 argues against this possibility, and we suspect that ToxT binding at high concentrations overlapping the −35 element is not relevant to the mode of transcription activation at this promoter, suggesting that ctxAp also represents a Class I promoter.

Activation of Class I promoters by AraC family proteins involves contact with the C-terminal domain of the α subunit of RNAP. This type of activation is not yet well-characterized among this family of proteins, and no conserved residues have been identified that participate in αCTD contact. MarA and SoxS activate both Class I and Class II promoters, and no residues specific for Class I transcription activation were found in the comprehensive scanning alanine study of SoxS (Griffith and Wolf, 2002).

Example 11

Carboxy-Terminal Residues Required for Transcriptional Activation: Residues Involved in DNA Binding The defining characteristic of the AraC family of proteins is the two HTH motifs that facilitate DNA binding. The crystal structure of MarA bound to its binding site revealed that both recognition helices make specific contacts with the DNA, with each inserting into adjacent major grooves (Rhee et al., 1998). An alignment of ToxT with MarA and other AraC proteins (FIG. 2) predicts the two recognition helices to be located at aa199-209 (α3) and aa248-259 (α6); α3 in ToxT is one residue shorter than that found in the other activators. A comparison of transcription at three promoters (ctxA, tcpA, and acfA) with Ala substitution mutants in the two recognition helices revealed that 2 residues in α3 (L202 and L206) and 5 residues in α5 (F251, T253, F255, S257, and M259) were identified as being critical for ToxT function. Five of these residues, L202 and L206 in α3, and F251, F255, and M259 in α6, are predicted to be critical for the tertiary structure, as already discussed. This leaves two residues in α6 (T253 and S257) as potentially being critical for DNA binding at all three promoters. The residue analogous to T253 in MarA (R96) makes base-specific van der Waals interactions and hydrogen bonds with the mar binding site in the crystal structure (Rhee et al., 1998), and the corresponding Ala substitution mutants in MarA and SoxS (R96A and R90A) were defective for DNA binding and transcription activation at several promoters (Gillette et al., 2000; Griffith and Wolf, 2002). It is likely that T253 is also critical for base-specific van der Waals contacts and hydrogen bonds with the toxbox DNA binding site.

Several Ala substitutions in the recognition helices caused differential activation at the three promoters. In α3, K203A was defective at activating ctxA and acfA, but not tcpA. In α6, S249 was identified as being critical for acfa transcription but not ctxA or tcpA transcription. The analogous residues of MarA, Q45 and Q92, make van der Waals contacts to the DNA in the crystal structure. To determine whether K203 in α3 and S249 in α6 are involved in differential binding, gel mobility shift analysis with the ToxT C-terminus dimerized by the heterologous C/EBP leucine zipper domain was performed. This fusion protein is able to specifically bind to the toxbox sequences found in the acfa and tcpA promoters and cause a mobility shift, but the K203A and S249A mutations had little effect on this DNA binding activity. These results suggest that the low levels of acfa transcription induced by ToxT carrying these mutations is not due to lower DNA binding affinity for the acfA promoter.

Several predictions on ToxT DNA binding became apparent from this analysis. First, mutations in both helices diminished transcription activation, suggesting that both helices contribute to DNA binding. Second, mutations in HTH2 were more deleterious to transcription activation at all three promoters than mutations in HTH1, suggesting that the relative contribution of HTH2 to DNA binding is greater that that of HTH1. Third, two of the mutations in residues of α3 and α6 that had differential effects on transcription activation had no apparent effect on DNA binding, suggesting that differential activation of the various ToxT-dependent genes may not be due to differential binding to their respective promoters.

Example 12

Materials and Methods

Bacterial Strains—*Escherichia coli* strains DH5α (Hanahan, 1983) and Top10 (Invitrogen) were used for cloning, and JL1436 (Lin and Little, 1989) was used as the reporter strain for the LexA-based dimerization assay. The *Salmonella typhimurium* strain KK201 used for this study (putPA::[ctxAp::lacZYA]) has been described previously (Schuhmacher and Klose, 1999). The *S. typhimurium* strains KK734 (putPA::[acfAp::lacZYA]) and KK226 (putPA::[tcpAp::lacZYA]) were constructed as described (Elliott, 1992), utilizing plasmids pKEK936 and pKEK161. The ΔtoxT acfA::phoA *V. cholerae* strain KKV2095 was constructed by CPT1ts phage transduction (Hava and Camilli, 2001) of acfA::phoA from KP9.62 (Peterson and Mekalanos, 1988) into VJ740 (Champion et al., 1997).

Plasmids—The plasmids expressing MBP-ToxT from the pBAD promoter (pKEK160), MBP-ToxT$^N$-LexA from the plac promoter (pKEK522), and MBP-C/EBP-ToxT$^C$ from the plac promoter (pKEK544) have been described previously ((Prouty et al., 2005; Schuhmacher and Klose, 1999). Plasmids pKEK161 (tcpAp-lacZ) and pKEK936 (acfAp-lacZ) were created by PCR amplification utilizing primers tcpAp1 (5' GCGAATTCTATCATGAGCCGCCTAGATAG 3'; SEQ ID NO:3) paired with tcpAp2 (5' GCGGATCCGCATATT-TATGTAACTCCACCA 3'; SEQ ID NO:4), and acfAp1 (5' GCAGATCTTCGTAAACAAAAAAATTGCTG 3'; SEQ ID NO:5) paired with acfAp2 (5' GCGAATTCCGTCAAAGG-GAGCGGTAAATG 3'; SEQ ID NO:6); these fragments were subsequently digested with EcoRI and BamHI and ligated into pRS551 (Simons et al., 1987) similarly digested.

Scanning Alanine Mutagenesis—Site directed mutants were generated using the Quickchange Kit (Stratagene). Briefly, complementary oligonucleotides were designed that incorporated the desired codon change to alanine. Plasmids pKEK160, pKEK522, and pKEK544 (Schuhmacher and Klose, 1999) were used as templates for PCR reactions. PCR products were digested with DpnI and transformed into Top10 cells. Plasmids obtained from these transformed colonies were sequenced to confirm that the desired mutation was achieved prior to any further assays. In total, 267 codons of toxT in pKEK160 were altered to encode alanine, the additional 9 codons of toxT not altered already encode alanine or the initiating methionine.

Transcriptional Assays—Plasmids expressing MBP-ToxT with the various alanine substitutions were transformed into *S. typhimurium* strains KK201 (ctxAp-lacZ), KK226 (tcpAp-lacZ), or KK734 (acfAp-lacZ) and assayed for β-galactosidase activity by a previously described method (Miller, 1992). Plasmids expressing MBP-ToxT with the various alanine substitutions were also transformed into *V. cholerae* strain KKV2095 (ΔtoxT; acfA::phoA) and assayed for alkaline phosphatase activity by a previously described method (Miller, 1992). Overnight cultures were diluted 1:100 in LB broth plus 50 µg/ml ampicillin and 0.1% arabinose, grown at 37° C. to an optical density at 600 nm of 0.3 to 0.8, permeabilized with chloroform and sodium dodecyl sulfate, and then assayed for enzymatic activity. All assays were performed independently at least twice, with triplicate samples. The native MBP-ToxT protein was also assayed similarly in every experiment to allow direct comparison of mutant to native protein activities under identical experimental conditions. β-galactosidase and alkaline phosphatase activities are reported in Tables 1 and 2 as the percentage of activity of the native protein under identical conditions, this is an average of two independent experiments with triplicate samples.

Detection of Protein and Virulence Factor Expression—Expression of TCP was measured utilizing CTXφ$^{El\ Tor}$Kan as previously described (Prouty et al., 2005). Expression of MBP fusion proteins and TCP was detected by Western immunoblot of whole cell lysates with rabbit polyclonal antisera directed against either MBP (New England Biolabs) or TcpA (kind gift of J. Mekalanos), utilizing an ECL kit (Amersham Biosciences). CT expression was measured from culture supernatants by ganglioside $M_1$ enzyme-linked immunosorbent assay ($GM_1$-ELISA) with polyclonal rabbit serum directed against the purified B subunit of CT as described previously (Svennerholm and Holmgren, 1978)

DNA Binding Assay—MBP-C/EBP-ToxT$^C$ fusion proteins were purified as described previously (Prouty et al., 2005). tcpAp and acfAp probes were generated by first annealing complimentary oligonucleotides for each based on the following sequences that incorporate the toxboxes identified at these promoters (Withey and DiRita, 2006) (only the 5'-3' strand shown for each): tcpAp 5' TCAACGTAAGTGT-GTTATTAAAAAAATAAAAAAACACAG-CAAAAAATGAGA TCTGTC 3' (SEQ ID NO:7) and acfAp 5' TTTATGCTAACTCGTTAAATTTT-TAAAAATAAATTTAACAAAATGTATAAAGC GATTT 3' (SEQ ID NO:8). The double stranded probes were labeled utilizing polynucleotide kinase and $\gamma^{32}$P-ATP, then purified via a Stratagene NucTrap probe purification column. Purified proteins were mixed with labeled probe (20,000 cpm) and poly dIC (0.3 ng) in LSB (10 mM phosphate, 30 mM NaCl, 1 mM azide, 10 mM βME, 1 mM EGTA, pH 7.0), incubated for 10 minutes at 37° C. and loaded into a 5% acrylamide 0.06% bis-acrylamide gel. Gels were electrophoresed in a Tris-Glycine buffer (50 mM Tris Base, 100 mM glycine, pH 8.5) and subsequently visualized by autoradiography. For specific competitor DNA, unlabelled annealed probes were used, while an unlabelled PCR product of the cat gene was used for non-specific competitor DNA, as described previously (Prouty et al., 2005).

REFERENCES

The following references, to the extent that they provide exemplary procedural or other details supplementary to those set forth herein, are specifically incorporated herein by reference:

Behnde and Egan, *J. Bacteriol.*, 181:5185-5192, 1999.
Brown and Taylor, *Mol. Microbiol.*, 16:425-39, 1995.
Bustos and Schleif, *Proc. Natl. Acad. Sci. USA*, 90:5638-5642, 1993.
Champion et al., *Mol. Microbiol.*, 23:323-331, 1997.
Cuff et al., *Bioinformatics*, 14:892-3. 1998.
DiRita et al., *Proc. Natl. Acad. Sci. USA*, 88:5403-5407, 1991.
DiRita et al., *Proc. Natl. Acad. Sci. USA*, 93:7991-7995, 1996.
Elliott, *J. Bacteriol.*, 174:245-253, 1992.
Gallegos et al., *Microbiol. Mol. Biol. Rev.*, 61:393-410, 1997.
Geourjon and Deleage, *Comput. Appl. Biosci.*, 11:681-4, 1995.
Gill, *Biochemistry*, 15:1242-8, 1976.
Gillette et al., *J. Mol. Biol.*, 299:1245-1255, 2000.
Grainger et al., *Mol. Microbiol.*, 48:335-348, 2003.
Grainger et al., *Mol. Microbiol.*, 51:1297-1309, 2004.
Greenberg et al., *Proc. Natl. Acad. Sci. USA*, 87:6181-6185, 1990.
Griffith and Wolf, *J. Mol. Biol.*, 322:237-257, 2002.
Hanahan, *J. Mol. Biol.*, 166:557-80, 1983.
Hava and Camilli, *J. Microbiol. Methods*, 46:217-25, 2001.
Herrington et al., *J. Exp. Med.*, 168:1487-1492, 1988.
Hulbert and Taylor, *J. Bacteriol.*, 184:5529-5532, 2002.
Hung and Mekalanos, *Proc. Natl. Acad. Sci. USA*, 102:3028-3033, 2005.
Hung et al., *Science*, 310:670-4, 2005.
Jair et al., *J. Bacteriol.*, 177:7100-7104, 1995.
Jair et al., *J. Bacteriol.*, 178:2507-2513, 1996.
Kwon et al., *Nature Struct. Biol.*, 7:424-430, 2000.
Lee et al., *Cell*, 99:625-634, 1999.
Lin and Little, *J. Mol. Biol.*, 210:439-452, 1989.
Martin and Rosner, *Curr. Opin. Microbiol.*, 4: 132-137, 2001.
Martin et al., *Mol. Microbiol.*, 34:431-441, 1999.
McGuffin et al., *Bioinformatics*, 16:404-5, 2000.
Mekalanos et al., *Nature*, 306:551-557, 1983.
Miller, In: *A Short Course in Bacterial Genetics*, 2$^{nd}$ Ed., Cold Spring Harbor Laboratory Press, Plainview, N.Y., 1992.
Mukhopadhyay et al., *J. Bacteriol.*, 183:4737-46, 2001.
Niland et al., *J. Mol. Biol.*, 264:667-674, 1996.
Ouali and King, *Protein Sci.*, 9:1162-76, 2000.
Pearson et al., *Proc. Natl. Acad. Sci. USA*, 79:2976-80, 1982.

Peterson and Mekalanos, *Infect. Immun.*, 56:2822-2829, 1988.
Poore et al., *J. Bacteriol.*, 183:4526-4535, 2001.
Porter and Dorman, *J. Bacteriol.*, 184:531-539, 2002.
Prouty et al., *Mol. Microbiol.*, 58:1143-1156, 2005.
Rhee et al., *Proc. Natl. Acad. Sci. USA*, 95:10413-10418, 1998.
Rosenberg et al., *Mol. Microbiol.*, 48:1609-1619, 2003.
Ruiz et al., *J. Bacteriol.*, 185:3036-41, 2003.
Schuhmacher and Klose, *J. Bacteriol.*, 181:1508-1514, 1999.
Shi et al., *J. Mol. Biol.*, 310:243-257, 2001.
Simons et al., *Gene*, 53:85-96, 1987.
Soding et al., *Nucl. Acids Res.*, 33:244-248, 2005.
Soisson et al., *Science*, 276:421-425, 1997.
Svennerholm and Holmgren, *Curr. Trends Microb.*, 1:19-23, 1978.
Taylor et al., *Proc. Natl. Acad. Sci. USA*, 84:2833-2837, 1987.
Tischler and Camilli, *Infect. Immun.*, 73:5873-82, 2005.
Waldor and Mekalanos, *Science*, 272:1910-1914, 1996.
Wickstrum and Egan, *J. Bacteriol.*, 186:6277-6285, 2004.
Withey and DiRita, *J. Bacteriol.*, 187:7890-7900, 2005.
Withey and DiRita, *Mol. Microbiol.*, 56:1062-1077, 2005.
Withey and DiRita, *Mol., Microbiol.*, 59:1779-1789, 2006.
Wood et al., *Mol. Microbiol.*, 34:414-430, 1999.
Yu and DiRita, *J. Bacteriol.*, 181:2584-92, 1999.
Yu and DiRita, *Mol. Microbiol.*, 43:119-134, 2002.

---

What is claimed is:

1. A recombinant *Vibrio cholerae* comprising a mutated transcriptional regulatory protein (ToxT) amino acid sequence, wherein the mutated ToxT comprises a mutation at a lysine corresponding to K203 of SEQ ID NO: 2 or a lysine corresponding to K237 of SEQ ID NO: 2, and wherein the mutation results in a reduction in the expression of cholera toxin by the recombinant *Vibrio cholerae* to less than 1% of the expression of cholera toxin from a *Vibrio cholerae* comprising a wild-type ToxT having the amino acid sequence of SEQ ID NO: 2, and an expression of toxin co-regulated pilus by the recombinant *Vibrio cholerae* that is at least 10% of the expression of toxin co-regulated pilus from a *Vibrio cholerae* comprising a wild-type ToxT having the amino acid sequence of SEQ ID NO: 2.

2. A vaccine comprising a *Vibrio cholerae* that expresses a mutated ToxT, wherein the mutated ToxT comprises a mutation at a lysine corresponding to K203 of SEQ ID NO: 2 or a lysine corresponding to K237 of SEQ ID NO: 2, and wherein the mutation results in reduced expression of cholera toxin by the *Vibrio cholerae* to less than 1% of the expression of cholera toxin from a *Vibrio cholerae* comprising a wild-type ToxT having the amino acid sequence of SEQ ID NO: 2, and an expression of toxin co-regulated pilus by the *Vibrio cholerae* that is at least 10% of the expression of toxin co-regulated pilus from a *Vibrio cholerae* comprising a wild-type ToxT having the amino acid sequence of SEQ ID NO: 2.

3. A method of treating cholera, comprising administering to a subject a vaccine comprising a *Vibrio cholerae* comprising a mutated transcriptional regulatory protein (ToxT) amino acid sequence as set forth in claim 2.

4. The vaccine of claim 2, further comprising one or more immunostimulatory agents.

5. The vaccine of claim 4, wherein the one or more immunostimulatory agents are adjuvants, antigen presenting cells, additional antigens, or immunomodulators.

6. The vaccine of claim 2, further comprising a lipid or liposome.

7. The recombinant *Vibrio cholerae* of claim 1, wherein the mutation is an amino acid substitution.

8. The recombinant *Vibrio cholerae* of claim 7, wherein the amino acid substitution is K203A or K237A.

9. The recombinant *Vibrio cholerae* of claim 1, wherein the expression of toxin co-regulated pilus by the recombinant *Vibrio cholerae* is greater than the expression of toxin co-regulated pilus from a *Vibrio cholerae* comprising a wild-type ToxT having the amino acid sequence of SEQ ID NO: 2.

* * * * *